US007435750B2

(12) United States Patent
Cai et al.

(10) Patent No.: US 7,435,750 B2
(45) Date of Patent: Oct. 14, 2008

(54) METHOD OF USING SUBSTITUTED 3-ARYL-5-ARYL-[1,2,4]-OXADIAZOLES AND ANALOGS AS ACTIVATORS OF CASPASES AND INDUCERS OF APOPTOSIS AND THE USE THEREOF

(75) Inventors: Sui Xiong Cai, San Diego, CA (US); Han-Zhong Zhang, San Diego, CA (US); John A. Drewe, Carlsbad, CA (US); P. Sanjeeva Reddy, San Diego, CA (US); Shailaja Kasibhatla, San Diego, CA (US); Jared Daniel Kuemmerle, Del Mar, CA (US); Kristin P. Ollis, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 228 days.

(21) Appl. No.: 11/074,077

(22) Filed: Mar. 8, 2005

(65) Prior Publication Data

US 2005/0154012 A1 Jul. 14, 2005

Related U.S. Application Data

(62) Division of application No. 10/164,705, filed on Jun. 10, 2002, now Pat. No. 7,041,685.

(60) Provisional application No. 60/296,479, filed on Jun. 8, 2001.

(51) Int. Cl.
| A61K 31/422 | (2006.01) |
| A61K 31/4245 | (2006.01) |
| A61K 31/443 | (2006.01) |
| A61K 31/4709 | (2006.01) |
| A61K 31/4155 | (2006.01) |
| A61K 31/4178 | (2006.01) |
| A61K 31/4025 | (2006.01) |
| A61K 31/381 | (2006.01) |
| A61K 31/341 | (2006.01) |
| A61K 31/519 | (2006.01) |
| A61K 31/4725 | (2006.01) |

(52) U.S. Cl. .............. 514/364; 514/340; 514/314; 514/307; 514/378; 514/406; 514/397; 514/444; 514/461; 514/422; 514/259.31

(58) Field of Classification Search ............... 514/364, 514/340, 314, 307, 378, 406, 397, 444, 461, 514/422, 259.31; 548/131
See application file for complete search history.

(56) References Cited

U.S. PATENT DOCUMENTS

| 3,192,103 A | 6/1965 | Sousa et al. |
| 3,211,742 A | 10/1965 | Lenaers |
| 3,325,446 A | 6/1967 | Chang et al. |
| 3,772,441 A | 11/1973 | Lombardino |
| 3,879,404 A | 4/1975 | Baldwin et al. |
| 3,910,940 A | 10/1975 | Narayanan et al. |
| 4,022,901 A | 5/1977 | Narayanan et al. |
| 4,791,124 A | 12/1988 | Lutomski et al. |
| 5,134,142 A | 7/1992 | Matsuo et al. |
| 6,121,260 A | 9/2000 | Thurkauf et al. |
| 6,277,873 B1 | 8/2001 | Yu et al. |
| 6,620,828 B2 * | 9/2003 | Chu et al. .................. 514/364 |
| 2005/0004005 A1 * | 1/2005 | Kasibhatla et al. ............ 514/2 |

FOREIGN PATENT DOCUMENTS

WO    WO 96/20721 A1    7/1996

OTHER PUBLICATIONS

U.S. Appl. No. 11/593,030, filed Nov. 2006, Cai et al.*
Cancer and apoptosis, Wikipedia, encyclopedia on-line vrsion.*
STN search result on US Patent 6,620,828.*
Batteux, F., et al., "Gene Therapy of Experimental Autoimmune Thyroiditis by In Vivo Administration of Plasmid DNA Coding for Fas Ligand," *J. Immunol.* 162:603-608, The American Association of Immunologists (1999).
Boirivant, M., et al., "Lamina Propria T Cells in Crohn's Disease and Other Gastrointestinal Inflammation Show Defective CD2 Pathway-Induced Apoptosis," *Gastroenterology* 116:557-565, The American Gastroenterological Association (1999).
Chinnaiyan, A.M., et al., "The Inhibition of pro-apoptotic ICE-like proteases enhances HIV replication," *Nat. Med.* 3:333-337, Nature Publishing Co. (1997).
Coven, T.R., et al., "PUVA-induced lymphocyte apoptosis: Mechanism of action in psoriasis," *Photodermatol. Photoimmunol. Photomed.* 15:22-27, Munksgaard (1999).
Ellis, R.E., et al., "Mechanisms and Functions of Cell Death," *Ann. Rev. Cell Biol.* 7:663-698, Annual Reviews, Inc. (1991).
Friesen, C., et al., "Involvement of the CD95 (APO-1/FAS) receptor/ligand system in drug-induced apoptosis in leukemia cells," *Nat. Med.* 2:574-577, Nature Publishing Co. (1996).

(Continued)

Primary Examiner—Joseph McKane
Assistant Examiner—Yong Chu
(74) Attorney, Agent, or Firm—Sterne, Kessler, Goldstein & Fox P.L.L.C.

(57) ABSTRACT

The present invention is directed to substituted 3-aryl-5-aryl-[1,2,4]-oxadiazoles and analogs thereof, represented by the Formula I:

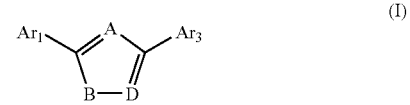

wherein $Ar_1$, $Ar_3$, A, B and D are defined herein. The present invention also relates to the discovery that compounds having Formula I are activators of caspases and inducers of apoptosis. Therefore, the activators of caspases and inducers of apoptosis of this invention may be used to induce cell death in a variety of clinical conditions in which uncontrolled growth and spread of abnormal cells occurs.

12 Claims, No Drawings

OTHER PUBLICATIONS

Greenwald, R.B., "Drug Delivery Systems Employing 1,4- or 1,6-Elimination: Poly(ethylene glycol) Prodrugs of Amine-Containing Compounds," *J. Med. Chem. 42*:3657-3667, American Chemical Society (1999).

Heenen, M., et al., "Methotrexate induces apoptotic cell death in human keratinocytes," *Arch. Dermatol. Res. 290*:240-245, Springer-Verlag (1998).

Infante, A.J., et al., "The clinical spectrum in a large kindred with autoimmune lymphoproliferative syndrome caused by a Fas mutation that impairs lymphocyte apoptosis," *J. Pediatr. 133*:629-633, Mosby, Inc. (1998).

Leu, Y.-L., et al., "Design and Synthesis of Water-Soluble Glucuronide Derivatives of Camptothecin for Cancer Prodrug Monotherapy and Antibody-Directed Enzyme Prodrug Therapy (ADEPT)," *J. Med. Chem. 42*:3623-3628, American Chemical Society (1999).

López-Hoyos, M., et al., "Regulation of B cell apoptosis by Bcl-2 and Bcl-xL and its role in the development of autoimmune diseases (Review)," *Int. J. Mol. Med. 1*:475-483, D.A. Spandidos (1998).

Los, M., et al., "Cross-Resistance of CD95- and Drug-Induced Apoptosis as a Consequence of Deficient Activation of Caspases (ICE/Ced-3 Proteases)," *Blood 90*:3118-3129, W.B. Saunders Co. (1997).

O'Reilly, L.A. and Strasser, A., "Apoptosis and autoimmune disease," *Inflamm. Res. 48*:5-21, Birkhäuser Verlag (1999).

Ohsako, S. and Elkon, K.B., "Apoptosis in the effector phase of autoimmune diabetes, multiple sclerosis and thyroiditis," *Cell Death Differ. 6*:13-21, Stockton Press (1999).

Orrenius, S., "Apoptosis: molecular mechanisms and implications for human disease," *J. Internal Med. 237*:529-536, Blackwell Science Ltd. (1995).

Ozawa, M., et al., "312-nanometer Ultraviolet B Light (Narrow-Band UVB) Induces Apoptosis of T Cells within Psoriatic Lesions," *J. Exp. Med. 189*:711-718, The Rockefeller University Press (1999).

Savill, J., "Apoptosis in resolution of inflammation," *J. Leukoc. Biol. 61*:375-380, The Society for Leukocyte Biology (1997).

Schmitt, E., et al., "The Bcl-xL and BAX-α control points: modulation of apoptosis induced by cancer chemotherapy and relation to TPCK-sensitive protease and caspase activation," *Biochem. Cell Biol. 75*:301-314, National Research Council of Canada (1997).

Tai, D.-I., et al., "Activation of Nuclear Factor κB in Hepatits C Virus Infection: Implications for Pathogenesis and Hepatocarcinogenesis," *Hepatology 3*:656-664, W.B. Saunders Co. (Mar. 2000).

Thornberry, N.A., "The caspase family of cysteine proteases," *Brit. Med. Bull. 53*:478-490, Oxford University Press (1997).

Thornberry, N.A., "Caspases: key mediators of apoptosis," *Chem. Biol. 5*:R97-R103, Current Biology Ltd. (1998).

Vaishnaw, A.K., et al., "The molecular basis for apoptotic defects in patients with CD95 (Fas/Apo-1) mutations," *J. Clin. Invest. 103*:355-363, The American Society for Clinical Investigation (1999).

Wakisaka, S., et al., "Modulation by proinflammatory cytokines of Fas/Fas ligand-mediated apoptotic cell death of synovial cells in patients with rheumatoid arthritis (RA)," *Clin. Exp. Immunol. 114*:119-128, Blackwell Science (1998).

Wyllie, A.H., et al., "Cell Death: The Significance of Apoptosis," *Int. Rev. Cyt. 68*:251-306, Academic Press, Inc. (1980).

Wyllie, A.H., "Cell death: a new classification separating apoptosis from necrosis," in *Cell death in biology and pathology*, Bowen and Lockshin, eds., Chapman and Hall, London, England, pp. 9-34 (1981).

Zhou, T., et al., "Bisindolylmaleimide VIII facilitates Fas-mediated apoptosis and inhibits T cell-mediated autoimmune diseases," *Nat. Med. 5*:42-48, Nature Publishing Co. (1999).

International Search Report for International Patent Application PCT/US02/17892, issued Mar. 26, 2003.

* cited by examiner

METHOD OF USING SUBSTITUTED 3-ARYL-5-ARYL-[1,2,4]-OXADIAZOLES AND ANALOGS AS ACTIVATORS OF CASPASES AND INDUCERS OF APOPTOSIS AND THE USE THEREOF

BACKGROUND OF THE INVENTION

1. Field of the Invention

This invention is in the field of medicinal chemistry. In particular, the invention relates to optionally substituted 3-aryl-5-aryl-[1,2,4]-oxadiazoles and analogs, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or other-wise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Caspase cascade activators and inducers of apoptosis may also be a desirable therapy in the elimination of pathogens, such as HIV, Hepatitis C and other viral pathogens. The long lasting quiecence followed by a disease progression may be explained by anti-apoptotic mechanism of these pathognes leading to persistent cellular reservoirs of the virions. It has been reported that HIV-1 infected T leukemia cells or peripheral blood mononuclear cells (PBMCs) underwent enhanced viral replication in the presence of caspase inhibitor Z-VAD-fmk. Furthermore, Z-VAD-fmk also stimulated endogenous virus production in activated PBMCs derived from HIV-1-infected asymptomatic individuals (Chinnaiyan, A. et. al. *Nature Medicine.* 3:333. 1997). Therefore, apoptosis may serve as a beneficial host mechanism to limit HIV spread and new therapeutics using caspase/apoptosis activators may be useful to clear viral reservoirs from the infected individuals. Similarly, HCV infection also triggers anti-apoptotic mechanisms to evade host's immune surveillance leading to viral persistence and hepatocarcinogenesis (Tai DI et. al. *Hepatology* 3:656-64, 2000). Therefore, apoptosis inducers may be useful as therapeutics for HCV and other infectious disease. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

SUMMARY OF THE INVENTION

The present invention is related to the discovery that optionally substituted 3-aryl-5-aryl-[1,2,4]-oxadiazoles and analogs, as represented in Formula I, are activators of the caspase cascade and inducers of apoptosis. Thus, an aspect of the present invention is directed to the use of compounds of Formula I as inducers of apoptosis.

The compounds of the present invention are represented by Formula I:

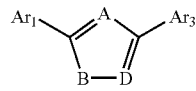

or pharmaceutically acceptable salts or prodrugs or tautomers thereof, wherein:

$Ar_1$ is optionally substituted aryl or optionally substituted heteroaryl;

$Ar_3$ is optionally substituted and selected from the group consisting of arylalkyl, aryloxy, phenoxymethyl, anilino, benzylamino, benzylideneamino, benzoylamino, and $Ar_2$, wherein $Ar_2$ is optionally substituted aryl or optionally substituted heteroaryl; and A, B and D independently are C, $CR_{10}$, $C(R_{10})R_{11}$, N, $NR_{12}$, O or S, wherein $R_{10}$ and $R_{11}$ are at each occurrence independently hydrogen, optionally substituted alkyl, optionally substituted cycloalkyl or optionally substituted aryl and $R_{12}$ is at each occurrence independently hydrogen, optionally substituted alkyl, optionally substituted cycloalkyl or optionally substituted aryl, provided that valency rules are not violated.

A second aspect of the present invention is to provide a method for treating, preventing or ameliorating neoplasia and cancer by administering a compound of one of the Formula I to a mammal in need of such treatment.

Many of the compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of one of the Formula I in admixture with one or more pharmaceutically acceptable carriers or diluents.

A fifth aspect of the present invention is directed to methods for the preparation of novel compounds of Formula I.

DETAILED DESCRIPTION OF THE INVENTION

The present invention arises out of the discovery that optionally substituted 3-aryl-5-aryl-[1,2,4]-oxadiazoles and analogs, as represented in Formula I, are potent and highly efficacious activators of the caspase cascade and inducers of apoptosis. Therefore, compounds of Formula I are useful for treating disorders responsive to induction of apoptosis.

Specifically, compounds of the present invention are represented by Formula I:

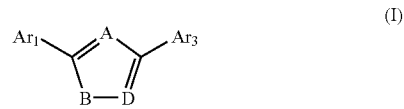

or pharmaceutically acceptable salts or prodrugs or tautomers thereof, wherein:

$Ar_1$ is optionally substituted aryl or optionally substituted heteroaryl;

$Ar_3$ is optionally substituted and selected from the group consisting of arylalkyl, aryloxy, phenoxymethyl, anilino, benzylamino, benzylideneamino, benzoylamino and $Ar_2$, wherein $Ar_2$ is optionally substituted aryl or optionally substituted heteroaryl; and A, B and D independently are C, $CR_{10}$, $C(R_{10})R_{11}$, N, $NR_{12}$, O or S, wherein $R_{10}$ and $R_{11}$ are at each occurrence independently hydrogen, optionally substituted alkyl, optionally substituted cycloalkyl or optionally substituted aryl and $R_{12}$ is at each occurrence independently hydrogen, optionally substituted alkyl, optionally substituted cycloalkyl or optionally substituted aryl, provided that valency rules are not violated. Preferably, $R_{10}$, $R_{11}$ and $R_{12}$ are hydrogen, alkyl, cycloalkyl or aryl; more preferably, $R_{10}$, $R_{11}$ and $R_{12}$ are hydrogen, alkyl or cycloalkyl.

Preferred compounds of Formula I include compounds wherein A is N, B is O and D is N. Another group of preferred compounds of Formula I include compounds wherein A is N, B is $NR_{12}$ and D is N. Another group of preferred compounds of Formula I include compounds wherein A is N, B is $CR_{10}$ and D is $NR_{12}$. Another group of preferred compounds of Formula I include compounds wherein A is O, B and D is N. Another group of preferred compounds of Formula I include compounds wherein A is O, B is N and D is C. Another group of preferred compounds of Formula I include compounds wherein A is N, B is O and D is C. Another group of preferred compounds of Formula I include compounds wherein A is C, B is N and D is $NR_{12}$.

Preferred compounds of Formula I include compounds wherein $Ar_1$ is phenyl, naphthyl, pyridyl, quinolyl, isoquinolyl, isoxazolyl, pyrazolyl, imidazolyl, thienyl, furyl or pyrrolyl, each of which is optionally substituted. More preferably, $Ar_1$ is isoxazolyl, pyrazolyl, imidazolyl, thienyl, furyl or pyrrolyl.

Preferred compounds of Formula I include compounds wherein $Ar_3$ is phenyl, naphthyl, pyridyl, quinolyl, isoquinolyl, isoxazolyl, pyrazolyl, imidazolyl, thienyl, furyl, pyrrolyl, pyrazolo[1,5α]pyrimidinyl, benzyl, phenethyl, phenoxymethyl, benzylamino, benzoylamino, or benzylideneamino, each of which is optionally substituted. More preferably Ar₃ is phenyl, naphthyl, pyridyl, quinolyl, isoquinolyl, isoxazolyl, pyrazolyl, imidazolyl, thienyl, furyl or pyrrolyl. Most preferably Ar₃ is phenyl or pyridyl.

One group of preferred compounds of the present invention are represented by Formula II:

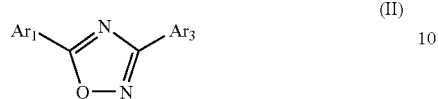
(II)

or pharmaceutically acceptable salts or prodrugs thereof, wherein:

Ar₁ is optionally substituted aryl or optionally substituted heteroaryl;

Ar₃ is optionally substituted and selected from the group consisting of arylalkyl, aryloxy, phenoxymethyl, anilino, benzylamino, benzylideneamino, benzoylamino and Ar₂, wherein Ar₂ is optionally substituted aryl or optionally substituted heteroaryl.

Preferred compounds of Formula II include compounds wherein Ar₁ is phenyl, naphthyl, pyridyl, quinolyl, isoquinolyl, isoxazolyl, pyrazolyl, imidazolyl, thienyl, furyl or pyrrolyl; and wherein Ar₃ is phenyl, naphthyl, pyridyl, quinolyl, isoquinolyl, isoxazolyl, pyrazolyl, imidazolyl, thienyl, furyl or pyrrolyl, each of which is optionally substituted. Preferably Ar₁ is phenyl, pyridyl, isoxazolyl, pyrazolyl, imidazolyl, thienyl, furyl or pyrrolyl, each of which is optionally substituted; and Ar₃ is phenyl, pyridyl, isoxazolyl, pyrazolyl, imidazolyl, thienyl, furyl or pyrrolyl, each of which is optionally substituted. More preferably, Ar₁ is isoxazolyl, pyrazolyl, imidazolyl, thienyl, furyl or pyrrolyl, each of which is optionally substituted; and Ar₃ is optionally substituted phenyl or optionally substituted pyridyl.

Preferably for compounds of Formula II:

(a) when Ar₁ is unsubstituted or substituted thienyl, then Ar₃ is other than phenyl substituted by chloro or trifluoromethyl;

(b) when Ar₁ is unsubstituted or substituted isoxazolyl, then Ar₃ is other than unsubstituted phenyl;

(c) when Ar₁ is substituted or unsubstituted pyrazolyl, then Ar₃ is other than trifluoromethylpyridinyl; and (d) when Ar₁ is substituted or unsubstituted pyrrolyl, then Ar₃ is other than unsubstituted pyridinyl.

Preferably the compounds useful in this aspect of the present invention are represented by Formula III:

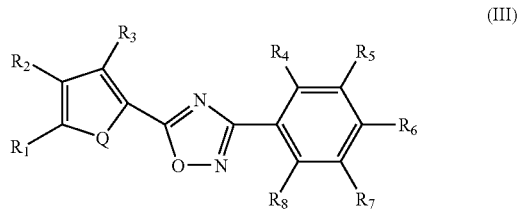
(III)

or a pharmaceutically acceptable salt or prodrug thereof, wherein:

R₁-R₈ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamino, hydroxy, thiol, acyloxy, azido, alkoxy, aryloxy, heteroaryloxy, arylalkoxy, heteroarylalkoxy, haloalkoxy, carboxy, carbonylamido or alkylthiol, each of which is optionally substituted;

Q is S, O or NR₉, wherein R₉ is hydrogen, optionally substituted alkyl, optionally substituted cycloalkyl or optionally substituted aryl. Preferably R₉ is hydrogen, alkyl, cycloalkyl or aryl; more preferably, R₉ is hydrogen, alkyl or cycloalkyl.

Preferred compounds of Formula II include compounds wherein Q is S or O; and wherein R₃ is not a hydrogen.

Another group of preferred compounds of the present invention are represented by Formulae IV-IX:

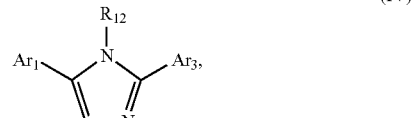
(IV)

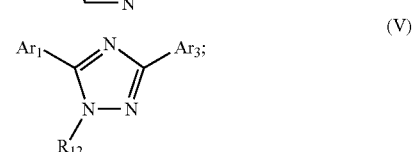
(V)

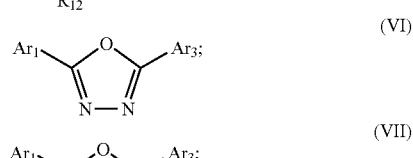
(VI)

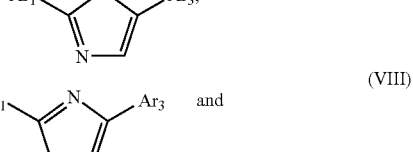
(VII)

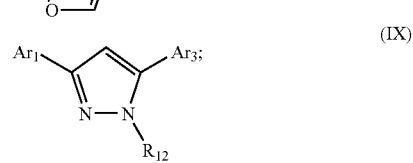
(VIII) and (IX)

and pharmaceutically acceptable salts or prodrugs thereof, wherein:

Ar₁ is optionally substituted aryl or optionally substituted heteroaryl;

Ar₃ is optionally substituted and selected from the group consisting of arylalkyl, aryloxy, phenoxymethyl, anilino, benzylamino, benzylideneamino, benzoylamino and Ar₂, wherein Ar₂ is optionally substituted aryl or optionally substituted heteroaryl; and R₁₂ is hydrogen, optionally substituted alkyl, optionally substituted cycloalkyl or optionally substituted aryl and heteroaryl.

Preferred compounds of Formula II include compounds wherein Ar₁ is phenyl, naphthyl, pyridyl, quinolyl, isoquinolyl, isoxazolyl, pyrazolyl, imidazolyl, thienyl, furyl or pyrrolyl; and wherein Ar₃ is phenyl, naphthyl, pyridyl, quinolyl, isoquinolyl, isoxazolyl, pyrazolyl, imidazolyl, thienyl, furyl or pyrrolyl, each of which is optionally substituted. Preferably Ar₁ is phenyl, pyridyl, isoxazolyl, pyrazolyl, imidazolyl, thienyl, furyl or pyrrolyl, each of which is optionally substituted; and Ar$_3$ is phenyl, pyridyl, isoxazolyl, pyrazolyl, imidazolyl, thienyl, furyl or pyrrolyl, each of which is optionally substituted. More preferably, Ar$_1$ is isoxazolyl, pyrazolyl, imidazolyl, thienyl, furyl or pyrrolyl, each of which is optionally substituted; and Ar$_3$ is optionally substituted phenyl or optionally substituted pyridyl. Preferably R$_{12}$ is hydrogen, optionally substituted alkyl, or optionally substituted aryl and heteroaryl.

Exemplary preferred compounds that may be employed in the method of the invention include, without limitation:

5-(3-Chloro-thiophen-2-yl)-3-(4-trifluoromethyl-phenyl)-[1,2,4]-oxadiazole;
5-(1-Phenyl-5-trifluoromethyl-1H-pyrazol-4-yl)-3-[3,5-bis(trifluoromethyl)phenyl]-[1,2,4]-oxadiazole;
5-[1-(4-Chloro-phenyl)-5-trifluoromethyl-1H-pyrazol-4-yl]-3-[3,5-bis(trifluoromethyl)phenyl]-[1,2,4]-oxadiazole;
5-(4-Bromo-1-ethyl-3-methyl-1H-pyrazol-5-yl)-3-(5-trifluoromethyl-pyridin-2-yl)-[1,2,4]-oxadiazole;
5-(2-Methy-pyrrol-3-yl)-3-(pyridin-3-yl)-[1,2,4]-oxadiazole;
5-(3-Chloro-thiophen-2-yl)-3-[3,5-bis(trifluoromethyl)phenyl]-[1,2,4]-oxadiazole;
5-(3-Chloro-thiophen-2-yl)-3-(4-chloro-phenyl)-[1,2,4]-oxadiazole;
5-(4-Bromo-3-methoxy-thiophen-2-yl)-3-(4-trifluoromethyl-phenyl)-[1,2,4]-oxadiazole;
5-(3-Methyl-5-trifluromethyl-isoxazol-4-yl)-3-phenyl-[1,2,4]-oxadiazole;
3-(4-Amino-3,5-dichloro-phenyl)-5-(thiophen-2-yl)-[1,2,4]-oxadiazole;
3-(4-Methyl-phenyl)-5-(thiophen-2-yl)-[1,2,4]-oxadiazole;
5-(3-Chloro-thiophen-2-yl)-3-(2,4-dichloro-phenyl)-[1,2,4]-oxadiazole;
5-(3-Chloro-thiophen-2-yl)-3-(4-(methylsulphonylamino)phenyl)-[1,2,4]-oxadiazole;
5-(3-Chloro-thiophen-2-yl)-3-(4-methyl-phenyl)-[1,2,4]-oxadiazole;
5-(3-Chloro-thiophen-2-yl)-3-(4-fluoro-phenyl)-[1,2,4]-oxadiazole;
5-(3-Chloro-thiophen-2-yl)-3-(4-nitro-phenyl)-[1,2,4]-oxadiazole;
5-(3-Chloro-thiophen-2-yl)-3-phenyl-[1,2,4]-oxadiazole;
5-(3-Chloro-thiophen-2-yl)-3-(4-trifluoromethoxy-phenyl)-[1,2,4]-oxadiazole;
5-(3-Chloro-thiophen-2-yl)-3-(4-methoxy-phenyl)-[1,2,4]-oxadiazole;
5-(3-Chloro-thiophen-2-yl)-3-(3,4-methylenedioxy-phenyl)-[1,2,4]-oxadiazole;
5-(3-Bromo-thiophen-2-yl)-3-(4-chloro-phenyl)-[1,2,4]-oxadiazole;
5-(3-Chloro-thiophen-2-yl)-3-(pyridin-4-yl)-[1,2,4]-oxadiazole;
5-(3-Chloro-thiophen-2-yl)-3-(4-dimethylamino-phenyl)-[1,2,4]-oxadiazole;
5-(3-Chloro-thiophen-2-yl)-3-(pyridin-3-yl)-[1,2,4]-oxadiazole;
5-(3-Chloro-thiophen-2-yl)-3-(pyridin-2-yl)-[1,2,4]-oxadiazole;
5-(3-Chloro-thiophen-2-yl)-3-(4-hydroxy-phenyl)-[1,2,4]-oxadiazole;
5-(3-Chloro-thiophen-2-yl)-3-(N-oxide-pyridin-4-yl-)-[1,2,4]-oxadiazole;
5-(3-Methyl-furan-2-yl)-3-(4-chloro-phenyl)-[1,2,4]-oxadiazole;
5-(3-Methyl-furan-2-yl)-3-(5-trifluoromethyl-pyridin-2-yl)-[1,2,4]-oxadiazole;
3-(4-Chloro-phenyl)-5-(3-methyl-thiophen-2-yl)-[1,2,4]-oxadiazole;
5-(3-Bromo-furan-2-yl)-3-(4-chloro-phenyl)-[1,2,4]-oxadiazole;
5-(3-Bromo-furan-2-yl)-3-(4-trifluoromethyl-phenyl)-[1,2,4]-oxadiazole;
5-(3-Chloro-thiophen-2-yl)-3-(4-chloro-benzyl)-[1,2,4]-oxadiazole;
5-(4-Chloro-1H-pyrazol-3-yl)-3-(4-chloro-phenyl)-[1,2,4]-oxadiazole;
5-(4-Chloro-1H-pyrazol-3-yl)-3-(5-trifluoromethyl-pyridin-2-yl)-[1,2,4]-oxadiazole;
5-(3-Chloro-furan-2-yl)-3-(4-chloro-phenyl)-[1,2,4]-oxadiazole;
5-(3-Chloro-furan-2-yl)-3-(5-trifluoromethyl-pyridin-2-yl)-[1,2,4]-oxadiazole;
(4-Chloro-benzylidene)-[5-(3-chloro-thiophen-2-yl)-[1,2,4]-oxadiazol-3-yl]-amine;
[5-(3-Chloro-thiophen-2-yl)-[1,2,4]-oxadiazol-3-yl]-(3-trifluoromethyl-benzylidene)-amine;
3-(4-Amino-phenyl)-5-(3-chloro-thiophen-2-yl)-[1,2,4]-oxadiazole;
3-(4-Azido-phenyl)-5-(3-chloro-thiophen-2-yl)-[1,2,4]-oxadiazole;
5-(3-Chloro-thiophen-2-yl)-3-(4-trifluoromethyl-phenyl)-[1,3,4]-oxadiazole;
5-(4-Chloro-thiazol-5-yl)-3-(5-chloro-pyridin-2-yl)-[1,2,4]-oxadiazole;
5-(3-Chloro-thiophen-2-yl)-3-(5-chloro-pyridin-2-yl)-[1,2,4]-oxadiazole;
3-(4-Amino-pyrimidin-5-yl)-5-(3-chloro-thiophen-2-yl)-[1,2,4]-oxadiazole;
5-(3-Chloro-thiophen-2-yl)-3-(5-trifluoromethyl-pyridin-2-yl)-[1,2,4]-oxadiazole;
5-(3-Bromo-5-formyl-furan-2-yl)-3-(4-chloro-phenyl)-[1,2,4]-oxadiazole;
5-(3-Chloro-thiophen-2-yl)-3-(pyrimidin-2-yl)-[1,2,4]-oxadiazole;
5-(3-Chloro-thiophen-2-yl)-3-(N-oxide-pyridin-3-yl)-[1,2,4]-oxadiazole;
5-(3-Chloro-thiophen-2-yl)-3-(6-chloro-pyridin-3-yl)-[1,2,4]-oxadiazole;
5-(3-Chloro-thiophen-2-yl)-3-(4-chloro-3-trifluoromethyl-phenyl)-[1,2,4]-oxadiazole;
5-(3-Chloro-thiophen-2-yl)-3-(3,4-dichloro-phenyl)-[1,2,4]-oxadiazole;
5-(3-Chloro-thiophen-2-yl)-3-(5-trifluoromethyl-pyridin-2-yl)-[1,2,4]-oxadiazole;
3-(3-Bromo-thiophen-2-yl)-5-(4-chloro-phenyl)-[1,2,4]-oxadiazole;
3-(3-Bromo-thiophen-2-yl)-5-(4-trifluoromethyl-phenyl)-[1,2,4]-oxadiazole;
3-(4-Acetamido-phenyl)-5-(3-chloro-thiophen-2-yl)-[1,2,4]-oxadiazole;
5-(3-Chloro-thiophen-2-yl)-3-(3-trifluoromethyl-phenyl)-[1,2,4]-oxadiazole;
5-(3-Chloro-thiophen-2-yl)-3-(6-trifluoromethyl-pyridin-3-yl)-[1,2,4]-oxadiazole;
3-(2-Amino-4-chloro-phenyl)-5-(3-chloro-thiophen-2-yl)-[1,2,4]-oxadiazole;
5-(3-Chloro-thiophen-2-yl)-3-(quinoline-2-yl)-[1,2,4]-oxadiazole;
5-(3-Chloro-thiophen-2-yl)-3-(isoquinoline-3-yl)-[1,2,4]-oxadiazole;
5-(3-Chloro-thiophen-2-yl)-3-(4-methyl-pyridin-2-yl)-[1,2,4]-oxadiazole;

3-(4-Chloro-phenyl)-5-(2-methyl-4-trifluoromethyl-thiazol-5-yl)-[1,2,4]-oxadiazole;
5-(3-Chloro-thiophen-2-yl)-3-(4-cyano-pyridin-2-yl)-[1,2,4]-oxadiazole;
5-(3-Chloro-thiophen-2-yl)-3-(4-cyano-phenyl)-[1,2,4]-oxadiazole;
5-(3-Chloro-thiophen-2-yl)-3-(5-methyl-pyridin-2-yl)-[1,2,4]-oxadiazole;
5-(3-Chloro-thiophen-2-yl)-3-(6-methyl-pyridin-3-yl)-[1,2,4]-oxadiazole;
5-(3-Chloro-thiophen-2-yl)-3-(pyrazin-2-yl)-[1,2,4]-oxadiazole;
5-(3-Chloro-thiophen-2-yl)-3-[4-(methyl carboxy)-phenyl]-[1,2,4]-oxadiazole;
5-(3-Chloro-thiophen-2-yl)-3-(quinolin-3-yl)-[1,2,4]-oxadiazole;
5-(3-Chloro-thiophen-2-yl)-3-(8-hydroxy-quinolin-2-yl)-[1,2,4]-oxadiazole;
5-(3-Cyano-thiophen-2-yl)-3-(5-trifluoromethyl-pyridin-2-yl)-[1,2,4]-oxadiazole;
5-(3-Chloro-thiophen-2-yl)-3-(5,6-dichloro-pyridin-3-yl)-[1,2,4]-oxadiazole;
5-(3-Bromo-furan-2-yl)-3-(5-chloro-pyridin-2-yl)-[1,2,4]-oxadiazole;
5-(3-Bromo-furan-2-yl)-3-(6-trifluoromethyl-pyridin-3-yl)-[1,2,4]-oxadiazole;
5-(3-Bromo-furan-2-yl)-3-(5-trifluoromethyl-pyridin-2-yl)-[1,2,4]-oxadiazole;
5-(3-Chloro-thiophen-2-yl)-3-(2-methyl-thiazol-4-yl)-[1,2,4]-oxadiazole;
5-(3-Chloro-thiophen-2-yl)-3-(5-nitro-thiazol-2-yl)-[1,2,4]-oxadiazole;
5-(3-Chloro-thiophen-2-yl)-3-(7-methyl-5-trifluoromethyl-pyrazolo[1,5α]pyrimidin-3-yl)-[1,2,4]-oxadiazole;
5-(3-Bromo-furan-2-yl)-3-(4-chloro-phenyl)-[1,2,4]-oxadiazole;
5-(3-Chloro-thiophen-2-yl)-3-[2-(4-chloro-phenyl)-ethyl]-[1,2,4]-oxadiazole;
5-(3-Chloro-thiophen-2-yl)-3-(4-chloro-phenoxymethyl)-[1,2,4]-oxadiazole;
5-(3-Chloro-thiophen-2-yl)-2-(4-trifluoromethoxy-phenyl)-1H-imidazole;
5-(3-Bromo-thiophen-2-yl)-2-(4-trifluoromethyl-phenyl)-1H-imidazole;
5-(3-Chloro-thiophen-2-yl)-2-(4-trifluoromethyl-phenyl)-1H-imidazole;
5-(6-Chloro-pyridin-3-yl)-2-(3-chloro-thiophen-2-yl)-[1,3,4]-oxadiazole;
2-(3-Chloro-thiophen-2-yl)-5-(pyridin-3-yl)-[1,3,4]-oxadiazole;
5-(4-Chloro-phenyl)-2-(3-chloro-thiophen-2-yl)-[1,3,4]-oxadiazole;
5-(3-Bromo-5-morpholinomethyl-furan-2-yl)-3-(4-chloro-phenyl)-[1,2,4]-oxadiazole;
5-(3-Bromo-5-hydroxymethyl-furan-2-yl)-3-(4-chloro-phenyl)-[1,2,4]-oxadiazole;
5-(3-Chloro-thiophen-2-yl)-3-(4-trifluoromethyl-phenyl)-1H-[1,2,4]-triazole;
5-(3-Chloro-thiophen-2-yl)-3-phenyl-1H-[1,2,4]-triazole;
5-(3-Chloro-thiophen-2-yl)-3-(4-methyl-phenyl)-1H-[1,2,4]-triazole;
5-(3-Chloro-thiophen-2-yl)-3-(3-methyl-phenyl)-1H-[1,2,4]-triazole;
5-(3-Chloro-thiophen-2-yl)-3-(pyridin-2-yl)-1H-[1,2,4]-triazole;
2-Chloro-thiophen-2-yl)-5-phenyl-oxazole;
5-(4-Bromo-phenyl)-2-(3-chloro-thiophen-2-yl)-oxazole;
2-(3-Chloro-thiophen-2-yl)-5-(4-methoxy-phenyl)-oxazole;
5-(4-Chloro-phenyl)-2-(3-chloro-thiophen-2-yl)-oxazole;
5-(3-Chloro-thiophen-2-yl)-2-phenyl-oxazole;
2-(4-Chloro-phenyl)-5-(3-chloro-thiophen-2-yl)-oxazole;
2-(6-Chloro-pyridin-3-yl)-5-(3-chloro-thiophen-2-yl)-oxazole;
5-(3-Chloro-thiophen-2-yl)-2-(4-trifluoromethyl-phenyl)-oxazole;
2-(3-Chloro-thiophen-2-yl)-4-(4-trifluoromethyl-phenyl)-oxazole;
4-(4-Chloro-phenyl)-2-(3-chloro-thiophen-2-yl)-oxazole;
3-(4-Chloro-phenyl)-5-(3-chloro-thiophen-2-yl)-1H-pyrazole;
4-Chloro-N-[5-(3-chloro-thiophen-2-yl)-[1,2,4]-oxadiazol-3-yl]-benzamide;
5-(4-Chloro-phenyl)-3-(3-chloro-thiophen-2-yl)-1-phenyl-1H-pyrazole;
5-(4-Chloro-phenyl)-3-(3-chloro-thiophen-2-yl)-1-methyl-1H-pyrazole;
5-(4-Chloro-phenyl)-1-(3-chloro-phenyl)-3-(3-chloro-thiophen-2-yl)-1H-pyrazole;
1,5-Bis-(4-chloro-phenyl)-3-(3-chloro-thiophen-2-yl)-1H-pyrazole;
5-(4-Chloro-phenyl)-3-(3-chloro-thiophen-2-yl)-1-(pyridin-2-yl)-1H-pyrazole;
5-(4-Chloro-phenyl)-3-(3-chloro-thiophen-2-yl)-1-(4-carboxy-phenyl)-1H-pyrazole;
5-(4-Chloro-phenyl)-3-(3-chloro-thiophen-2-yl)-1-(4-methanesulfonyl-phenyl)-1H-pyrazole;
5-(4-Chloro-phenyl)-3-(3-chloro-thiophen-2-yl)-1-(2-hydroxyethyl)-1H-pyrazole;
5-(3-Chloro-thiophen-2-yl)-3-(4-chloro-anilino)[1,2,4]-oxadiazole;
5-(3-Bromo-furan-2-yl)-3-(4-fluoro-phenyl)-[1,2,4]-oxadiazole;
5-(3-Chloro-furan-2-yl)-3-(5-chloro-pyridin-2-yl)-[1,2,4]-oxadiazole;
5-(3-Chloro-furan-2-yl)-3-(4-trifluoromethyl-phenyl)-[1,2,4]-oxadiazole;
5-(3-Chloro-furan-2-yl)-3-(4-chloro-phenyl)-[1,2,4]-oxadiazole;
5-(3-Bromo-furan-2-yl)-3-(5-trifluoromethyl-pyridin-2-yl)-[1,2,4]-oxadiazole;
5-(3-Bromo-furan-2-yl)-3-(5-chloro-pyridin-2-yl)-[1,2,4]-oxadiazole;
4-(2-{4-[5-(3-Chloro-thiophen-2-yl)-[1,2,4]-oxadiazol-3-yl]-phenoxy}-ethyl)-morpholine;
(2-{4-[5-(3-Chloro-thiophen-2-yl)-[1,2,4]-oxadiazol-3-yl]-phenoxy}-ethyl)-dimethylamine;
{4-[5-(3-Chloro-thiophen-2-yl)-[1,2,4]-oxadiazol-3-yl]-phenoxy}-acetic acid methyl ester;
5-(3,4,5-Trichloro-thiophen-2-yl)-3-(4-trifluoromethyl-phenyl)-[1,2,4]-oxadiazole;
5-(3-Chloro-thiophen-2-yl)-3-(6-methoxy-pyridin-3-yl)-[1,2,4]-oxadiazole;
3-(4-Butoxy-phenyl)-5-(3-chloro-thiophen-2-yl)-[1,2,4]-oxadiazole; and
3-(4-Amino-3,5-diiodo-phenyl)-5-(3-chloro-thiophen-2-yl)-[1,2,4]-oxadiazole;
and pharmaceutically acceptable salts or prodrugs thereof.

The present invention is also directed to novel compounds within the scope of Formulae I-IX. Exemplary novel compounds of this invention include, without limitation:
5-(3-Chloro-thiophen-2-yl)-3-(4-methyl-phenyl)-[1,2,4]-oxadiazole;
5-(3-Chloro-thiophen-2-yl)-3-(4-fluoro-phenyl)-[1,2,4]-oxadiazole;

5-(3-Chloro-thiophen-2-yl)-3-(4-nitro-phenyl)-[1,2,4]-oxadiazole;
5-(3-Chloro-thiophen-2-yl)-3-phenyl-[1,2,4]-oxadiazole;
3-(4-Methyl-phenyl)-5-(thiophen-2-yl)-[1,2,4]-oxadiazole;
5-(3-Chloro-thiophen-2-yl)-3-(2,4-dichloro-phenyl)-[1,2,4]-oxadiazole;
5-(3-Chloro-thiophen-2-yl)-3-(4-(methylsulphonylamino)phenyl)-[1,2,4]-oxadiazole;
5-(3-Chloro-thiophen-2-yl)-3-(4-trifluoromethoxyphenyl)-[1,2,4]-oxadiazole;
5-(3-Chloro-thiophen-2-yl)-3-(4-methoxyphenyl)-[1,2,4]-oxadiazole;
5-(3-Chloro-thiophen-2-yl)-3-(3,4-methylenedioxyphenyl)-[1,2,4]-oxadiazole;
5-(3-Bromo-thiophen-2-yl)-3-(4-chloro-phenyl)-[1,2,4]-oxadiazole;
5-(3-Chloro-thiophen-2-yl)-3-(pyridin-4-yl)-[1,2,4]-oxadiazole;
5-(3-Chloro-thiophen-2-yl)-3-(4-dimethylaminophenyl)-[1,2,4]-oxadiazole;
5-(3-Chloro-thiophen-2-yl)-3-(pyridin-3-yl)-[1,2,4]-oxadiazole;
5-(3-Chloro-thiophen-2-yl)-3-(pyridin-2-yl)-[1,2,4]-oxadiazole;
5-(3-Chloro-thiophen-2-yl)-3-(4-hydroxyphenyl)-[1,2,4]-oxadiazole;
5-(3-Chloro-thiophen-2-yl)-3-(N-oxide-pyridin-4-yl)-[1,2,4]-oxadiazole;
5-(3-Methyl-furan-2-yl)-3-(4-chloro-phenyl)-[1,2,4]-oxadiazole;
5-(3-Methyl-furan-2-yl)-3-(5-trifluoromethyl-pyridin-2-yl)-[1,2,4]-oxadiazole;
3-(4-Chloro-phenyl)-5-(3-methyl-thiophen-2-yl)-[1,2,4]-oxadiazole;
5-(3-Bromo-furan-2-yl)-3-(4-chloro-phenyl)-[1,2,4]-oxadiazole;
5-(3-Bromo-furan-2-yl)-3-(4-trifluoromethyl-phenyl)-[1,2,4]-oxadiazole;
5-(3-Chloro-thiophen-2-yl)-3-(4-chloro-benzyl)-[1,2,4]-oxadiazole;
5-(4-Chloro-1H-pyrazol-3-yl)-3-(4-chloro-phenyl)-[1,2,4]-oxadiazole;
5-(4-Chloro-1H-pyrazol-3-yl)-3-(5-trifluoromethyl-pyridin-2-yl)-[1,2,4]-oxadiazole;
5-(3-Chloro-furan-2-yl)-3-(4-chloro-phenyl)-[1,2,4]-oxadiazole;
5-(3-Chloro-furan-2-yl)-3-(5-trifluoromethyl-pyridin-2-yl)-[1,2,4]-oxadiazole;
(4-Chloro-benzylidene)-[5-(3-chloro-thiophen-2-yl)-[1,2,4]-oxadiazol-3-yl]-amine;
[5-(3-Chloro-thiophen-2-yl))-[1,2,4]-oxadiazol-3-yl]-(3-trifluoromethyl-benzylidene)-amine;
3-(4-Amino-phenyl)-5-(3-chloro-thiophen-2-yl)-[1,2,4]-oxadiazole;
3-(4-Azido-phenyl)-5-(3-chloro-thiophen-2-yl)-1,2,4]-oxadiazole;
5-(3-Chloro-thiophen-2-yl)-3-(4-trifluoromethyl-phenyl)-[1,3,4]-oxadiazole;
5-(4-Chloro-thiazol-5-yl)-3-(5-chloro-pyridin-2-yl)-[1,2,4]-oxadiazole;
5-(3-Chloro-thiophen-2-yl)-3-(5-chloro-pyridin-2-yl)-[1,2,4]-oxadiazole;
3-(4-Amino-pyrimidin-5-yl)-5-(3-chloro-thiophen-2-yl)-[1,2,4]-oxadiazole;
5-(3-Chloro-thiophen-2-yl)-3-(5-trifluoromethyl-pyridin-2-yl)-[1,2,4]-oxadiazole;
5-(3-Bromo-5-formyl-furan-2-yl)-3-(4-chloro-phenyl)-[1,2,4]-oxadiazole;
5-(3-Chloro-thiophen-2-yl)-3-(pyrimidin-2-yl)-[1,2,4]-oxadiazole;
5-(3-Chloro-thiophen-2-yl)-3-(N-oxide-pyridin-3-yl)-[1,2,4]-oxadiazole;
5-(3-Chloro-thiophen-2-yl)-3-(6-chloro-pyridin-3-yl)-[1,2,4]-oxadiazole;
5-(3-Chloro-thiophen-2-yl)-3-(4-chloro-3-trifluoromethyl-phenyl)-[1,2,4]-oxadiazole;
5-(3-Chloro-thiophen-2-yl)-3-(3,4-dichloro-phenyl)-[1,2,4]-oxadiazole;
5-(3-Chloro-thiophen-2-yl)-3-(5-trifluoromethyl-pyridin-2-yl)-[1,2,4]-oxadiazole;
3-(3-Bromo-thiophen-2-yl)-5-(4-chloro-phenyl)-[1,2,4]-oxadiazole;
3-(3-Bromo-thiophen-2-yl)-5-(4-trifluoromethyl-phenyl)-[1,2,4]-oxadiazole;
3-(4-Acetamido-phenyl)-5-(3-chloro-thiophen-2-yl)-[1,2,4]-oxadiazole;
5-(3-Chloro-thiophen-2-yl)-3-(3-trifluoromethyl-phenyl)-[1,2,4]-oxadiazole;
5-(3-Chloro-thiophen-2-yl)-3-(6-trifluoromethyl-pyridin-3-yl)-[1,2,4]-oxadiazole;
3-(2-Amino-4-chloro-phenyl)-5-(3-chloro-thiophen-2-yl)-[1,2,4]-oxadiazole;
5-(3-Chloro-thiophen-2-yl)-3-(quinoline-2-yl)-[1,2,4]-oxadiazole;
5-(3-Chloro-thiophen-2-yl)-3-(isoquinoline-3-yl)-[1,2,4]-oxadiazole;
5-(3-Chloro-thiophen-2-yl)-3-(4-methyl-pyridin-2-yl)-[1,2,4]-oxadiazole;
3-(4-Chloro-phenyl)-5-(2-methyl-4-trifluoromethyl-thiazol-5-yl)-[1,2,4]-oxadiazole;
5-(3-Chloro-thiophen-2-yl)-3-(4-cyano-pyridin-2-yl)-[1,2,4]-oxadiazole;
5-(3-Chloro-thiophen-2-yl)-3-(4-cyano-phenyl)-[1,2,4]-oxadiazole;
5-(3-Chloro-thiophen-2-yl)-3-(5-methyl-pyridin-2-yl)-[1,2,4]-oxadiazole;
5-(3-Chloro-thiophen-2-yl)-3-(6-methyl-pyridin-3-yl)-[1,2,4]-oxadiazole;
5-(3-Chloro-thiophen-2-yl)-3-(pyrazin-2-yl)-[1,2,4]-oxadiazole;
5-(3-Chloro-thiophen-2-yl)-3-[4-(methyl carboxy)-phenyl]-[1,2,4]-oxadiazole;
5-(3-Chloro-thiophen-2-yl)-3-(quinolin-3-yl)-[1,2,4]-oxadiazole;
5-(3-Chloro-thiophen-2-yl)-3-(8-hydroxy-quinolin-2-yl)-[1,2,4]-oxadiazole;
5-(3-Cyano-thiophen-2-yl)-3-(5-trifluoromethyl-pyridin-2-yl)-[1,2,4]-oxadiazole;
5-(3-Chloro-thiophen-2-yl)-3-(5,6-dichloro-pyridin-3-yl)-[1,2,4]-oxadiazole;
5-(3-Bromo-furan-2-yl)-3-(5-chloro-pyridin-2-yl)-[1,2,4]-oxadiazole;
5-(3-Bromo-furan-2-yl)-3-(6-trifluoromethyl-pyridin-3-yl)-[1,2,4]-oxadiazole;
5-(3-Bromo-furan-2-yl)-3-(5-trifluoromethyl-pyridin-2-yl)-[1,2,4]-oxadiazole;
5-(3-Chloro-thiophen-2-yl)-3-(2-methyl-thiazol-4-yl)-[1,2,4]-oxadiazole;
5-(3-Chloro-thiophen-2-yl)-3-(5-nitro-thiazol-2-yl)-[1,2,4]-oxadiazole;
5-(3-Chloro-thiophen-2-yl)-3-(7-methyl-5-trifluoromethyl-pyrazolo[1,5α]pyrimidin-3-yl)-[1,2,4]-oxadiazole;

5-(3-Bromo-furan-2-yl)-3-(4-chloro-phenyl)-[1,2,4]-oxadiazole;
5-(3-Chloro-thiophen-2-yl)-3-[2-(4-chloro-phenyl)-ethyl]-[1,2,4]-oxadiazole;
5-(3-Chloro-thiophen-2-yl)-3-(4-chloro-phenoxymethyl)-[1,2,4]-oxadiazole;
5-(3-Chloro-thiophen-2-yl)-2-(4-trifluoromethoxy-phenyl)-1H-imidazole;
5-(3-Bromo-thiophen-2-yl)-2-(4-trifluoromethyl-phenyl)-1H-imidazole;
5-(3-Chloro-thiophen-2-yl)-2-(4-trifluoromethyl-phenyl)-1H-imidazole;
5-(6-Chloro-pyridin-3-yl)-2-(3-chloro-thiophen-2-yl)-[1,3,4]-oxadiazole;
2-(3-Chloro-thiophen-2-yl)-5-(pyridin-3-yl)-[1,3,4]-oxadiazole;
5-(4-Chloro-phenyl)-2-(3-chloro-thiophen-2-yl)-[1,3,4]-oxadiazole;
5-(3-Bromo-5-morpholinomethyl-furan-2-yl)-3-(4-chloro-phenyl)-[1,2,4]-oxadiazole;
5-(3-Bromo-5-hydroxymethyl-furan-2-yl)-3-(4-chloro-phenyl)-[1,2,4]-oxadiazole;
5-(3-Chloro-thiophen-2-yl)-3-(4-trifluoromethyl-phenyl)-1H-[1,2,4]-triazole;
5-(3-Chloro-thiophen-2-yl)-3-phenyl-1H-[1,2,4]-triazole;
5-(3-Chloro-thiophen-2-yl)-3-(4-methyl-phenyl)-1H-[1,2,4]-triazole;
5-(3-Chloro-thiophen-2-yl)-3-(3-methyl-phenyl)-1H-[1,2,4]-triazole;
5-(3-Chloro-thiophen-2-yl)-3-(pyridin-2-yl)-1H-[1,2,4]-triazole;
2-(3-Chloro-thiophen-2-yl)-5-phenyl-oxazole;
5-(4-Bromo-phenyl)-2-(3-chloro-thiophen-2-yl)-oxazole;
2-(3-Chloro-thiophen-2-yl)-5-(4-methoxy-phenyl)-oxazole;
5-(4-Chloro-phenyl)-2-(3-chloro-thiophen-2-yl)-oxazole;
5-(3-Chloro-thiophen-2-yl)-2-phenyl-oxazole;
2-(4-Chloro-phenyl)-5-(3-chloro-thiophen-2-yl)-oxazole;
2-(6-Chloro-pyridin-3-yl)-5-(3-chloro-thiophen-2-yl)-oxazole;
5-(3-Chloro-thiophen-2-yl)-2-(4-trifluoromethyl-phenyl)-oxazole;
2-(3-Chloro-thiophen-2-yl)-4-(4-trifluoromethyl-phenyl)-oxazole;
4-(4-Chloro-phenyl)-2-(3-chloro-thiophen-2-yl)-oxazole;
3-(4-Chloro-phenyl)-5-(3-chloro-thiophen-2-yl)-1H-pyrazole;
4-Chloro-N-[5-(3-chloro-thiophen-2-yl)-[1,2,4]-oxadiazol-3-yl]-benzamide;
5-(4-Chloro-phenyl)-3-(3-chloro-thiophen-2-yl)-1-phenyl-1H-pyrazole;
5-(4-Chloro-phenyl)-3-(3-chloro-thiophen-2-yl)-1-methyl-1H-pyrazole;
5-(4-Chloro-phenyl)-1-(3-chloro-phenyl)-3-(3-chloro-thiophen-2-yl)-1H-pyrazole;
1,5-Bis-(4-chloro-phenyl)-3-(3-chloro-thiophen-2-yl)-1H-pyrazole;
5-(4-Chloro-phenyl)-3-(3-chloro-thiophen-2-yl)-1-(pytidin-2-yl)-1H-pyrazole;
5-(4-Chloro-phenyl)-3-(3-chloro-thiophen-2-yl)-1-(4-carboxy-phenyl)-1H-pyrazole;
5-(4-Chloro-phenyl)-3-(3-chloro-thiophen-2-yl)-1-(4-methanesulfonyl-phenyl)-1H-pyrazole;
5-(4-Chloro-phenyl)-3-(3-chloro-thiophen-2-yl)-1-(2-hydroxyethyl)-1H-pyrazole;
5-(3-Chloro-thiophen-2-yl)-3-(4-chloro-anilino)[1,2,4]-oxadiazole;
5-(3-Bromo-furan-2-yl)-3-(4-fluoro-phenyl)-[1,2,4]-oxadiazole;
5-(3-Chloro-furan-2-yl)-3-(5-chloro-pyridin-2-yl)-[1,2,4]-oxadiazole;
5-(3-Chloro-furan-2-yl)-3-(4-trifluoromethyl-phenyl)-[1,2,4]-oxadiazole;
5-(3-Chloro-furan-2-yl)-3-(4-chloro-phenyl)-[1,2,4]-oxadiazole;
5-(3-Bromo-furan-2-yl)-3-(5-trifluoromethyl-pyridin-2-yl)-[1,2,4]-oxadiazole;
5-(3-Bromo-furan-2-yl)-3-(5-chloro-pyridin-2-yl)-[1,2,4]-oxadiazole;
4-(2-{4-[5-(3-Chloro-thiophen-2-yl)-[1,2,4]-oxadiazol-3-yl]-phenoxy}-ethyl)-morpholine;
(2-{4-[5-(3-Chloro-thiophen-2-yl)-[1,2,4]-oxadiazol-3-yl]-phenoxy}-ethyl)-dimethyl-amine;
{4-[5-(3-Chloro-thiophen-2-yl)-[1,2,4]-oxadiazol-3-yl]-phenoxy}-acetic acid methyl ester;
5-(3,4,5-Trichloro-thiophen-2-yl)-3-(4-trifluoromethyl-phenyl)-[1,2,4]-oxadiazole;
5-(3-Chloro-thiophen-2-yl)-3-(6-methoxy-pyridin-3-yl)-[1,2,4]-oxadiazole;
3-(4-Butoxy-phenyl)-5-(3-chloro-thiophen-2-yl)-[1,2,4]-oxadiazole; and
3-(4-Amino-3,5-diiodo-phenyl)-5-(3-chloro-thiophen-2-yl)-[1,2,4]-oxadiazole;
and pharmaceutically acceptable salts or prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, which may be optionally substituted. Alkoxy substituents include, without limitation, halo, morpholino, amino including alkylamino and dialkylamino, and carboxy including esters therof.

Useful alkylthio groups include sulfur substituted by one of the $C_{1-10}$ alkyl groups mentioned above, which may be optionally substituted. Also included are the sulfoxides and sulfones of such alkylthio groups.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

Optional substituents on the alkyl, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl ($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy or carboxy.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroactoms.

Useful heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2α]pyrimidin-4-one, pyrazolo[1,5α]pyrimidinyl, including without limitation pyrazolo[1,5α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I-IX can be prepared as illustrated by the exemplary reaction in Scheme 1. Reaction of 3-chloro-thiophene-2-carbonyl chloride with 4-chlorobenzamidoxime in 1,4-dioxane followed by treatment with $BF_3OEt_2$ produced the product 3-(4-chloro-phenyl)-5-(3-chloro-thiophen-2-yl)-[1,2,4]-oxadiazole. Alternatively, the reaction also can be run in dioxane/pyridine, or in pyridine, and produce the same oxadiazole product.

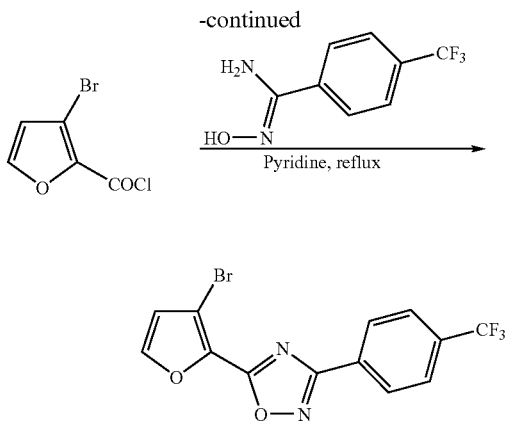

Compounds of this invention with Formula IV may be prepared as illustrated by the exemplary reaction in Scheme 3. Reaction of 2-bromo-1-(3-chloro-thiophen-2-yl)-ethanone with 4-chloro-benzamidine in chloroform produces the product 2-(4-chloro-phenyl)-5-(3-chloro-thiophen-2-yl)-1H-imidazole.

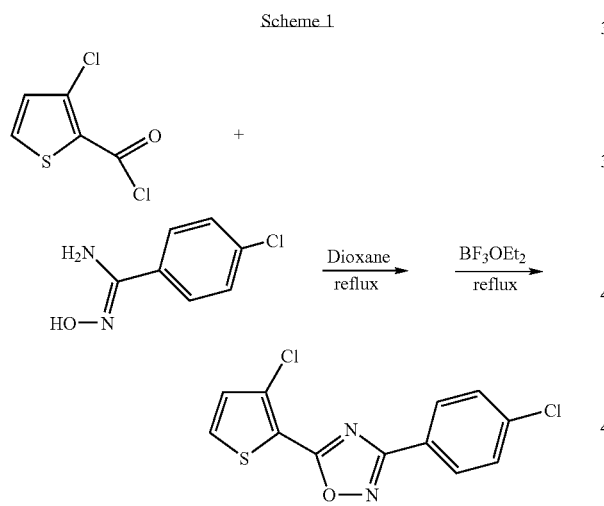

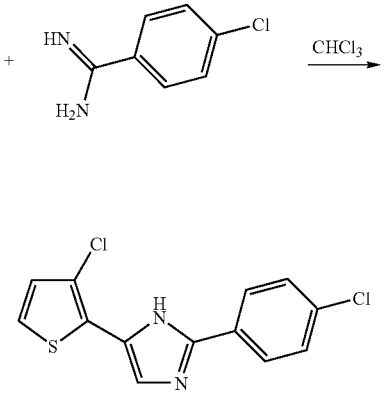

Compounds of this invention with Formulae I-IX may be prepared as illustrated by the exemplary reaction in Scheme 2. Reaction of 3-bromo-furan-2-carboxylic acid with thionyl chloride produces intermediate, 3-bromo-furan-2-carbonyl chloride, followed by refluxing with 4-trifluoromethyl-benzamidoxime in pyridine produces the product 5-(3-bromo-furan)-3-(4-trifluoromethyl-phenyl)-[1,2,4]-oxadiazole.

Compounds of this invention with Formula V may be prepared as illustrated by the exemplary reaction in Scheme 4. Reaction of 3-chloro-thiophene-2-carbonyl chloride with 4-chloro-benzenecarboximidic hydrazide produces the product 3-(4-chloro-phenyl)-5-(3-chloro-thiophen-2-yl)-1H-[1,2,4]-triazole.

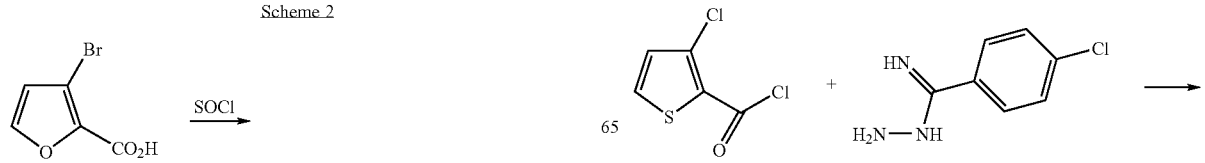

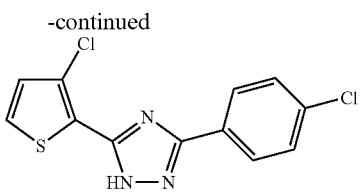

Alternatively, compounds of this invention with Formula V may be prepared as illustrated by the exemplary reaction in Scheme 5. Reaction of 3-chloro-thiophene-2-carboxalic acid hydrazide with 4-chlorobenzamidine in the presence of base, such as NaOMe produces the product 3-(4-chloro-phenyl)-5-(3-chloro-thiophen-2-yl)-1H-[1,2,4]-triazole.

Scheme 5

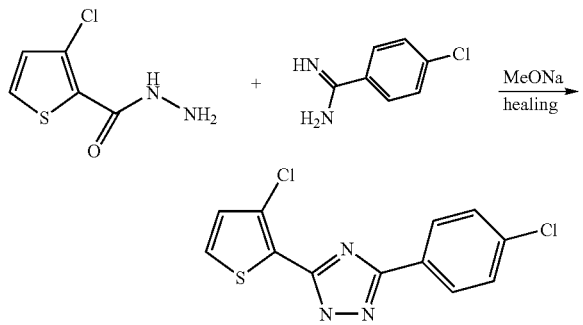

Compounds of this invention with Formula VI may be prepared as illustrated by the exemplary reaction in Scheme 6. Reaction of 3-chloro-thiophene-2-carboxylic acid hydrazide with 4-trifluoromethylbenzoyl chloride produces N-(3-chloro-thiophene-2-carbonyl)-N'-(4-trifluoromethyl-benzoyl)-hydrazine, followed by treating with thionyl chloride produces 5-(3-chloro-2-thienyl)-3-(4-trifluoromethyl-benzoyl)-[1,3,4]-oxadiazole.

Scheme 6

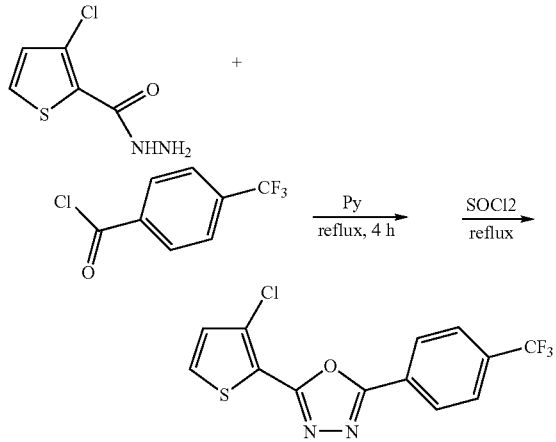

Compounds of Formula VII can be prepared as illustrated by exemplary reaction in Scheme 7. 3-Chloro-thiophene-2-carbonyl chloride was heated in pyridine with an 2-aminoacetophenone hydrochloride to produce the substituted 3-chloro-thiophene-2-carboxylic acid (2-oxo-2-phenyl-ethyl)-amide. Treatment of the compound with acid such as sulfuric acid converted the 3-chloro-thiophene-2-carboxylic acid (2-oxo-2-phenyl-ethyl)-amide into the final product of 2-(3-chloro-thiophen-2-yl)-5-phenyl-oxazole.

Scheme 7

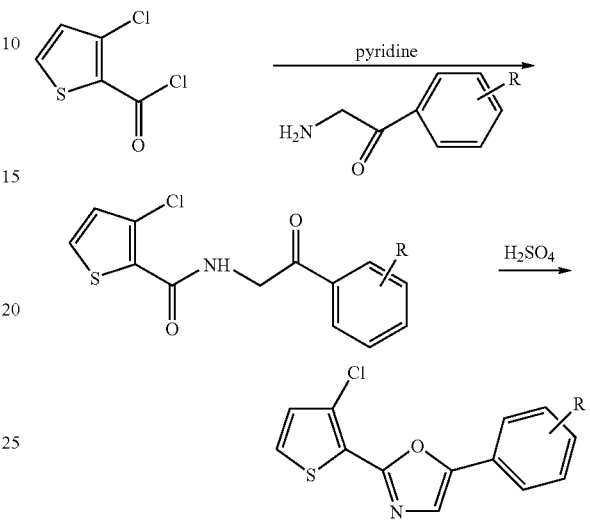

Alternatively, compounds of Formula VII can be prepared as illustrated by exemplary reactions in Scheme 8. Reaction of 2-amino-1-(3-chloro-thiophen-2-yl)-ethanone hydrochloride with a variety of benzoyl chloride produced substituted N-[2-(3-chloro-thiphen-2-yl)-2-oxo-ethyl]-benzamides. Treatment of the compound with acid such as sulfuric acid resulted in the cyclization to give the product of substituted 5-(3-chloro-thiphen-2-yl)-2-phenyl-oxazole.

Scheme 8

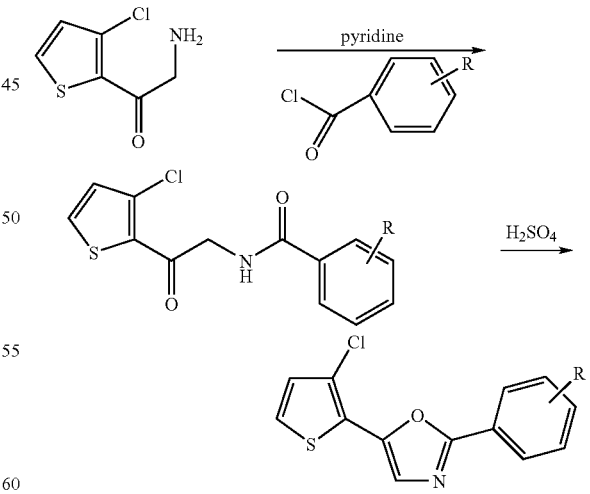

Compounds of Formula VIII can be prepared as illustrated by exemplary reactions in Scheme 9. Reaction of 3-chloro-thiophene-2-carboxamide with a variety of 2-bromo-acetophenone produced the substituted 2-(3-chloro-thiphen-2-yl)-4-pheyl-oxazole.

Scheme 9

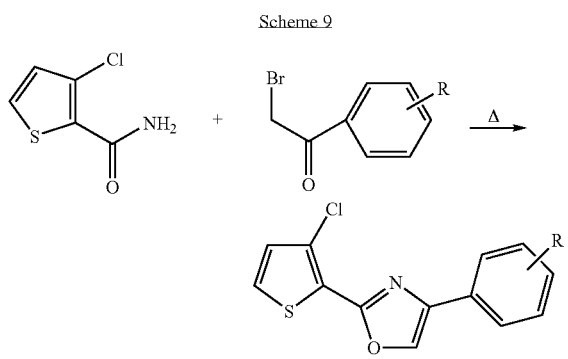

Compounds of Formula IX can be prepared as illustrated by exemplary reaction in Scheme 10. Reaction of 1-(3-chloro-thiophen-2-yl)-1-ethanone with a variety of benzaldehydes afforded substituted 3-phenyl-1-(3-chloro-thiophen-2-yl)-propenone. Reaction of substituted 3-phenyl-1-(3-chloro-thiophen-2-yl)-propenone with substituted hydrazine in the presence of a base such as sodium hydroxide produced the substituted 5-phenyl-3-(3-chloro-thiophen-2-yl)-1-phenyl-4,5-dihydro-1H-pyrazole. The 4,5-dihydro-pyrazole were dehydrogenated with lead tetraacetate followed by treatment with hydrochloric acid to produce the substituted 5-phenyl-3-(3-chloro-thiophen-2-yl)-1-phenyl-1H-pyrazole.

Scheme 10

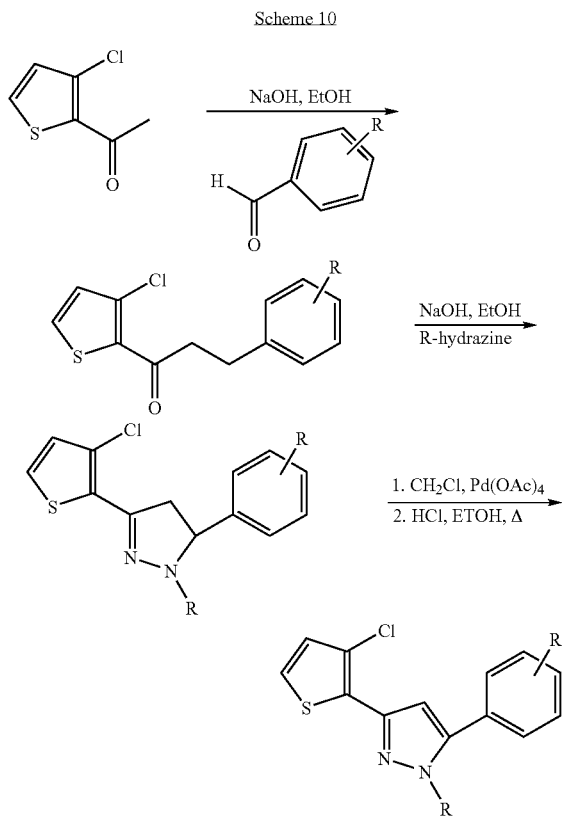

Compounds of this invention with a linker between middle ring and Ar₂ may be prepared as illustrated by the exemplary reaction in Scheme 11. Reaction of 3-chloro-thiophene-2-carbonyl chloride with cyanamide produces N-cyano-3-chloro-thiophene-2-carboxylic acid amide, followed by treating with hydroxyamine to give 3-amino-5-(3-chloro-2-thienyl)-1,2,4-oxadiazole. The amine was refluxed with 4-chlorobenzaldehyde in toluene to produce (4-chloro-benzylidene)-[5-(3-chloro-thiophen-2-yl)-[1,2,4]-oxadiazol-3-yl]-amine.

Scheme 11

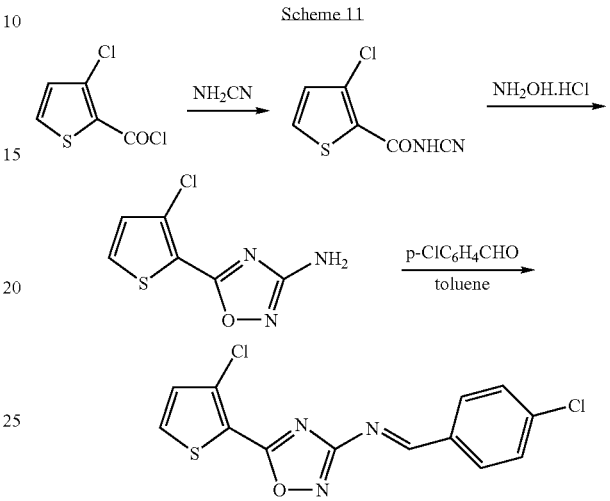

Compounds of this invention with a radioactive label and photoactive group which are useful for the identification of its biological targets may be prepared as illustrated by the exemplary reaction in Scheme 11. The nitro compound was reduced to the amino compound followed by iodination to give the diiodo compound. The iodo can be replaced by tritium, and the amino group can be converted to an azido group via diazotization to give the radiolabeled photoactive target molecule. Alternatively, other isotopes such as $C^{14}$ and other phtoactive groups such as diazo group also can be used for the preparation of radioactive labeled photactive compounds.

Scheme 12

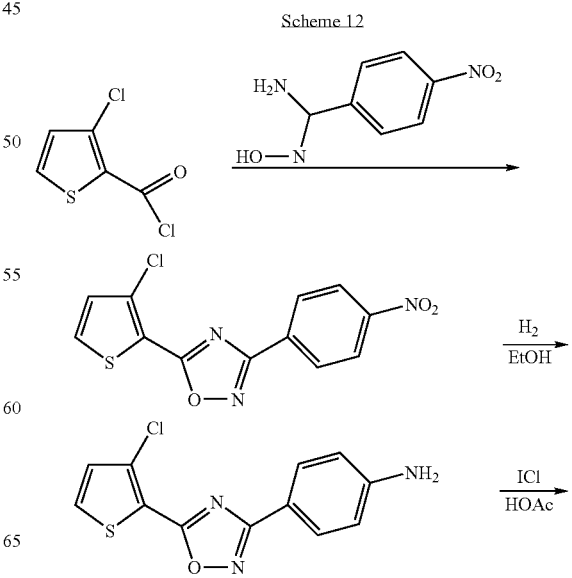

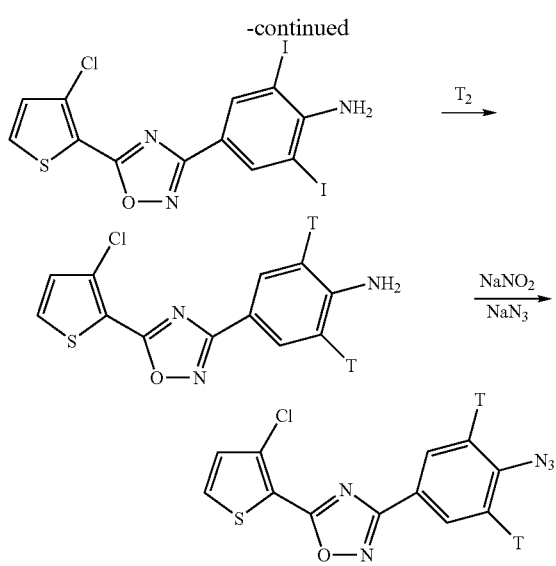

An important aspect of the present invention is the discovery that compounds having Formulae I-IX are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formulae I-IX are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer, such as breast cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I-IX, which functions as a caspase cascade activator and inducer of apoptosis.

The present invention also includes a therapeutic method comprising administering to an animal an effective amount of a compound, or a pharmaceutically acceptable salt or prodrug of said compound of Formulae I-IX, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

In another embodiment, a pharmaceutical composition comprising a compound, or a pharmaceutically acceptable salt of said compound of Formulae I-IX, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-IX, which functions as a caspase cascade activator and inducer of apoptosis, in combination with at least one known cancer chemotherapeutic agent, or a pharmaceutically acceptable salt of said agent. Examples of known cancer chemotherapeutic agents which may be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; antibodies, such as campath, Herceptin® or Rituxan®. Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I-IX, which functions as a caspase cascade activator and inducer of apoptosis, in bioconjugation with at least one known therapeutically useful antibody, such as Herceptin® or Rituxan®; growth factors, such as DGF, NGF; cytokines, such as IL-2, IL-4; or any molecule that binds to the cell surface. The antibodies and other molecules will deliver the compound of Formulae I-IX to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective in inhibiting neoplasia comprising a compound, or a pharmaceutically acceptable salt or prodrug of said compound of Formulae I-IX, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I-IX, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-IX, which functions as a caspase cascade activator and inducer of apoptosis, is an effective treatment for autoimmune diseases.

Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-IX, which functions as a caspase cascade activator and inducer of apoptosis, is be an effective treatment for hyperproliferative skin diseases, such as psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-IX, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-IX, which functions as a caspase cascade activator and inducer of apoptosis, is an effective treatment for inflammation.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated for apoptosis-mediated disorders. Preferably, approximately 0.01 to approximately 10 mg/kg of body weight is orally administered to treat or prevent such disorders. For intramuscular injection, the dose is generally approximately one-half of the oral dose. For example, a suitable intramuscular dose would be approximately 0.0025 to approximately 25 mg/kg of body weight, and most preferably, from approximately 0.01 to approximately 5 mg/kg of body weight. If a known cancer chemotherapeutic agent is also administered, it is administered in an amount that is effective to achieve its intended purpose. The amounts of such known cancer chemotherapeutic agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 10 mg, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, and also preparations that may be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which may be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400), or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

3-(4-Chloro-phenyl)-5-(3-chloro-thiophen-2-yl)-[1,2,4]-oxadiazole

Method A

A solution of 3-chloro-thiophene-2-carbonyl chloride (720 mg, 4 mmol) and 4-chlorobenzamidoxime (680 mg, 4 mmol) in 1,4-dioxane (40 mL) was refluxed for 1 h, then $BF_3OEt_2$ (0.1 mL) was added dropwise. The solution was refluxed for 5 h and evaporated in vacuo, and the residue was purified by column chromatography (silica gel; ethyl acetate:hexane, 1:20) to yield 850 mg (72%) of the title compound. $^1$H NMR ($CDCl_3$): 8.10 (d, J=8.4 Hz, 2H), 7.61 (d, J=5.1 Hz, 1H), 7.49 (d, J=8.4 Hz, 2H), 7.14 (d, J=5.1 Hz, 1H).

Method B

A solution of 3-chloro-thiophene-2-carbonyl chloride (1.45 g, 8 mmol) and 4-chlorobenzamidoxime (1.37 g, 8 mmol) in dioxane/pyridine (110 mL, 10:1) was refluxed for 12 h and cooled to room temperature. To the stirred solution was added water (200 mL) to produce precipitates. The solid was collected by filtration and washed with water (4×20 mL), dried to yield 2.36 g colorless sample, which was further purified by column chromatography (silica gel; ethyl acetate: hexane, 1:10) to yield 2.01 g (85%) of the title compound. $^1$H NMR ($CDCl_3$): 8.10 (d, J=8.4 Hz, 2H), 7.61 (d, J=5.1 Hz, 1H), 7.49 (d, J=8.4 Hz, 2H), 7.13 (d, J=5.1 Hz, 11H).

EXAMPLE 2

5-(3-Chloro-thiophen-2-yl)-3-(4-methyl-phenyl)-[1,2,4]-oxadiazole

The title compound was prepared similar to Example 1, method A. From 3-chloro-thiophene-2-carbonyl chloride (36 mg, 0.2 mmol) and 4-toluamidoxime (30 mg, 0.2 mmol) was obtained 18 mg (33%) of the title compound. $^1$H NMR ($CDCl_3$): 8.04 (d, J=8.1 Hz, 2H), 7.59 (d, J=5.1 Hz, 1H), 7.30 (d, J=8.0 Hz, 2H), 7.12 (d, J=5.1 Hz, 1H), 2.42 (s, 3H).

EXAMPLE 3

3-(4-Methyl-phenyl)-5-(thiophen-2-yl)-[1,2,4]-oxadiazole

The title compound was prepared similar to Example 1, method A. From thiophene-2-carbonyl chloride (48.67 mg, 0.33 mmol) and 4-toluamidoxime (50 mg, 0.33 mmol) was obtained 42 mg (53%) of the title compound. $^1$H NMR ($CDCl_3$): 8.04 (d, J=8.4 Hz, 2H), 7.95 (d, J=3.6 Hz, 1H), 7.66 (d, J=5.1 Hz, 1H), 7.31 (d, J=8.7 Hz, 2H), 7.22 (m, 1H), 2.43 (s, 3H).

EXAMPLE 4

5-(3-Chloro-thiophen-2-yl)-3-(4-trifluoromethyl-phenyl)-[1,2,4]-oxadiazole

A solution of 3-chloro-thiophene-2-carbonyl chloride (455 mg, 2.51 mmol) and 4-trifluoromethyl-benzamidoxime (513 mg, 2.51 mmol) in 1,4-dioxane (50 mL) was refluxed for 1 h, then BF$_3$OEt$_2$ (0.1 mL) was added dropwise. The solution was refluxed for 5 h and cooled to room temperature. To the stirred solution was added water (100 mL) to produce precipitates. The solid was collected by filtration, washed with dioxane:water (1:1), and dried to yield 687 mg (82%) of the title compound. $^1$H NMR (CDCl$_3$): 8.29 (d, J=8.1 Hz, 2H), 7.78 (d, J=8.4 Hz, 2H), 7.63 (d, J=5.1 Hz, 1H), 7.15 (d, J=5.1 Hz, 1H).

EXAMPLE 5

5-(3-Chloro-thiophen-2-yl)-3-(4-fluoro-phenyl)-[1,2,4]-oxadiazole

The title compound was prepared similar to Example 4. From 3-chloro-thiophene-2-carbonyl chloride (181 mg, 1 mmol) and 4-fluorobenzamidoaxime (154 mg, 1 mmol) was obtained 280 mg (99%) of the title compound. $^1$H NMR (CDCl$_3$): 8.29 (d, J=8.4 Hz, 2H), 7.78 (d, J=8.4 Hz, 2H), 7.63 (d, J=5.1 Hz, 1H), 7.15 (d, J=5.1 Hz, 1H).

EXAMPLE 6

5-(3-Chloro-thiophen-2-yl)-3-(4-nitro-phenyl)-[1,2,4]-oxadiazole

The title compound was prepared similar to Example 4. From 3-chloro-thiophene-2-carbonyl chloride (181 mg, 1 mmol) and 4-nitrobenzamidoxime (181 mg, 1 mmol) was obtained 230 mg (75%) of the title compound. $^1$H NMR (CDCl$_3$): 8.37 (s, 4H), 7.65 (d, J=5.1 Hz, 1H), 7.16 (d, J=5.1 Hz, 1H).

EXAMPLE 7

5-(3-Chloro-thiophen-2-yl)-3-(2,4-dichloro-phenyl)-[1,2,4]-oxadiazole

The title compound was prepared similar to Example 4. From 3-chloro-thiophene-2-carbonyl chloride (181 mg, 1 mmol) and 2,4-dichloro-benzamidoxime (205 mg, 1 mmol) was obtained 208 mg (63%) of the title compound. $^1$H NMR (CDCl$_3$): 8.06 (m, 2H), 7.64 (d, J=5.4 Hz, 1H), 7.52 (t, J=1.8 Hz, 1H), 7.15 (d, J=5.1 Hz, 1H).

EXAMPLE 8

5-(3-Chloro-thiophen-2-yl)-3-(4-(methylsulphonylamino)phenyl)-[1,2,4]-oxadiazole The title compound was prepared similar to Example 4. From 3-chloro-thiophene-2-carbonyl chloride (19.9 mg, 0.11 mmol) and 4-(methyl-sulphonylamino)benzamidoxime (22.9 mg, 0.11 mmol) was obtained 14 mg (43%) of the title compound. $^1$H NMR (DMSO-d$_6$): 10.28 (s, 1H), 8.19 (d, J=5.4 Hz, 1H), 8.03 (d, J=9.0 Hz, 2H), 7.43-7.38 (m, 3H), 3.11 (s, 3H).

EXAMPLE 9

5-(3-Chloro-thiophen-2-yl)-3-phenyl-[1,2,4]-oxadiazole

The title compound was prepared similar to Example 4. From 3-chloro-thiophene-2-carbonyl chloride (90 mg, 0.5 mmol) and benzamidoxime (68 mg, 0.5 mmol) was obtained 30 mg (23%) of the title compound. $^1$H NMR (CDCl$_3$): 8.18-8.15 (m, 2H), 7.60 (d, J=5.4 Hz, 1H), 7.54-7.48 (m, 3H), 7.13 (d, J=5.1 Hz, 1H).

EXAMPLE 10

5-(3-Chloro-thiophen-2-yl)-3-(4-trifluoromethoxyphenyl)-[1,2,4]-oxadiazole

A solution of 3-chloro-thiophene-2-carbonyl chloride (72.4 mg, 0.4 mmol) and 4-trifluoromethoxybenzamidoxime (88 mg, 0.4 mmol) in dioxane:pyridine (11 mL, 10:1) was refluxed for 10 h and cooled to room temperature. To the stirred solution was added 20 mL of water to produce precipitates. The solid was collected by filtration and washed with dioxane:water (1:3), and dried to yield 103 mg (75%) of the title compound.
$^1$H NMR (CDCl$_3$): 8.20 (d, J=9.0 Hz, 2H), 7.62 (d, J=5.4 Hz, 1H), 7.35 (bd, J=9.3 Hz, 2H), 7.14 (d, J=5.1 Hz, 1H).

EXAMPLE 11

5-(3-Chloro-thiophen-2-yl)-3-(4-methoxyphenyl)-[1,2,4]-oxadiazole

The title compound was prepared similar to Example 10. From 3-chloro-thiophene-2-carbonyl chloride (72.4 mg, 0.4 mmol) and 4-methoxybenzamidoxime (66.5 mg, 0.4 mmol) was obtained 88 mg (76%) of the title compound. $^1$H NMR (CDCl$_3$): 8.10 (d, J=9.0 Hz, 2H), 7.59 (d, J=5.1 Hz, 1H), 7.12 (d, J=5.1 Hz, 1H), 7.01 (d, J=9.0 Hz, 2H), 3.89 (s, 3H).

EXAMPLE 12

5-(3-Chloro-thiophen-2-yl)-3-(3,4-methylenedioxyphenyl)-[1,2,4]-oxadiazole

The title compound was prepared similar to Example 10. From 3-chloro-thiophene-2-carbonyl chloride (72.4 mg, 0.4 mmol) and 3,4-methylenedioxybenzamidoxime (72 mg, 0.4 mmol) was obtained 100 mg (82%) of the title compound. $^1$H NMR (CDCl$_3$): 7.73 (dd, J=8.1, 1.8 Hz, 1H), 7.60 (s, 1H), 7.59 (d, J=5.4 Hz, 1H), 7.13 (d, J=5.4 Hz, 1H), 6.92 (d, J=7.8 Hz, 1H), 6.06 (s, 2H).

EXAMPLE 13

5-(3-Bromo-thiophen-2-yl)-3-(4-chloro-phenyl)-[1,2,4]-oxadiazole

The title compound was prepared similar to Example 10. From 3-bromo-thiophene-2-carbonyl chloride (67.7 mg, 0.3 mmol) and 4-chloro-benzamidoxime (51 mg, 0.3 mmol) was obtained 101 mg (98%) of the title compound. $^1$H NMR (CDCl$_3$): 8.11 (d, J=8.7 Hz, 2H), 7.60 (d, J=5.4 Hz, 1H), 7.49 (d, J=8.4 Hz, 2H), 7.20 (d, J=5.1 Hz, 1H).

EXAMPLE 14

5-(3-Chloro-thiophen-2-yl)-3-(pyridin-4-yl)-[1,2,4]-oxadiazole

A solution of 3-chloro-thiophene-2-carbonyl chloride (72 mg, 0.40 mmol) and 4-pyridinylamidoxime (55 mg, 0.40 mmol) in 1,4-dioxane (9 mL) and pyridine (1 mL) was refluxed for 3.5 h, heated at 55° C. for 15 h, then refluxed for 5 h. The solution was cooled to room temperature and the product was precipitated by addition of 20 mL of water. The precipitate was filtered and washed with cold water, then dried to yield 31 mg (29%) of the title compound. $^1$H NMR (CDCl$_3$): 8.81 (d, J=6.05 Hz, 2H), 8.03 (dd, J=4.40, 1.65 Hz, 2H), 7.64 (d, J=5.22 Hz, 1H), 7.15 (d, J=5.22 Hz, 1H).

EXAMPLE 15

5-(3-Chloro-thiophen-2-yl)-3-(4-dimethylamino-phenyl)-[1,2,4]-oxadiazole

The title compound was prepared similar to Example 14. From 3-chloro-thiophene-2-carbonyl chloride (55 mg, 0.30 mmol) and 4-dimethylamino-benzamidoxime (55 mg, 0.31 mmol) was obtained 13 mg (14%) of the title compound. $^1$H NMR (CDCl$_3$): 8.01 (m, 2H), 7.56 (d, J=5.22 Hz, 1H), 7.10 (d, J=5.49 Hz, 1H), 6.76 (m, 2H), 3.04 (s, 2H).

EXAMPLE 16

5-(3-Chloro-thiophen-2-yl)-3-(pyridin-3-yl)-[1,2,4]-oxadiazole

A solution of 3-chloro-thiophene-2-carbonyl chloride (79 mg, 0.44 mmol), 3-pyridinylamidoxime (60 mg, 0.44 mmol), and pyridine (1 mL) was refluxed for 5 h. The solution was cooled to ambient temperature and diluted by 4 mL of water to produce a white precipitate. The precipitate was filtered and washed with water, then dried to yield 68 mg (59%) of the title compound. $^1$H NMR (CDCl$_3$): 9.39 (dd, J=2.20, 0.83 Hz, 1H), 8.78 (dd, J=4.95, 1.65 Hz, 1H), 8.43 (dt, J=7.97, 1.92 Hz, 1H), 7.64 (d, J=5.22 Hz, 1H), 7.46 (ddd, J=7.97, 4.81, 0.97 Hz, 1H), 7.15 (d, J=5.22 Hz, 1H).

EXAMPLE 17

5-(3-Chloro-thiophen-2-yl)-3-(pyridin-2-yl)-[1,2,4]-oxadiazole

The title compound was prepared similar to Example 16. From 3-chloro-thiophene-2-carbonyl chloride (54 mg, 0.30 mmol) and 2-pyridinylamidoxime (41 mg, 0.30 mmol) was obtained 45 mg (57%) of the title compound. $^1$H NMR (CDCl$_3$): 8.84 (d, J=4.12 Hz, 1H), 8.22 (d, J=7.97 Hz, 1H), 7.88 (td, J=7.76, 1.74 Hz, 1H), 7.62 (d, J=5.22 Hz, 1H), 7.46 (ddd, J=7.62, 4.74, 1.17 Hz, 1H), 7.14 (d, J=5.22 Hz, 1H).

EXAMPLE 18

5-(3-Chloro-thiophen-2-yl)-3-(4-hydroxy-phenyl)-[1,2,4]-oxadiazole

The title compound was prepared similar to Example 16. From 3-chloro-thiophene-2-carbonyl chloride (37 mg, 0.20 mmol) and 4-hydroxy-phenylamidoxime (31 mg, 0.20 mmol) was obtained 16 mg (28%) of the title compound. $^1$H NMR (CDCl$_3$): 9.12 (sb, 1H), 8.05 (d, J=5.49 Hz, 1H), 8.00 (m, 2H), 7.32 (d, J=5.22 Hz, 1H), 8.22 (m, 2H).

EXAMPLE 19

5-(3-Chloro-thiophen-2-yl)-3-(N-oxide-pyridin-4-yl)-[1,2,4]-oxadiazole

The title compound was prepared similar to Example 16. From 3-chloro-thiophene-2-carbonyl chloride (73 mg, 0.40 mmol) and N-oxide-4-pyridinylamidoxime (62 mg, 0.41 mmol) was obtained 54 mg (48%) of the title compound. $^1$H NMR (60:40, CD$_3$OD:DMSO-d$_6$): 9.16 (d, J=7.14 Hz, 2H), 8.83 (d, J=7.14 Hz, 2H), 8.81 (d, J=5.22 Hz, 1H), 8.07 (d, J=5.49 Hz, 1H).

EXAMPLE 20

3-(4-Chloro-phenyl)-5-(3-methyl-furan-2-yl)-[1,2,4]-oxadiazole

A solution of 3-methyl-furan-2-carboxylic acid (252 mg, 2 mmol), thionyl chloride (0.5 mL) in benzene (5 mL) was stirred at 60° C. for 8 h and evaporated to dryness. The residue was dissolved in pyridine (10 mL), and to the solution was added 4-chloro-benzamidoxime (340 mg, 2 mmol). The solution was refluxed for 10 h and then cooled to room temperature. The solution was diluted by water (20 mL) to produce a precipitate. The solid was collected by filtration and washed with water, then dried to yield 201 mg (39%) of the title compound. $^1$H NMR (CDCl$_3$): 8.12 (d, J=8.4 Hz, 2H), 7.62 (d, J=1.5 Hz, 1H), 7.48 (d, J=8.4 Hz, 2H), 6.50 (d, J=1.5 Hz, 1H).

EXAMPLE 21

5-(3-Methyl-furan-2-yl)-3-(5-trifluoromethyl-pyridin-2-yl)-[1,2,4]-oxadiazole

The title compound was prepared similar to Example 20. From 3-methyl-furan-2-carboxylic acid (126 mg, 1 mmol) and 5-trifluoromethyl-pyridine-2-amidoxime (205 mg, 1 mmol) was obtained 118 mg (40%) of the title compound. $^1$H NMR (CDCl$_3$): 9.07 (s, 1H), 8.35 (d, J=8.4 Hz, 1H), 8.13 (m, 1H), 7.63 (d, J=1.5 Hz, 1H), 6.53 (d, J=1.5 Hz, 1H), 2.56 (s, 3H).

EXAMPLE 22

3-(4-Chloro-phenyl)-5-(3-methyl-thiophen-2-yl)-[1,2,4]-oxadiazole

The title compound was prepared similar to Example 20. From 3-methyl-2-thiophenecarboxylic acid (28.42 mg, 0.2 mmol) and 4-chloro-benzamidoxime (34.1 mg, 0.2 mmol) was obtained 28 mg (51%) of the title compound. $^1$H NMR (CDCl$_3$): 8.10 (d, J=8.7 Hz, 2H), 7.52 (d, J=4.8 Hz, 1H), 7.48 (d, J=8.7 Hz, 2H), 7.03 (d, J=4.8 Hz, 1H), 2.71 (s, 3H).

EXAMPLE 23

5-(3-Bromo-furan-2-yl)-3-(4-chloro-phenyl)-[1,2,4]-oxadiazole

The title compound was prepared similar to Example 20. From 3-bromo-furan-2-carboxylic acid (74 mg, 1 mmol) and 4-chloro-benzamidoxime (72.7 mg, 0.43 mmol) was obtained 28 mg (22%) of the title compound. $^1$H NMR (CDCl$_3$): 8.11 (d, J=9.0 Hz, 1H), 7.67 (d, J=2.1 Hz, 1H), 7.42 (d, J=9.0 Hz, 2H), 6.75 (d, J=1.8 Hz, 1H).

EXAMPLE 24

5-(3-Bromo-furan-2-yl)-3-(4-trifluoromethyl-phenyl)-[1,2,4]-oxadiazole

The title compound was prepared similar to Example 20. From 3-bromo-furan-2-carboxylic acid (38 mg, 0.2 mmol)

and 4-trifluoro-methylbenzamidoxime (41 mg, 0.2 mmol) was obtained 11 mg (15%) of the title compound. $^1$H NMR (CDCl$_3$): 8.33 (d, J=8.7 Hz, 1H), 7.79 (d, J=8.7 Hz, 1H), 7.68 (d, J=2.1 Hz, 1H), 6.76 (d, J=2.1 Hz, 1H).

EXAMPLE 25

5-(3-Chloro-thiophen-2-yl)-3-(4-chloro-benzyl)-[1,2,4]-oxadiazole

The title compound was prepared similar to Example 16. From 3-chloro-thiophene-2-carbonyl chloride (49.2 mg, 0.27 mmol) and 2-(4-chloro-phenyl)-N-hydroxy-acetamidine (50 mg, 0.27 mmol) was obtained 28 mg (33%) of the title compound. $^1$H NMR (CDCl$_3$): 7.57 (d, J=5.1 Hz, 1H), 7.31 (s, 2H), 7.26 (s, 2H), 7.09 (d, J=5.1 Hz, 1H), 4.11 (s, 2H).

EXAMPLE 26

5-(4-Chloro-1H-pyrazol-3-yl)-3-(4-chloro-phenyl)-[1,2,4]-oxadiazole

The title compound was prepared similar to Example 20. From 4-chloro-1H-pyrazole-3-carboxylic acid (34 mg, 0.26 mmol) and 4-chloro-benzamidoxime (45 mg, 26 mmol), was obtained 11 mg (16%) of the title compound. $^1$H NMR (CD$_3$OD): 8.15 (d, J=9.0 Hz, 2H), 8.01 (brs, 1H), 7.59 (d, J=8.7 Hz, 2H).

EXAMPLE 27

5-(4-Chloro-1H-pyrazol-3-yl)-3-(5-trifluoromethyl-pyridin-2-yl)-[1,2,4]-oxadiazole The title compound was prepared similar to Example 20. From 4-chloro-1H-pyrazole-3-carboxylic acid (15 mg, 0.12 mmol) and 5-trifluoro-methyl-pyridine-2-amidoxime (23 mg, 0.12 mmol) was obtained 3 mg (9%) of the title compound. $^1$H NMR (Acetone-d$_6$): 9.15 (s, 1H), 8.46 (s, 2H), 8.24 (s, 1H).

EXAMPLE 28

5-(3-Chloro-furan-2-yl)-3-(4-chloro-phenyl)-[1,2,4]-oxadiazole

The title compound was prepared similar to Example 20. From 3-chloro-furan-2-carboxylic acid (116.8 mg, 0.8 mmol) and 4-chloro-benzamidoxime (136 mg, 0.8 mmol) was obtained 101 mg (45%) of the title compound. $^1$H NMR (CDCl$_3$): 8.12 (d, J=8.4 Hz, 2H), 7.68 (d, J=1.8 Hz, 1H), 7.49 (d, J=8.4 Hz, 2H), 6.69 (d, J=1.8 Hz, 1H).

EXAMPLE 29

5-(3-Chloro-furan-2-yl)-3-(5-trifluoromethyl-pyridin-2-yl)-[1,2,4]-oxadiazole

The title compound was prepared similar to Example 20. From 3-chloro-furan-2-carboxylic acid (14.6 mg, 0.1 mmol) and 5-trifluoromethyl-pyridine-2-amidoxime (20.5 mg, 0.1 mmol) was obtained 5.7 mg (18%) of the title compound. $^1$HNMR(CDCl$_3$): 9.08 (s, 1H), 8.37 (d, J=8.1 Hz, 1H), 8.15 (dd, J=8.1 Hz, 2.4 Hz, 1H), 7.70 (d, J=2.1 Hz, 1H), 6.72 (d, J=2.1 Hz, 1H).

EXAMPLE 30

(4-Chloro-benzylidene)-[5-(3-chloro-thiophen-2-yl)-[1,2,4]-oxadiazol-3-yl]-amine a) N-Cyano-3-chloro-thiophene-2-carboxylic acid amide: To a solution of cyanamide (302.4 mg, 7.2 mmol) in 10% aqueous sodium hydroxide (3 mL) was added 3-chloro-thiophene-2-carbonyl chloride (1.09 g, 6 mmol) in diethyl ether (3 mL). It was stirred for 1 h and acidified with 1N HCl to give precipitates, which was collected by filtration, then washed with water to yield 807 mg (75%) of the title compound.

b) 5-(3-Chloro-thiophen-2-yl)-[1,2,4]-oxadiazol-3-ylamine: A solution of N-cyano-3-chloro-thiophene-2-carboxylic acid amide (467.5 mg, 2.5 mmol), hydroxylamine hydrochloride (174 mg, 2.5 mmol) in pyridine (5 mL) was heated at 100° C. for 8 h. It was cooled and poured into water (80 mL), and the mixture was extracted with ethyl acetate (3×20 mL). The combined organic layer was washed with water, 1N HCl, dried with Na$_2$SO$_4$, and concentrated. The crude residue was purified by column chromatography (hexane:ethyl acetate, 10:1) to yield 189 mg (37%) of title compound. $^1$H NMR (CDCl$_3$): 7.56 (d, J=5.4 Hz, 1H), 7.09 (d, J=5.4 Hz, 1H), 4.49 (brs, 2H).

c) (4-Chloro-benzylidene)-[5-(3-chloro-thiophen-2-yl)-[1,2,4]-oxadiazol-3-yl]-amine: A solution of 5-(3-chloro-thiophen-2-yl)-[1,2,4]-oxadiazol-3-ylamine (15 mg, 0.075 mmol), 4-chlorobenzaldehyde (12.6 mg, 0.09 mmol), acetic acid (3 drops) in toluene (1.4 mL) was refluxed for 16 h. It was evaporated and the residue was purified by column chromatography (hexane:ethyl acetate, 30:1) to yield 4 mg (17%) of title compound. $^1$H NMR (CDCl$_3$): 9.40 (s, 1H), 8.10 (m, 2H), 7.62 (d, J=5.1 Hz, 1H), 7.52 (m, 2H), 7.18 (d, J=5.1 Hz, 1H).

EXAMPLE 31

[5-(3-Chloro-thiophen-2-yl)-[1,2,4]-oxadiazol-3-yl]-(3-trifluoromethyl-benzylidene)-amine The title compound was prepared similar to Example 30c. From 5-(3-chloro-thiophen-2-yl)-[1,2,4]-oxadiazol-3-ylamine (15 mg, 0.075 mmol), 3-trifluoromethylbenzaldehyde (15.7 mg, 0.09 mmol), was obtained 4 mg (15%) of the title compound. $^1$H NMR (CDCl$_3$): 9.33 (s, 1H), 8.36 (s, 1H), 8.25 (d, J=7.5 Hz, 1H), 7.84 (d, J=7.5 Hz, 1H), 7.7.70-7.62 (m, 2H), 7.14 (d, J=5.1 Hz, 1H).

EXAMPLE 32

3-(4-Aminophenyl)-5-(3-chloro-thiophen-2-yl)-[1,2,4]-oxadiazole

A mixture of 5-(3-chloro-thiophen-2-yl)-3-(4-nitro-phenyl)-[1,2,4]-oxadiazole and Pd/C (30 mg) in ethanol (30 mL) under hydrogen (46 psi) was shaken for 6 h. After filtration, the filtrate was concentrated and applied to small column chromatography (hexane:ethyl acetate, 5:1) to yield 18 mg (25%) of the title compound. $^1$H NMR (CDCl$_3$): 7.98 (d, J=8.7 Hz, 2H), 7.60 (d, J=5.1 Hz, 1H), 7.14 (d, J=5.1 Hz, 2H), 6.78 (d, J=8.7 Hz, 1H).

EXAMPLE 33

3-(4-Azidophenyl)-5-(3-chloro-thiophen-2-yl)-[1,2,4]-oxadiazole

To a mixture of 3-(4-aminophenyl)-5-(3-chloro-thiophen-2-yl)-[1,2,4]-oxadiazole (15.5 mg, 0.05 mmol) in acetic acid (2 mL) and conc. sulfinuric acid (0.3 mL) was added sodium nitrite (3.8 mg, 0.055 mmol) in water (0.5 mL). The mixture was stirred vigorously at 0-5° C. for 20 min, then sodium azide (3.6 mg, 0.055 mmol) in water (0.5 mL) was added. It was stirred at 0-5° C. for 3 h and then poured into ice water (30 mL). The resultant mixture was extracted with ethyl acetate (3×10 mL). The organic layer was washed with water, dried over anhydrous sodium sulfate, and evaporated. The crude residue was purified by flash chromatography to yield 16 mg (100%) of the title compound. $^1$H NMR (CDCl$_3$): 8.18 (d, J=8.7 Hz, 2H), 7.63 (d, J=5.4 Hz, 1H), 7.18 (d, J=8.7 Hz, 1H), 7.16 (d, J=5.4 Hz, 2H).

EXAMPLE 34

5-(3-Chloro-thiophen-2-yl)-3-(4-trifluoromethyl-phenyl)-[1,3,4]-oxadiazole a) N-(3-Chloro-thiophene-2-carbonyl)-N'-(4-trifluoromethylbenzoyl)-hydrazine: A solution of 3-chloro-2-thiophenecarboxylic acid hydrazide (70.4 mg, 0.4 mmol), 4-trifluoromethylbenzoyl chloride (83.6 mg, 0.4 mmol) in pyridine (5 mL) was refluxed for 4 h and then cooled. The solution was diluted by water and the precipitate was collected by filtration, and then dried to yield 129 mg (93%) of the title compound.

b) 5-(3-Chloro-thiophen-2-yl)-3-(4-trifluoromethyl-phenyl)-[1,3,4]-oxadiazole: A solution of N-(3-chloro-thiophene-2-carbonyl)-N'-(4-trifluoromethylbenzoyl)-hydrazine (75 mg, 0.22 mmol) in thionyl chloride (8 mL) was refluxed for 6 h. It was evaporated to dryness, followed by column chromatography to yield 58 mg (81%) of title compound. $^1$H NMR (CDCl$_3$): 8.26 (d, J=8.1 Hz, 2H), 7.80 (d, J=8.1 Hz, 2H), 7.56 (d, J=5.4 Hz, 1H), 7.11 (d, J=5.4 Hz, 1H).

EXAMPLE 35

5-(4-Chloro-thiazol-5-yl)-3-(5-chloro-pyridin-2-yl)-[1,2,4]-oxadiazole a) 2,4-Dichloro-thiazole-5-carbaldehyde: N,N-dimethylformamide (1.44 mL, 18.6 mmol) was added over 2 min to a stirred solution of thiazolidine-2,4-dione (1.98 g, 16.9 mmol) and phosphorousoxychloride (10.0 mL, 107 mmol) in an ice bath under argon. The ice bath was removed and the solution was stirred for 1 h at room temperature. The solution was refluxed for 4 h, cooled and poured onto 160 mL of crushed ice. The solution was extracted with dichloromethane (4×50 mL), and the extracts were evaporated. The residue was purified by column chromatography (dichloromethane) to yield 781 mg (25%) of light green solid. $^1$H NMR (CDCl$_3$): 9.97 (s, 1H).

b) 4-Chloro-5-[1,3]dioxolan-2-yl-thiazole: A stirred solution of 2,4-dichloro-thiazole-5-carbaldehyde (747 mg, 4.10 mmol), ethylene glycol (680 µL, 12.2 mmol), p-toluenesulfonic acid monohydrate (1.1 mg, 5.04 µmol), and toluene (15.0 mL) was refluxed for 5 h under argon. The solution was cooled to room temperature and diluted with ether (10 mL). The solution was washed with saturated aqueous sodium bicarbonate solution (20 mL), deionized water (20 mL), and brine (20 mL). The ether layer was dried over sodium sulfate, decanted, and concentrated at 50° C. The product was purified by column chromatography (dichloromethane) to yield 787 mg (85%) of the title compound as a colorless oil. $^1$H NMR (CDCl$_3$): 6.04 (s, 1H), 4.11 (m, 2H), 4.03 (m, 2H).

c) 4-Chloro-thiazole-5-carbaldehyde: A 1.6 M solution of n-butyl-lithium in hexane (2.7 mL, 4.32 mmol) was added dropwise to a stirred solution of 4-chloro-5-[1,3]dioxolan-2-yl-thiazole (787.2 mg, 4.32 mmol) and tetrahydrofuran (20.0 mL) in an ice bath. The solution was stirred for 1 h, equilibrated to room temperature, and poured into a 10% aqueous hydrochloric acid solution (50 mL). The solution was extracted with ether (100 mL). To the extracts were added 10% aqueous hydrochloric acid solution and the resultant solution was stirred for 6 h. The ether layer was washed with brine, dried over sodium sulfate, decanted, and concentrated. The product was purified by column chromatography (dichloromethane) to yield 245 mg (38%) of the title compound as an off-white solid. $^1$H NMR (CDCl$_3$): 10.11 (s, 1H), 9.01 (s, 1H).

d) 4-Chloro-thiazole-5-carboxylic acid: A solution of chomium(IV)oxide (149 mg, 1.49 mmol) in 300 mL deionized water was added dropwise to a stirred solution of 4-chloro-thiazole-5-carbaldehyde (205 mg, 1.37 mmol) and in an ice bath (1.0 mL), followed by addition of sulfuric acid (8 drops). The ice bath was removed and the solution was stirred at ambient temperature for 30 min. Ethyl acetate (30 mL) was added to the solution and the solution was washed with deionized water (4×10 mL) and brine (2×10 mL). The ethyl acetate layer was extracted by a 10% saturated sodium bicarbonate solution (2×20 mL). The aqueous extracts were acidified to pH 3 with a 10% aqueous hydrochloric acid solution and were extracted with 1:1 dichloromethane:ethyl acetate solution (5×15 mL) and ethyl acetate (20 mL). The organic extracts were dried over sodium sulfate, decanted, and concentrated to yield 170 mg (75%) of the title compound as a white solid.

$^1$H NMR (Acetone-d$_6$): 9.20 (s, 1H).

e) 5-(4-Chloro-thiazol-5-yl)-3-(5-chloro-pyridin-2-yl)-[1,2,4]-oxadiazole: To a stirred suspension of 4-chloro-thiazole-5-carboxylic acid (107 mg, 0.655 mmol) in methylene chloride (85 mL) and dimethylformamide (120 µL) in an ice bath under argon, was added oxalyl chloride (450 µL, 0.90 mmol) dropwise. The ice bath was removed, the solution was stirred for 3 h, and the solvent was concentrated. To the residue was added 5-chloro-pyridine-2-amidoxime (113 mg, 0.656 mmol) and pyridine (5 mL) and the solution was refluxed under argon for 2 h. The solution was cooled to room temperature and diluted with deionized water (25 mL) to yield a precipitate. The precipitate was filtered, washed with deionized water (4×5 mL), and dried in vacuo. The product was purified by column chromatography (9:1, dichloromethane:ethyl acetate) followed by recrystallization from ethyl acetate and hexane to yield 96.1 mg (49%) of the title compound as a white solid. $^1$H NMR (CDCl$_3$): 9.00 (s, 1H), 8.82 (d, J=2.47 Hz, 1H), 8.21 (d, J=7.97 Hz, 1H), 7.95 (dd, J=8.52, 2.48 Hz, 1H).

EXAMPLE 36

5-(3-Chlorothiophen-2-yl)-3-(5-chloro-pyridin-2-yl)-[1,2,4]-oxadiazole a) 5-Chloro-2-iodo-pyridine: To a refluxing solution of 2,5-dichloro-pyridine (12.2 g, 82.2 mmol), sodium iodide (37.0 g, 247 mmol) and acetonitrile (170 mL) under argon was added acetyl chloride (9.0 mL, 127 mmol) and the solution was refluxed for 5 h. To the solution was added more sodium iodide (24.9 g, 166 mmol) and the solution was refluxed for 16 h. More sodium iodide (12.5 g, 83.6 mmol) was added and the solution was refluxed for 4.5 h. The solution was cooled to room temperature, and was partitioned between 10% sodium thiosulfate/10% aqueous sodium carbonate (300 mL) and ether (400 mL). The ether layer was washed with brine (100 mL) and dried over anhydrous sodium sulfate. The solution was decanted, and dried in vacuo to yield 16.8 g (85%) of the title compound as a brown solid.

$^1$H NMR (CDCl$_3$): 8.36 (d, J=2.75 Hz, 1H), 7.66 (d, J=8.79 Hz, 1H), 7.32 (dd, J=8.38, 2.61 Hz, 1H). There is 5 mol % of starting material 2,5-dichloro-pyridine in the product as determined by NMR.

b) 5-Chloro-2-cyano-pyridine: A stirred solution of 5-chloro-2-iodo-pyridine (16.6 g, 69.5 mmol), cuprous cyanide (8.15 g, 91.0 mmol) and pyridine (120 mL) was refluxed under argon for 1.5 h. The solution was cooled to room temperature and was poured into an aqueous potassium cyanide solution (56 g/L, 500 mL). The solution was extracted with dichloromethane (4×200 mL). The organic layers were dried over anhydrous sodium sulfate, decanted, and concentrated at 50° C. The product was purified by column (dichloromethane) to yield 6.8 g (70%) of the title compound as a white solid. $^1$H NMR (CDCl$_3$): 8.69 (dd, J=2.47, 0.55 Hz, 1H), 7.84 (dd, J=8.38, 2.34 Hz, 1H), 7.87 (dd, J=8.38, 0.69 Hz, 1H).

c) 5-Chloro-pyridine-2-amidoxime: A solution of 5-chloro-2-cyano-pyridine (6.751 g, 48.7 mmol) and 50 wt % aqueous hydroxylamine (3.5 mL, 57 mmol), ethanol (10 mL), and tetrahydrofuran (50 mL) was stirred at room temperature for 20 min and the solution was concentrated. The product was suspended in hexane (50 mL) and refluxed for 5 min, cooled to room temperature, and filtered to yield 7.9 g (94%) of the title compound as a white solid. $^1$H NMR (DMSO-d$_6$): 10.05 (s, 1H), 8.62 (dd, J=2.34, 0.69 Hz, 1H), 7.94 (dd, J=8.66, 2.34 Hz, 1H), 7.86 (dd, J=8.66, 0.69 Hz, 1H), 5.86 (s, 2H).

d) 5-(3-Chloro-thiophen-2-yl)-3-(5-chloro-pyridin-2-yl)-[1,2,4]-oxadiazole: The title compound was prepared similar to Example 17. From 5-chloro-pyridine-2-amidoxime (3.44 g, 20.0 mmol) and 3-chloro-thiophene-2-carbonyl chloride (3.62 g, 20.0 mmol) was obtained 5.06 g (85%) of the title compound as a white solid. $^1$H NMR (CDCl$_3$): 8.78 (dd, J=2.47, 0.83 Hz, 1H), 8.18 (dd, J=8.38, 0.69 Hz, 1H), 7.86 (dd, J=8.51, 2.47 Hz, 1H), 7.64 (d, J=5.22 Hz, 1H), 7.14 (d, J=5.22 Hz, 1H).

EXAMPLE 37

4-(2-{4-[5-(3-Chloro-thiophen-2-yl)-[1,2,4]-oxadiazol-3-yl]-phenoxy}-ethyl)-morpholine To a mixture of 4-[5-(3-chloro-thophen-2-yl)-[1,2,4]-oxadiazol-3-yl]-phenol (50 mg, 0.179 mmol) and potassium carbonate (25 mg, 0.179 mmol) in anhydrous ethanol (1 mL) was added 4-(2-chloroethyl)morpholine (66.7 mg, 0.358 mmol). The reaction mixture was refluxed for 1 h and then cooled to room temperature to form precipitates. The precipitates were filtered to yield 33.3 mg (47.3%) of the title compound as a tan solid. $^1$H NMR (DMSO-d$_6$): 8.18 (d, J=5.7 Hz, 1H), 7.98 (d, J=8.7 Hz, 2H), 7.41 (d, J=7.41 Hz, 1H), 7.15 (d, J=8.7 Hz, 2H), 4.35 (m, 2H), 4.18 (m, 2H), 3.58 (m, 3H), 3.43 (m, 3H), 2.72 (m, 2H).

EXAMPLE 38

(2-{4-[5-(3-Chloro-thiophen-2-yl)-[1,2,4]-oxadiazol-3-yl]-phenoxy}-ethyl)-dimethyl-amine The title compound was prepared from 4-[5-(3-chloro-thiophen-2-yl)-[1,2,4]-oxadiazol-3-yl]-phenol and 2-(dimethylamino)ethyl bormide by a procedure similar to that of Example 37. $^1$H NMR (DMSO-d$_6$): 8.18 (d, J=5.4 Hz, 1H), 7.98 (d, J=9.0 Hz, 2H), 7.41 (d, J=5.4 Hz, 1H), 7.15 (d, J=8.7 Hz, 2H), 4.14 (t, 2H), 2.61 (m, 2H), 2.48 (m, 6H).

EXAMPLE 39

{4-[5-(3-Chloro-thiophen-2-yl)-[1,2,4]-oxadiazol-3-yl]-phenoxy}-acetic acid methyl ester The title compound was prepared from 4-[5-(3-chloro-thiophen-2-yl)-[1,2,4]-oxadiazol-3-yl]-phenol and methyl bromoacetate by a procedure similar to that of Example 37 as a white solid, (30.3 mg, 52.0%). $^1$H NMR (DMSO-d$_6$): 8.18 (d, J=5.1 Hz, 1H), 8.00 (d, J=8.7 Hz, 2H), 7.42 (d, J=5.1 Hz, 1H), 7.15 (d, J=9.0 Hz, 2H), 4.90 (s, 2H), 1.2 (m, 3H).

EXAMPLE 40

5-(3,4,5-Trichloro-thiophen-2-yl)-3-(4-trifluoromethyl-phenyl)-[1,2,4]-oxadiazole The title compound was prepared as in Example 16 from 3,4,5-trichloro-thiophene-2-carboxyl chloride (0.150 g, 0.600 mmol) and 4-trifluoro-methyl-benzamidoxime (0.122 g, 0.600 mmol) as a white solid (0.208 g, 87%). $^1$H NMR (DMSO-d$_6$): 8.7 (d, J=8.7 Hz, 2H), 7.99 (d, J=8.4 Hz, 2H).

EXAMPLE 41

5-(3-Chloro-thiophen-2-yl)-3-(6-methoxy-pyridin-3-yl)-[1,2,4]-oxadiazole

The title compound was prepared as in Example 16 from 3-chloro-thiophene-2-carbonyl chloride (0.150 g, 0.828 mmol) and 6-methoxy-pyridine-3-amidoxime (0.138 g, 0.828 mmol) as a white solid (166 mg, 63%).

$^1$H NMR (DMSO-d$_6$): 8.84 (d, J=2.4 Hz, 1H), 8.28 (m, 1H), 8.20 (d, J=6.0 Hz, 1H), 7.42 (d, J=5.1 Hz, 1H), 7.04 (d, J=9.3 Hz, 1H).

EXAMPLE 42

3-(4-Butoxy-phenyl)-5-(3-chloro-thiophen-2-yl)-[1,2,4]-oxadiazole a) 4-Butoxy-benzamidoxime: The title compound was prepared as in Example 36c from hydroxylamine (0.195 mL) and 4-butoxybenzonitrile (0.500 g, 2.85 mmol) as a white solid (0.534 g, 92%). $^1$H NMR (DMSO-d$_6$): 9.44 (s, 1H), 7.58 (d, J=8.7 Hz, 2H), 6.90 (d, J=9.0 Hz, 2H), 5.74 (s, 2H), 3.97 (m, 2H), 1.72 (m, 2H), 1.42 (m, 2H), 0.928 (t, 3H).

b) 3-(4-Butoxy-phenyl)-5-(3-chloro-thiophen-2-yl)-[1,2,4]-oxadiazole: The title compound was prepared as in Example 16 from 3-chloro-thiophene-2-carbonyl chloride (86 mg, 0.480 mmol) and 4-butoxy-benzamidoxime (100 mg, 0.480 mmol) as a tan solid (0.113 g, 71%). $^1$H NMR (Acetone-d$_6$): 8.10 (d, J=1.8 Hz, 1H), 8.08 (d, J=2.1 Hz, 1H), 7.36 (d, J=3.9 Hz, 1H), 7.16 (d, J=8.7 Hz, 2H), 4.14 (t, 2H), 1.95 (m, 2H), 1.56 (m, 2H), 0.928 (t, 3H).

EXAMPLE 43

3-(4-Aminopyrimidin-5-yl)-5-(3-chloro-thiophen-2-yl)-[1,2,4]-oxadiazole

The title compound was prepared from 4-amino-pyrimidine-5-amidoxime (50 mg, 0.33 mmol) and 3-chloro-thiophene-2-carbonyl chloride (59 mg, 0.33 mmol), similar to Example 16, and yielded 25 mg (27%) of yellow solid. $^1$H NMR (CDCl$_3$): 9.18 (s, 1H), 8.69 (s, 1H), 7.66 (d, J=5.22 Hz, 1H), 7.16 (d, J=5.22 Hz, 1H), 5.85 (s, 1H), 3.51 (s, 1H).

EXAMPLE 44

5-(3-Chloro-thiophen-2-yl)-3-(5-trifluoromethyl-pyridin-2-yl)-[1,2,4]-oxadiazole The title compound was prepared from 5-trifluoromethyl-pyridine-2-amidoxime (429 mg, 2.09 mmol) and 3-chloro-thiophene-2-carbonyl chloride (378 mg, 2.09 mmol) similar to Example 16, and yielded 535 mg (77%) of white solid. $^1$H NMR (CDCl$_3$): 9.09 (m, 1H), 8.36 (d, J=8.24 Hz, 1H), 8.14 (m, 1H), 7.66 (d, J=5.22 Hz, 1H), 7.16 (d, J=5.22 Hz, 1H).

EXAMPLE 45

5-(3-Bromo-5-formyl-furan-2-yl)-3-(4-chloro-phenyl)-[1,2,4]-oxadiazole

A solution of 5-(3-bromo-furan-2-yl)-3-(4-chloro-phenyl)-[1,2,4]-oxadiazole (599 mg, 1.84 mmol) in tetrahydrofuran (10 mL) was added under argon over 20 min to a stirred solution of 1.5 M lithium diisopropylamide (1.3 mL, 1.95 mmol) and tetrahydrofuran (10 mL) in a dry ice/acetone bath, and it was stirred for 1 h. To the solution was then added dry DMF (1.5 mL, 19.4 mmol) dropwise and the solution was stirred for 30 min. The dry ice bath was replaced by an ice bath and the solution was stirred for 20 min. The ice bath was removed and the solution was quenched with methanol (10 mL) and then saturated sodium bicarbonate (3 mL). To the solution was added 1 N hydrochloric acid until the solution reach pH 3. The solution was extracted with dichloromethane (2×100 mL). The extracts were dried over sodium sulfate, filtered, and concentrated. The product was purified twice by column chromatography (dichloromethane) to yield 393 mg (60%) of the title compound as a light yellow solid. $^1$H NMR (DMSO-d$_6$): 9.79 (s, 1H), 8.11 (dd, J=8.52, 2.13 Hz, 2H), 8.05 (s, 1H), 7.70 (dd, J=8.24, 2.06 Hz, 2H).

EXAMPLE 46

5-(3-Chloro-thiophen-2-yl)-3-(pyrimidin-2-yl)-[1,2,4]-oxadiazole a) Pyrimidine-2-amidoxime: The title compound was prepared from 2-cyanopyrimidine (341 mg, 3.25 mmol) and 0.576 M hydroxylamine hydrochloride in 95% ethanol (5.65 mL, 3.25 mmol), similar to Example 36c, and yielded 293 mg (65%) of white solid. $^1$H NMR (DMSO-d$_6$): 10.17 (s, 1H), 8.84 (d, J=4.94 Hz, 2H), 7.51 (t, J=4.81 Hz, 1H), 5.83 (s, 2H).

b) 5-(3-Chloro-thiophen-2-yl)-3-(pyrimidin-2-yl)-[1,2,4]-oxadiazole: The title compound was prepared from pyrimidine-2-amidoxime (41 mg, 0.30 mmol) and 3-chloro-thiophene-2-carbonyl chloride (51 mg, 0.28 mmol) similar to Example 16, and yielded 35 mg (39%) of white solid. $^1$H NMR (CDCl$_3$): 9.02 (d, J=4.67 Hz, 2H), 7.65 (d, J=5.22 Hz, 1H), 7.49 (t, J=4.81 Hz, 1H), 7.15 (d, J=5.22 Hz, 1H).

EXAMPLE 47

5-(3-Chloro-thiophen-2-yl)-3-(N-oxide-pyridin-3-yl)-[1,2,4]-oxadiazole

The title compound was prepared from N-oxide-pyridine-3-amidoxime (53 mg, 0.35 mmol) and 3-chloro-thiophene-2-carbonyl chloride (63 mg, 0.35 mmol) similar to Example 16, and yielded 38 mg (39%) of white solid. $^1$H NMR (CDCl$_3$): 8.96 (m, 1H), 8.34 (m, 1H), 8.03 (d, J=7.96 Hz, 1H), 7.76 (d, J=5.22 Hz, 1H), 7.50 (m, 1H), 7.19 (d, J=5.50 Hz, 1H).

EXAMPLE 48

5-(3-Chloro-thiophen-2-yl)-3-(6-chloro-pyridin-3-yl)-[1,2,4]-oxadiazole a) 6-Chloro-pyridine-3-amidoxime: The title compound was prepared from 6-chloro-3-cyano-pyridine (416 mg, 3.00 mmol) and 0.576 M hydroxylamine hydrochloride in 95% ethanol (5.8 mL, 3.3 mmol) similar to Example 36c, and yielded 275 mg (53%) of white solid. $^1$H NMR (Acetone-d$_6$): 9.26 (s, 1H), 8.71 (dd, J=2.47, 0.82 Hz, 1H), 8.10 (dd, J=8.24, 2.47 Hz, 1H), 7.47 (dd, J=8.40, 0.69 Hz, 1H), 5.69 (s, 2H).

b) 5-(3-Chloro-thiophen-2-yl)-3-(6-chloro-pyridin-3-yl)-[1,2,4]-oxadiazole: The title compound was prepared from 6-chloro-pyridine-3-amidoxime (47 mg, 0.27 mmol) and 3-chloro-thiophene-2-carbonyl chloride (50 mg, 0.28 mmol), similar to Example 16, and yielded 49 mg (27%) of light pink solid. $^1$H NMR (CDCl$_3$): 9.16 (d, J=2.20 Hz, 1H), 8.39 (dd, J=8.24, 2.20 Hz, 1H), 7.65 (d, J=5.22 Hz, 1H), 7.49 (d, J=8.52 Hz, 1H), 7.15 (d, J=5.22 Hz, 1H).

EXAMPLE 49

5-(3-Chloro-thiophen-2-yl)-3-(4-chloro-3-trifluoromethyl-phenyl)-[1,2,4]-oxadiazole a) 4-Chloro-3-trifluoromethyl-benzamidoxime: The title compound was prepared from 4-chloro-3-trifluoromethyl-benzonitrile (617 mg, 3.00 mmol) and 0.576 M hydroxylamine hydrochloride in 95% ethanol (5.8 mL, 3.3 mmol) similar to Example 36c, and yielded 528 mg (74%) of white solid.

$^1$H NMR (Acetone-d$_6$): 9.29 (s, 1H), 8.15 (d, J=2.19 Hz, 1H), 8.00 (m, 1H), 7.69 (d, J=8.24 Hz, 1H), 5.73 (s, 2H).

b) 5-(3-Chloro-thiophen-2-yl)-3-(4-chloro-3-trifluoromethyl-phenyl)-[1,2,4] oxadiazole: The title compound was prepared from 4-chloro-3-trifluoromethyl-benzamidoxime (66 mg, 0.28 mmol) and 3-chlorothio-phene-2-carbonyl chloride (50 mg, 0.28 mmol) similar to Example 16, and yielded 68 mg (68%) of white solid. $^1$H NMR (CDCl$_3$): 8.49 (d, J=1.64 Hz, 1H), 8.28 (dd, J=8.52, 1.92 Hz, 1H), 7.66 (m, 2H), 7.15 (d, J=5.22 Hz, 1H).

EXAMPLE 50

5-(3-Chloro-thiophen-2-yl)-3-(3,4-dichloro-phenyl)-[1,2,4]-oxadiazole a) 3,4-Dichloro-benzamidoxime: The title compound was prepared from 3,4-dichloro-benzonitrile (516 mg, 3.00 mmol) and 0.576 M hydroxylamine hydrochloride in 95% ethanol (5.8 mL, 3.3 mmol), similar to Example 36c, and yielded 276 mg (45%) of white solid. $^1$H NMR (Acetone-d$_6$): 9.21 (s, 1H), 7.89 (d, J=2.20 Hz, 1H), 7.70 (dd, J=8.52, 2.20 Hz, 1H), 7.58 (d, J=8.52 Hz, 1H), 5.62 (s, 2H).

b) 5-(3-Chloro-thiophen-2-yl)-3-(3,4-dichloro-phenyl)-[1,2,4]-oxadiazole: The title compound was prepared from 3,4-dichlorobenzamidoxime (57 mg, 0.28 mmol) and 3-chloro-thiophene-2-carbonyl chloride (50 mg, 0.28 mmol) similar to Example 16, and yielded 63 mg (69%) of white solid. $^1$H NMR (CDCl$_3$): 8.27 (d, J=1.38 Hz, 1H), 8.00 (dd, J=8.46, 1.52 Hz, 1H), 7.63 (d, J=5.50 Hz, 1H), 7.59 (d, J=8.24 Hz, 1H), 7.14 (d, J=5.22 Hz, 1H).

EXAMPLE 51

5-(3-Chloro-thiophen-2-yl)-3-(5-trifluoromethyl-pyridin-2-yl)-[1,2,4]-oxadiazole The title compound was prepared from 5-trifluoromethyl-pyridine-2-amidoxime (516 mg, 2.52 mmol) and 3-chloro-thiophene-2-carbonyl chloride (455 mg, 2.51 mmol) similar to Example 16, and yielded 764 mg (92%) of off-white solid. $^1$H NMR (CDCl$_3$): 9.09 (m, 1H), 8.36 (d, J=8.24 Hz, 1H), 8.14 (m, 1H), 7.66 (d, J=5.22 Hz, 1H), 7.16 (d, J=5.49 Hz, 1H).

EXAMPLE 52

3-(3-Bromo-thiophen-2-yl)-5-(4-chloro-phenyl)-[1,2,4]-oxadiazole a) 3-Bromo-thiophene-2-amidoxime: The title compound was prepared from 3-bromo-2-cyano-thiophene (564 mg, 3.00 mmol) and 0.576 M hydroxylamine hydrochloride in 95% ethanol (5.8 µL, 3.3 mmol) similar to Example 36c, and yielded 383 mg (58%) of white solid. $^1$H NMR (Acetone-d$_6$): 9.18 (s, 1H), 7.51 (d, J=5.50 Hz, 1H), 7.06 (d, J=5.22 Hz, 1H), 5.59 (s, 2H).

b) 3-(3-Bromo-thiophen-2-yl)-5-(4-chloro-phenyl)-[1,2,4]-oxadiazole: The title compound was prepared from 4-chloro-benzoyl chloride (60 µL, 0.47 mmol) and 3-bromo-thiophene-2-amidoxime (102 mg, 0.461 mmol) similar to Example 36c, and yielded 80 mg (51%) of white solid. $^1$H NMR (CDCl$_3$): 8.15 (dd, J=9.09, 2.06 Hz, 2H), 7.54 (dd, J=8.51, 2.20 Hz, 2H), 7.50 (d, J=5.22 Hz, 1H), 7.18 (d, J=5.22 Hz, 1H).

EXAMPLE 53

3-(3-Bromo-thiophen-2-yl)-5-(4-trifluoromethyl-phenyl)-[1,2,4]-oxadiazole

The title compound was prepared from 4-trifluoromethyl-benzoyl chloride (66 µL, 0.44 mmol) and 3-bromo-thiophene-2-amidoxime (98 mg, 0.44 mmol) similar to Example 16, and yielded 130 mg (78%) of white solid.
$^1$H NMR (CDCl$_3$): 8.34 (d, J=8.24 Hz, 2H), 7.83 (d, J=8.51 Hz, 2H), 7.52 (d, J=5.22 Hz, 1H), 7.19 (d, J=5.21 Hz, 1H).

EXAMPLE 54

3-(4-Acetamido-phenyl)-5-(3-chloro-thiophen-2-yl)-[1,2,4]-oxadiazole

The title compound was prepared from 4-acetamidobenz amidoxime (55.4 mg, 0.287 mmol) and 3-chloro-thiophene-2-carbonyl chloride (52.4 mg, 0.289 mmol) similar to Example 16, and yielded 33.6 mg (37%) of light orange solid. $^1$H NMR (CDCl$_3$): 8.12 (d, J=8.52 Hz, 2H), 7.66 (d, J=8.79 Hz, 2H), 7.60 (d, J=5.22 Hz, 1H), 7.35 (s, 1H), 7.12 (d, J=5.22 Hz, 1H).

EXAMPLE 55

5-(3-Chloro-thiophen-2-yl)-3-(3-trifluoromethyl-phenyl)-[1,2,4]-oxadiazole

The title compound was prepared from 3-trifluoromethyl-benzamidoxime (70.3 mg, 0.344 mmol) and 3-chloro-thiophene-2-carbonyl chloride (62 mg, 0.343 mmol), similar to Example 16, and yielded 81.6 mg (72%) as an off-white solid. $^1$H NMR (CDCl$_3$): 8.44 (s, 1H), 8.36 (d, J=7.69 Hz, 1H), 7.80 (d, J=8.51 Hz, 1H), 7.67 (d, J=7.96 Hz, 1H), 7.64 (d, J=5.21 Hz, 1H), 7.15 (d, J=5.22 Hz, 1H).

EXAMPLE 56

5-(3-Chloro-thiophen-2-yl)-3-(6-trifluoromethyl-pyridin-3-yl)-[1,2,4]-oxadiazole The title compound was prepared from 6-trifluoromethyl-pyridine-3-amidoxime (418 mg, 2.04 mmol) and 3-chloro-thiophene-2-carbonyl chloride (369 mg, 2.04 mmol) similar to Example 16, and yielded 538 mg (80%) of white solid. $^1$H NMR (CDCl$_3$): 9.49 (m, 1H), 8.63 (m, 1H), 7.85 (dd, J=8.24, 0.82 Hz, 1H), 7.66 (d, J=5.49 Hz, 1H), 7.17 (d, J=5.22 Hz, 1H).

EXAMPLE 57

3-(2-Amino-4-chloro-phenyl)-5-(3-chloro-thiophen-2-yl)-[1,2,4]-oxadiazole a) 2-Amino-4-chloro-benzamidoxime: The title compound was prepared from 2-amino-4-chloro-benzonitrile (458 mg, 3.00 mmol) and 0.576 M hydroxylamine hydrochloride in 95% ethanol (5.8 mL, 3.3 mmol) similar to Example 36c, yielded 377 mg (68%) of light yellow solid. $^1$H NMR (Acetone-d$_6$): 8.99 (s, 1H), 7.42 (d, J=8.51 Hz, 1H), 6.77 (d, J=1.92 Hz, 1H), 6.56 (dd, J=8.52, 2.20 Hz, 1H), 6.30 (s, 2H), 5.51 (s, 2H).

b) 3-(2-Amino-4-chloro-phenyl)-5-(3-chloro-thiophen-2-yl)-[1,2,4]-oxadiazole: The title compound was prepared from 2-amino-4-chloro-benzamidoxime (63.2 mg, 0.336 mmol) and 3-chloro-thiophene-2-carbonyl chloride (62 mg, 0.343 mmol) similar to Example 16, and yielded 16.2 mg (16%) of yellow solid. $^1$H NMR (CDCl$_3$): 8.07 (d, J=9.07 Hz, 1H), 7.62 (d, J=5.22 Hz, 1H), 7.14 (d, J=5.22 Hz, 1H), 6.78 (m, 2H), 5.53 (s, 2H).

EXAMPLE 58

5-(3-Chloro-thiophen-2-yl)-3-(quinoline-2-yl)-[1,2,4]-oxadiazole a) Quinoline-2-amidoxime: The title compound was prepared from 2-cyano-quinoline (463 mg, 3.00 mmol) and 50 wt % hydroxylamine (200 µL, 3.26 mmol) similar to Example 36c, and yielded 554 mg (98%) of light yellow solid. $^1$H NMR (DMSO-d$_6$): 10.23 (s, 1H), 8.34 (d, J=8.79 Hz, 1H), 8.06 (d, J=8.51 Hz, 1H), 8.00 (d, J=8.24 Hz, 2H), 7.80 (t, J=7.69 Hz, 1H), 7.62 (dd, J=7.97, 6.87 Hz, 1H), 6.01 (s, 2H).

b) 5-(3-Chloro-thiophen-2-yl)-3-(quinoline-2-yl)-[1,2,4]-oxadiazole: The title compound was prepared from quinoline-2-amidoxime (64.5 mg, 0.346 mmol) and 3-chloro-thiophene-2-carbonyl chloride (62.5 mg, 0.345 mmol) similar to Example 16, and yielded 31 mg (29%) of white solid. $^1$H NMR (CDCl$_3$): 8.36 (d, J=8.52 Hz, 2H), 8.30 (d, J=8.51 Hz, 1H), 7.92 (dd, J=7.97, 1.38 Hz, 1H), 7.81 (ddd, J=8.45, 7.07, 1.44 Hz, 1H), 7.65 (m, 2H), 7.15 (d, J=5.22 Hz, 1H).

EXAMPLE 59

5-(3-Chloro-thiophen-2-yl)-3-(isoquinoline-3-yl)-[1,2,4]-oxadiazole a) Isoquinoline-3-amidoxime: The title compound was prepared from isoquinoline-3-carbonitrile (364 mg, 2.36 mmol) and 50 wt % hydroxylamine (160 µL, 2.61 mmol) similar to Example 36c, and yielded 439 mg (99%) of light yellow solid. $^1$H NMR (DMSO-$d_6$): 9.81 (s, 1H), 9.35 (s, 1H), 8.31 (s, 1H), 8.16 (dd, J=8.17, 0.75 Hz, 1H), 8.06 (d, J=7.97 Hz, 1H), 7.80 (ddd, J=8.24, 6.87, 1.37 Hz, 1H), 7.70 (ddd, J=8.11, 6.87, 1.24 Hz, 1H), 5.97 (s, 2H).

b) 5-(3-Chloro-thiophen-2-yl)-3-(isoquinoline-3-yl)-[1,2,4]-oxadiazole: The title compound was prepared from isoquinoline-3-amidoxime (64.7 mg, 0.346 mmol) and 3-chloro-thiophene-2-carbonyl chloride (62.5 mg, 0.343 mmol) similar to Example 16, and yielded 65.8 mg (61%) of off-white solid. $^1$H NMR (CDCl$_3$): 9.43 (s, 1H), 8.64 (s, 1H), 8.08 (d, J=7.42 Hz, 1H), 8.00 (d, J=7.97 Hz, 1H), 7.80 (td, J=7.49, 1.46 Hz, 1H), 7.73 (td, J=7.48, 1.10 Hz, 1H), 7.63 (d, J=5.22 Hz, 1H), 7.15 (d, J=5.50 Hz, 1H).

EXAMPLE 60

5-(3-Chloro-thiophen-2-yl)-3-(4-methyl-pyridin-2-yl)-[1,2,4]-oxadiazole a) 4-Methyl-pyridine-2-amidoxime: The title compound was prepared 4-methyl-pyridine-2-carbonitrile (441 mg, 3.73 mmol) and 50 wt % hydroxylamine (250 µL, 4.08 mmol), similar to Example 36c, and yielded 427 mg (76%) of white solid. $^1$H NMR (DMSO-$d_6$): 9.85 (s, 1H), 8.41 (d, J=4.94 Hz, 1H), 7.68 (m, 1H), 7.24 (m, 1H), 5.81 (s, 2H), 2.34 (s, 3H).

b) 5-(3-Chloro-thiophen-2-yl)-3-(4-methyl-pyridin-2-yl)-[1,2,4]-oxadiazole: The title compound was prepared from 4-methyl-pyridine-2-amidoxime (50.5 mg, 0.334 mmol) and 3-chloro-thiophene-2-carbonyl chloride (60.7 mg, 0.335 mmol) similar to Example 16, and yielded 72.7 mg (80%) of off-white solid. $^1$H NMR (CDCl$_3$): 8.68 (dd, J=4.95, 0.83 Hz, 1H), 8.04 (m, 1H), 7.62 (d, J=5.22 Hz, 1H), 7.27 (m, 1H), 7.13 (d, J=5.50 Hz, 1H), 2.48 (s, 3H).

EXAMPLE 61

5-(2-Methyl-4-trifluoromethyl-thiazol-5-yl)-3-(4-chloro-phenyl)-[1,2,4]-oxadiazole The title compound was prepared from 4-chlorobenzamidoxime and 2-methyl-4-trifluoromethyl-thiazole-5-carboxylate similar to Example 16 as a light orange solid. $^1$H NMR (CDCl$_3$): 8.08 (dd, J=8.52, 2.20 Hz, 1H), 7.50 (dd, J=8.51, 2.13 Hz, 1H), 2.85 (s, 3H).

EXAMPLE 62

5-(3-Chloro-thiophen-2-yl)-3-(4-cyano-pyridin-2-yl)-[1,2,4]-oxadiazole a) 4-Cyano-pyridine-2-amidoxime: The title compound was prepared from 2,4-dicyano-pyridine (481 mg, 3.72 mmol), 50 wt % hydroxylamine (240 µL, 3.92 mmol) similar to Example 36c, and yielded 452 mg (75%) of white solid. $^1$H NMR (DMSO-$d_6$): 9.52 (s, 1H), 8.81 (dd, J=5.08, 0.96 Hz, 1H), 7.18 (dd, J=1.51, 0.96 Hz, 1H), 7.66 (dd, J=5.22, 1.65 Hz, 1H), 5.85 (s, 2H).

b) 5-(3-Chloro-thiophen-2-yl)-3-(4-cyano-pyridin-2-yl)-[1,2,4]-oxadiazole: The title compound was prepared from 4-cyano-pyridine-2-amidoxime (49.1 mg, 0.303 mmol) and 3-chloro-thiophene-2-carbonyl chloride (55 mg, 0.30 mmol) similar to Example 16, and yielded 73.5 mg (84%) of off-white solid. $^1$H NMR (CDCl$_3$): 9.03 (d, J=4.94 Hz, 1H), 8.45 (m, 1H), 7.70 (dd, J=4.94, 1.37 Hz, 1H), 7.67 (d, J=5.22 Hz, 1H), 7.16 (d, J=5.49 Hz, 1H).

EXAMPLE 63

5-(3-Chloro-thiophen-2-yl)-3-(4-cyano-phenyl)-[1,2,4]-oxadiazole a) 4-Cyano-benzamidoxime: The title compound was prepared from terephthalonitrile (384 mg, 3.00 mmol), 50 wt % hydroxylamine (200 µL, 3.26 mmol) similar to Example 36c, and yielded 196 mg (41%) of white solid. $^1$H NMR (DMSO-$d_6$): 10.04 (s, 1H), 7.86 (s, 4H), 6.01 (s, 2H).

b) 5-(3-Chloro-thiophen-2-yl)-3-(4-cyano-phenyl)-[1,2,4]-oxadiazole: The title compound was prepared from 4-cyano-benzamidoxime (49.0 mg, 0.304 mmol) and 3-chloro-thiophene-2-carbonyl chloride (55 mg, 0.30 mmol) similar to Example 16, and yielded 73.4 mg (84%) of white solid. $^1$H NMR (CDCl$_3$): 8.29 (dd, J=8.24, 1.65 Hz, 2H), 7.81 (dd, J=8.24, 1.51 Hz, 2H), 7.65 (d, J=5.22 Hz, 1H), 7.15 (d, J=5.22 Hz, 1H).

EXAMPLE 64

5-(3-Chloro-thiophen-2-yl)-3-(5-methyl-pyridin-2-yl)-[1,2,4]-oxadiazole a) 5-Methyl-pyridine-2-amidoxime: 5-methyl-2-bromopyridine (505 mg, 2.93 mmol) was melted with cuprous cyanide (287 mg, 3.20 mmol) for a few seconds. The mixture was cooled to room temperature and extracted with ethyl acetate (3×5 mL). The extracts were filtered and concentrated to yield 86 mg of a light green solid. To the solid was added 50 wt % hydroxylamine (45 µL, 0.73 mmol), and ethanol (5 mL) and the resultant solution was refluxed under argon for 30 min. The solution was cooled to room temperature and concentrated to dryness. The product was purified by column chromatography (95:5, ethyl acetate:methanol) to yield 60.7 mg (14%) of the title compound as a white solid. $^1$H NMR (Acetone-$d_6$): 9.01 (s, 1H), 8.39 (dd, J=1.38, 0.83 Hz, 1H), 7.81 (d, J=7.96 Hz, 1H), 7.59 (m, 1H), 5.69 (s, 1H), 2.35 (s, 3H).

b) 5-(3-Chloro-thiophen-2-yl)-3-(5-methyl-pyridin-2-yl)-[1,2,4]-oxadiazole: The title compound was prepared from 5-methyl-pyridine-2-amidoxime (26 mg, 0.17 mmol) and 3-chloro-thiophene-2-carbonyl chloride (31.7 mg, 0.175 mmol) similar to Example 16, and yielded 39.4 mg (82%) of an off-white solid. $^1$H NMR (CDCl$_3$): 8.66 (m, 1H), 8.10 (d, J=7.97 Hz, 1H), 7.67 (m, 1H), 7.61 (d, J=5.22 Hz, 1H), 7.13 (d, J=5.22 Hz, 1H), 2.44 (s, 3H).

EXAMPLE 65

5-(3-Chloro-thiophen-2-yl)-3-(6-methyl-pyridin-3-yl)-[1,2,4]-oxadiazole a) 6-Methyl-pyridine-3-amidoxime: The title compound was prepared from 6-methyl-nicotinenitrile (354 mg, 3.00 mmol), 50 wt % hydroxylamine (200 µL, 3.26 mmol) similar to Example 36c, yielded 300 mg (66%) of white solid. $^1$H NMR (DMSO-$d_6$): 9.74 (s, 1H), 8.72 (d, J=2.19 Hz, 1H), 7.89 (dd, J=8.10, 2.33 Hz, 1H), 7.26 (d, J=8.24 Hz, 1H), 5.93 (s, 2H).

b) 5-(3-Chloro-thiophen-2-yl)-3-(6-methyl-pyridin-3-yl)-[1,2,4]-oxadiazole: The title compound was prepared from 6-methyl-pyridine-3-amidoxime (45.9 mg, 0.304 mmol) and 3-chloro-thiophene-2-carbonyl chloride (55 mg, 0.30 mmol) similar to Example 16, and yielded 60.8 mg (72%) of an off-white solid. $^1$H NMR (CDCl$_3$): 9.25 (d, J=2.20 Hz, 1H), 8.31 (dd, J=7.97, 2.20 Hz, 1H), 7.63 (d, J=5.49 Hz, 1H), 7.31 (d, J=7.97 Hz, 1H), 7.14 (d, J=5.22 Hz, 1H), 2.66 (s, 3H).

EXAMPLE 66

5-(3-Chloro-thiophen-2-yl)-3-(pyrazin-2-yl)-[1,2,4]-oxadiazole

The title compound was prepared from pyrazine-2-amidoxime (42.2 mg, 0.306 mmol) and 3-chloro-thiophene-2-carbonyl chloride (55 mg, 0.30 mmol) similar to Example 16, and yielded 67.4 mg (84%) of white solid. $^1$H NMR (CDCl$_3$): 9.45 (d, J=1.37 Hz, 1H), 8.81 (dd, J=2.48, 1.65 Hz, 1H), 8.77 (d, J=2.47 Hz, 1H), 7.66 (d, J=4.95 Hz, 1H), 7.16 (d, J=5.50 Hz, 1H).

EXAMPLE 67

5-(3-Chloro-thiophen-2-yl)-3-[4-(methyl carboxy)-phenyl]-[1,2,4]-oxadiazole a) 4-(Methyl carboxy)-benzamidoxime: The title compound was prepared from 4-(methyl carboxy)-benzonitrile (483 mg, 3.00 mmol), 50 wt % hydroxylamine (195 µL, 3.18 mmol) similar to Example 36c, and yielded 403 mg (69%) of white solid. $^1$H NMR (DMSO-$d_6$): 9.91 (s, 1H), 7.95 (dd, J=8.79, 1.86 Hz, 2H), 7.82 (dd, J=8.79, 1.79 Hz, 2H), 5.94 (s, 2H), 3.86 (s, 3H).

b) 5-(3-Chloro-thiophen-2-yl)-3-[4-(methyl carboxy)-phenyl]-[1,2,4]-oxadiazole: The title compound was prepared from 4-(methyl carboxy)-benzamidoxime (234 mg, 1.21 mmol) and 3-chloro-thiophene-2-carbonyl chloride (218.7 mg, 1.21 mmol) similar to Example 16, and yielded 340 mg (88%) of white solid. $^1$H NMR (CDCl$_3$): 8.25 (m, 2H), 8.17 (m, 2H), 7.63 (d, J=5.36 Hz, 1H), 7.14 (d, J=5.22 Hz, 1H).

EXAMPLE 68

5-(3-Chloro-thiophen-2-yl)-3-(quinolin-3-yl)-[1,2,4]-oxadiazole a) Quinoline-3-amidoxime: The title compound was prepared from 3-cyano-quinoline (464 mg, 3.01 mmol) and 50 wt % hydroxylamine (200 µL, 3.26 mmol) similar to Example 36c, and yielded 141 mg (25%) of light yellow solid. $^1$H NMR (DMSO-$d_6$): 10.01 (s, 1H), 9.22 (d, J=1.93 Hz, 1H), 8.58 (d, J=1.64 Hz, 1H), 8.01 (dd, J=12.09, 8.24 Hz, 2H), 7.78 (td, J=7.63, 1.28 Hz, 1H), 7.65 (t, J=7.56 Hz, 1H), 6.11 (s, 2H).

b) 5-(3-Chloro-thiophen-2-yl)-3-(quinolin-3-yl)-[1,2,4]-oxadiazole: The title compound was prepared from quinoline-3-amidoxime (56.9 mg, 0.304 mmol) and 3-chloro-thiophene-2-carbonyl chloride (55 mg, 0.30 mmol) similar to Example 16, and yielded 85.0 mg (89%) of white solid. $^1$H NMR (CDCl$_3$): 9.64 (d, J=2.20 Hz, 1H), 8.95 (d, J=1.92 Hz, 1H), 8.20 (d, J=8.52 Hz, 1H), 7.98 (dd, J=7.97, 0.83 Hz, 1H), 7.82 (ddd, J=8.52, 7.00, 1.51 Hz, 1H), 7.65 (m, 2H), 7.17 (d, J=5.22 Hz, 1H).

EXAMPLE 69

5-(3-Chloro-thiophen-2-yl)-3-(8-hydroxy-quinolin-2-yl)-[1,2,4]-oxadiazole a) 8-Hydroxy-quinoline-2-amidoxime: The title compound was prepared from 8-hydroxy-quinoline-2-carbonitrile (508 mg, 2.99 mmol) and 50 wt % hydroxylamine (200 µL, 3.26 mmol) similar to Example 36c, and yielded 541 mg (89%) of white solid. $^1$H NMR (DMSO-$d_6$): 10.07 (s, 1H), 9.98 (s, 1H), 8.25 (d, J=8.79 Hz, 1H), 7.96 (d, J=8.79 Hz, 1H), 7.45 (t, J=7.33 Hz, 1H), 7.38 (dd, J=8.24, 1.38 Hz, 2H), 7.10 (dd, J=7.56, 1.51 Hz, 1H), 6.55 (s, 2H).

b) 5-(3-Chloro-thiophen-2-yl)-3-(8-hydroxy-quinolin-2-yl)-[1,2,4]-oxadiazole: The title compound was prepared from quinolin-8-ol-2-amidoxime (61.8 mg, 0.304 mmol) and 3-chloro-thiophene-2-carbonyl chloride (55 mg, 0.30 mmol) similar to Example 16, and yielded 16.3 mg (16%) of white solid. $^1$H NMR (CDCl$_3$): 8.61 (s, 1H), 8.34 (d, J=8.52 Hz, 1H), 8.29 (d, J=8.52 Hz, 1H), 7.66 (d, J=5.22 Hz, 1H), 7.56 (t, J=7.97 Hz, 1H), 7.41 (dd, J=8.24, 1.10 Hz, 1H), 7.26 (dd, J=8.24, 1.10 Hz, 1H), 7.17 (d, J=5.50 Hz, 1H).

EXAMPLE 70

5-(3-Cyano-thiophen-2-yl)-3-(5-trifluoromethyl-pyridin-2-yl)-[1,2,4]-oxadiazole

To a stirred solution of 3-cyano-thiophene-2-carboxylic acid (42.5 mg, 0.278 mmol) and methylene chloride (1.5 mL) in an ice bath under argon, was added oxalyl chloride (205 µL, 0.410 mmol) over 2 min and then 2 drops of dimethylformamide. The solution was stirred for 5 min, the ice bath was removed, and the solution was stirred for 1 h. The solution was concentrated to dryness to yield a white solid. To the solid was added 5-trifluoromethyl-pyridine-2-amidoxime (56.4 mg, 0.275 mmol) and pyridine (1.6 mL), and the resultant solution was stirred for 10 min at ambient temperature. The solution was then refluxed for 21 h. The solution was cooled to room temperature and the product was precipitated by addition of 5 mL of deionized water. The precipitate was filtered, washed with deionized water, and dried under vacuum to yield 38.3 mg (43%) of the title compound as a pink solid. $^1$H NMR (CDCl$_3$): 9.09 (m, 1H), 8.40 (d, J=8.25 Hz, 1H), 8.16 (dd, J=8.24, 2.20 Hz, 1H), 7.80 (d, J=5.22 Hz, 1H), 7.52 (d, J=5.22 Hz, 1H).

EXAMPLE 71

5-(3-Chloro-thiophen-2-yl)-3-(5,6-dichloro-pyridin-3-yl)-[1,2,4]-oxadiazole a) 5,6-Dichloro-pyridine-3-carbonitrile: To a stirred solution of 5,6-dichloro-pyridine-3-carboxylic acid (1.11 mg, 5.79 mmol) and methylene chloride (1.5 mL) in an ice bath under argon was added oxalyl chloride (4.4 mL, 8.8 mmol) over 25 min followed by 2 drops of dimethylformamide. The solution was stirred for 5 min, the ice bath was removed, and the solution was stirred for 1.5 h. The solution was concentrated to yield a white solid. To the solid was added tetrahydrofuran (5.0 mL) and 7 N ammonia in methanol (4.0 mL, 28.0 mmol). The solution was stirred for 1 min and then partitioned between deionized water (25 mL) and 1:1 dichloromethane:ethyl acetate (3×50 mL). The organic layers were concentrated. To the solid was added thionyl chloride (50 mL) and the solution was refluxed under argon for 69 h. The solution was concentrated and the residue was purified twice by column chromatography (1:2, hexane:ethyl acetate, then by 1:1, hexane:ethyl acetate) to yield 268 mg (27%) of the title compound. ¹H NMR (CDCl₃): 8.59 (d, J=2.20 Hz, 1H), 8.05 (d, J=2.20 Hz, 1H).

b) 5,6-Dichloro-pyridine-3-amidoxime: The title compound was prepared from 5,6-dichloro-pyridine-3-carbonitrile (257 mg, 1.485 mmol) and 50 wt % hydroxylamine (96.0 μL, 1.57 mmol) similar to Example 36c, and yielded 234 mg (76%) of product as a light yellow solid. ¹H NMR (DMSO-d₆): 10.11 (s, 1H), 8.66 (d, J=2.20 Hz, 1H), 8.29 (d, J=1.93 Hz, 1H), 6.12 (s, 2H).

c) 5-(3-Chloro-thiophen-2-yl)-3-(5,6-dichloro-pyridin-3-yl)-[1,2,4]-oxadiazole: The title compound was prepared from 5,6-dichloro-pyridine-3-amidoxime (101 mg, 0.491 mmol) and 3-chloro-thiophene-2-carbonyl chloride (88.9 mg, 0.491 mmol) similar to Example 16, and yielded 101 mg (62%) of white solid. ¹H NMR (CDCl₃): 9.06 (d, J=2.20 Hz, 1H), 8.52 (d, J=2.20 Hz, 1H), 7.66 (d, J=5.22 Hz, 1H), 7.16 (d, J=5.22 Hz, 1H).

EXAMPLE 72

5-(3-Bromo-furan-2-yl)-3-(5-chloro-pyridin-2-yl)-[1,2,4]-oxadiazole

The title compound was prepared from 3-bromo-furan-2-carboxylic acid (381.7 mg, 2.00 mmol) and 5-chloro-pyridine-2-amidoxime (343 mg, 2.00 mmol), similar to Example 70, and yielded 353 mg (54%) of white solid.
¹H NMR (CDCl₃): 8.81 (d, J=2.47 Hz, 1H), 8.22 (d, J=8.24 Hz, 1H), 7.90 (dd, J=8.25, 2.48 Hz, 1H), 7.71 (d, J=1.93 Hz, 1H), 6.79 (d, J=1.64 Hz, 1H).

EXAMPLE 73

5-(3-Bromo-furanBromo-furan-2-yl)-3-(6-trifluoromethyl-pyridin-3-yl)-[1,2,4]-oxadiazole The title compound was prepared from 6-trifluoromethyl-pyridine-3-amidoxime (508 mg, 2.48 mmol) and 3-bromo-furan-2-carbonyl chloride (520 mg, 2.48 mmol) similar to Example 16, and yielded 725 mg (81%) of light yellow solid. ¹H NMR (CDCl₃): 9.51 (m, 1H), 8.65 (dd, J=8.17, 1.99 Hz, 1H), 7.86 (d, J=8.10 Hz, 1H), 7.71 (d, J=1.92 Hz, 1H), 6.79 (d, J=1.92 Hz, 1H).

EXAMPLE 74

5-(3-Bromo-furan-2-yl)-3-(5-trifluoromethyl-pyridin-2-yl)-[1,2,4]-oxadiazole

The title compound was prepared from 5-trifluoromethyl-pyridine-2-amidoxime (480 mg, 2.34 mmol) and 3-bromo-furan-2-carbonyl chloride (490 mg, 2.34 mmol) similar to Example 16, and yielded 718 mg (85%) of light yellow solid. ¹H NMR (CDCl₃): 9.09 (m, 1H), 8.37 (d, J=8.24 Hz, 1H), 8.14 (dd, J=8.10, 2.34 Hz, 1H), 7.70 (d, J=1.92 Hz, 1H), 6.78 (d, J=1.92 Hz, 1H).

EXAMPLE 75

5-(3-Chloro-thiophen-2-yl)-3-(2-methyl-thiazol-4-yl)-[1,2,4]-oxadiazole

The title compound was prepared from 2-methyl-thiazole-4-amidoxime (24.6 mg, 0.156 mmol) and 3-chloro-thiophene-2-carbonyl chloride (28.7 mg, 0.159 mmol) similar to Example 16, and yielded 18.2 mg (40%) of white solid. ¹H NMR (CDCl₃): 8.03 (s, 1H), 7.61 (d, J=5.49 Hz, 1H), 7.13 (d, J=5.22 Hz, 1H), 2.84 (s, 3H).

EXAMPLE 76

5-(3-Chloro-thiophen-2-yl)-3-(5-nitro-thiazol-2-yl)-[1,2,4]-oxadiazole

The title compound was prepared from 5-nitro-thiazole-2-amidoxime (17.2 mg, 0.0914 mmol) and 3-chloro-thiophene-2-carbonyl chloride (16.4 mg, 0.0905 mmol) similar to Example 16, and yielded 6.7 mg (23%) of yellow solid. ¹H NMR (CDCl₃): 8.74 (s, 1H), 7.70 (d, J=5.22 Hz, 1H), 7.18 (d, J=5.22 Hz, 1H).

EXAMPLE 77

5-(3-Chloro-thiophen-2-yl)-3-(7-methyl-5-trifluoromethyl-pyrazolo[1,5α]pyrimidin-3-yl)-[1,2,4]-oxadiazole The title compound was prepared from 7-methyl-5-trifluoromethyl-pyrazolo[1,5α]pyrimidine-3-amidoxime (13.8 mg, 0.0532 mmol) and 3-chloro-thiophene-2-carbonyl chloride (9.8 mg, 0.0541 mmol) similar to Example 16, and yielded 9.8 mg (48%) of an off-white solid. ¹H NMR (CDCl₃): 8.89 (s, 1H), 7.62 (d, J=5.22 Hz, 1H), 7.20 (d, J=0.83 Hz, 1H), 7.14 (d, J=5.22 Hz, 1H), 2.98 (s, 3H).

EXAMPLE 78

5-(3-Bromo-furan-2-yl)-3-(4-chloro-phenyl)-[1,2,4]-oxadiazole

The title compound was prepared from 4-chlorobenzamidoxime (479 mg, 2.29 mmol) and 3-bromo-furan-2-carbonyl chloride (390 mg, 2.29 mmol) similar to Example 16, and yielded 570 mg (81%) of white solid. ¹H NMR (CDCl₃): 8.13 (dd, J=8.80, 2.20 Hz, 2H), 7.67 (d, J=1.92 Hz, 1H), 7.49 (dd, J=8.79, 2.20 Hz, 2H), 6.75 (d, J=1.92 Hz, 1H).

EXAMPLE 79

5-(3-Chloro-thiophen-2-yl)-3-[2-(4-chloro-phenyl)ethyl]-[1,2,4]-oxadiazole a) 3-(4-Chloro-phenyl)-propylamidoxime: The title compound was prepared from 3-(4-chloro-phenyl)-propionitrile (535 mg, 3.23 mmol) and 50 wt % hydroxylamine (120 μL, 1.96 mmol) similar to Example 36c, and yielded 240 mg (37%) of product as a white solid. ¹H NMR (DMSO-d₆): 8.75 (s, 1H), 7.32 (m, 2H), 7.24 (d, J=8.51 Hz, 1H), 6.12 (s, 2H), 2.79 (m, 2H), 2.22 (dd, J=8.93, 7.00 Hz, 1H).

b) 5-(3-Chloro-thiophen-2-yl)-3-[2-(4-chloro-phenyl)ethyl]-[1,2,4]-oxadiazole: The title compound was prepared from 3-(4-chloro-phenyl)-propylamidoxime (76.2 mg, 0.384 mmol) and 3-chloro-thiophene-2-carbonyl chloride (69.9 mg, 0.386 mmol) similar to Example 16, and yielded 71.8 mg (57%) of an off-white solid. ¹H NMR (CDCl₃): 7.58 (d, J=5.22 Hz, 1H), 7.26 (m, 2H), 7.18 (m, 2H), 7.11 (d, J=5.22 Hz, 1H), 3.10 (s, 4H).

EXAMPLE 80

5-(3-Chloro-thiophen-2-yl)-3-(4-chloro-phenoxymethyl)-[1,2,4]-oxadiazole

The title compound was prepared from 2-(4-chlorophenoxy)-ethylamidoxime (25.0 mg, 0.125 mmol) and 3-chlorothiophene-2-carbonyl chloride (23.1 mg, 0.128 mmol) similar to Example 16, and yielded 20.1 mg (57%) of brown solid. $^1$H NMR (CDCl$_3$): 7.62 (d, J=5.22 Hz, 1H), 7.27 (m, 2H), 7.12 (d, J=5.22 Hz, 1H), 6.98 (dd, J=9.07, 2.89 Hz, 2H), 5.23 (s, 2H).

EXAMPLE 81

5-(3-Chloro-thiophen-2-yl)-2-(4-trifluoromethoxyphenyl)-1H-imidazole

A solution of 4-trifluoromethoxy-benzamidine hydrochloride (102 mg, 0.42 mmol) in 3 M sodium hydroxide (10 mL) was extracted with dichloromethane (4×10 mL). The combined organic phases were dried over anhydrous sodium sulfate, decanted and concentrated to yield a white powder (74 mg, 73%). The white powder (64 mg, 0.27 mmol) was combined with 2-bromo-1-(3-chloro-thiophen-2-yl)-1-ethanone (54 mg, 0.23 mmol) and dimethylformamide (2.0 mL) and was heated at 50° C. under argon for 1 h. The solution was then cooled to room temperature and saturated sodium bicarbonate (6 mL) was added. The solution was extracted with dichloromethane (4×10 mL) and the combined organic phases were dried over anhydrous sodium sulfate, decanted, and concentrated. The product was purified by flash column chromatography (13:2, hexane:ethyl acetate) to yield 27 mg (34%) of the title compound as a white powder. $^1$H NMR (CDCl$_3$): 9.90 (s, 1H), 8.44 (m, 1H), 7.81 (d, J=1.92 Hz, 1H), 7.41 (m, 3H), 7.21 (d, J=5.50 Hz, 1H), 6.96 (d, J=5.50 Hz, 1H).

EXAMPLE 82

5-(3-Bromo-thiophen-2-yl)-2-(4-trifluoromethylphenyl)-1H-imidazole

The title compound was prepared from trifluoromethylbenzamidine (35 mg, 0.19 mmol), and 2-bromo-1-(3-bromothiophen-2-yl)-1-ethanone (52 mg, 0.18 mmol) similar to Example 81, and yielded 15 mg (22%) of brown solid. $^1$H NMR (CDCl$_3$): 10.19 (s, 1H), 7.91 (m, 3H), 7.63 (d, J=7.96 Hz, 2H), 7.21 (d, J=5.22 Hz, 1H), 7.02 (d, J=5.22 Hz, 1H).

EXAMPLE 83

5-(3-Chloro-thiophen-2-yl)-2-(4-trifluoromethylphenyl)-1H-imidazole

The title compound was prepared from trifluoromethylbenzamidine (26 mg, 0.15 mmol) and 2-bromo-1-(3-chlorothiophen-2-yl)-1-ethanone (37 mg, 0.15 mmol) similar to Example 81, and yielded 12 mg (24%) of brown solid. $^1$H NMR (CDCl$_3$): 10.18 (s, 1H), 7.92 (d, J=8.52, Hz, 2H), 7.73 (s, 1H), 7.64 (d, J=8.24 Hz, 2H), 7.21 (d, J=5.22 Hz, 1H), 6.97 (d, J=5.50 Hz, 1H).

EXAMPLE 84

5-(6-Chloro-pyridin-3-yl)-2-(3-chloro-thiophen-2-yl)-[1,3,4]-oxadiazole a) 3-Chloro-thiophene-carbonyl hydrazide: A solution of 3-chloro-thiophene-2-carbonyl chloride (647 mg, 3.57 mmol) in dichloromethane (10 mL) was added over 5 min to a stirred solution of hydrazine (350 μL, 11.2 mmol) in dichloromethane (10 mL) in an ice bath under argon. The ice bath was removed, and the solution was stirred for 2 h at ambient temperature. The solution was concentrated, and the residue was partitioned between water (10 mL) and dichloromethane (8×8 mL). The combined dichloromethane layers were dried over anhydrous sodium sulfate, decanted, and concentrated. The product was purified by column chromatography (43:57, hexane:ethyl acetate) to yield 502 mg (80%) of the title compound as a white solid. $^1$H NMR (CDCl$_3$): 8.11 (s, 1H), 7.50 (d, J=5.22 Hz, 1H), 6.99 (d, J=5.22 Hz, 1H), 4.11 (s, 2H).

b) 6-Chloro-nicotinic acid N'-(3-chloro-thiophene-2-carbonyl)-hydrazide: A solution of 3-chloro-thiophene-2-carbonyl hydrazide (70 mg, 0.40 mmol), 6-chloronicotinoyl chloride (76 mg, 0.43 mmol) and dichloromethane (10 mL) was stirred for 5 min. To the solution was added saturated sodium bicarbonate solution (10 mL) and it was stirred for 5 min. The layers were separated and the aqueous phase was extracted with dichloromethane (8×10 mL). Ethyl acetate (50 mL) was added to the combined organic phases, which were dried over anhydrous sodium sulfate, decanted, and concentrated to yield 120 mg (96%) of the title compound as a white powder. $^1$H NMR (DMSO-d$_6$): 10.89 (s, 1H), 10.37 (s, 1H), 8.89 (d, J=2.19 Hz, 1H), 8.30 (dd, J=8.52, 2.48 Hz, 1H), 7.93 (d, J=5.22 Hz, 1H), 7.72 (d, J=8.25 Hz, 1H), 7.22 (d, J=5.22 Hz, 1H).

c) 5-(6-Chloro-pyridin-3-yl)-2-(3-chloro-thiophen-2-yl)-[1,3,4]-oxadiazole: 6-Chloro-nicotinic acid N'-(3-chlorothiophene-2-carbonyl)-hydrazide (60 mg, 0.19 mmol) and thionyl chloride (6 mL) were refluxed under argon for 3.5 h, then was cooled to room temperature, and concentrated. The product was purified by column chromatography (5:2, hexane:ethyl acetate) to yield 33 mg (58%) of the title compound as an off-white powder.

$^1$H NMR (CDCl$_3$): 9.13 (d, J=2.48 Hz, 1H), 8.39 (dd, J=8.52, 2.48 Hz, 1H), 7.58 (d, J=5.22 Hz, 1H), 7.53 (d, J=8.24 Hz, 1H), 7.13 (d, J=5.22 Hz, 1H).

EXAMPLE 85

2-(3-Chloro-thiophen-2-yl)-5-(pyridin-3-yl)-[1,3,4]-oxadiazole a) Nicotinic acid N'-(3-chloro-thiophene-2-carbonyl)-hydrazide: The title compound was prepared from 3-chlorothiophene-2-carbonyl hydrazide (70 mg, 0.40 mmol) and nicotinoyl chloride hydrochloride (348 mg, 1.96 mmol) similar to Example 84b, and yielded 76 mg (68%) of white solid. $^1$H NMR (DMSO-d$_6$): 10.82 (s, 1H), 10.33 (s, 1H), 9.07 (s, 1H), 8.79 (d, J=3.84 Hz, 1H), 8.26 (d, J=6.87 Hz, 1H), 7.93 (d, J=5.22 Hz, 1H), 7.58 (dd, J=7.55, 4.53 Hz, 1H), 7.23 (d, J=4.95 Hz, 1H).

b) 2-(3-Chloro-thiophen-2-yl)-5-(pyridin-3-yl)-[1,3,4]-oxadiazole: The title compound was prepared from nicotinic acid N'-(3-chloro-thiophene-2-carbonyl)-hydrazide (52 mg, 0.18 mmol) and thionyl chloride similar to Example 84c, yielded 17 mg (35%) of white solid. $^1$H NMR (CDCl$_3$): 9.38

(s, 1H), 8.82 (s, 1H), 8.44 (d, J=7.97 Hz, 1H), 7.57 (d, J=5.22 Hz, 1H), 7.51 (dd, J=7.83, 4.54 Hz, 1H), 7.13 (d, J=5.22 Hz, 1H).

EXAMPLE 86

5-(4-Chloro-phenyl)-2-(3-chloro-thiophen-2-yl)-[1,3,4]-oxadiazole a) 4-Chloro-benzoic acid N'-(3-chloro-thiophene-2-carbonyl)-hydrazide: The title compound was prepared from 3-chloro-thiophene-2-carbonyl hydrazide (70 mg, 0.40 mmol) and 4-chlorobenzoyl chloride (50.5 µL, 0.40 mmol) similar to Example 84b, and yielded 130 mg (100%) of white solid. $^1$H NMR (DMSO-$d_6$): 10.66 (s, 1H), 10.30 (s, 1H), 7.93 (m, 3H), 7.61 (d, J=8.79 Hz, 1H), 7.22 (d, J=5.22 Hz, 1H).

b) 5-(4-Chloro-phenyl)-2-(3-chloro-thiophen-2-yl)-[1,3,4]-oxadiazole: The title compound was prepared from 4-chloro-benzoic acid N'-(3-chloro-thiophene-2-carbonyl)-hydrazide (55 mg, 0.17 mmol) and thionyl chloride similar to Example 84c, and yielded 46 mg (89%) of white solid. $^1$H NMR (CDCl$_3$): 8.08 (d, J=8.24 Hz, 2H), 7.53 (m, 3H), 7.11 (d, J=5.22 Hz, 1H).

EXAMPLE 87

5-(3-Bromo-5-morpholinomethyl-furan-2-yl)-3-(4-chloro-phenyl)-[1,2,4]-oxadiazole; and 5-(3-Bromo-5-hydroxymethyl-furan-2-yl)-3-(4-chloro-phenyl)-[1,2,4]-oxadiazole To a stirring solution of 5-(3-bromo-5-formyl-furan-2-yl)-3-(4-chloro-phenyl)-[1,2,4]-oxadiazole (60 mg, 0.170 mmol), sodium cyanoborohydride (10.5 mg, 0.167 mmol), acetic acid (10.0 µL, 0.173 mmol), and methanol (2.0 mL) under argon was added morpholine (50 µL, 0.57 mmol). The solution was stirred for 24 h and concentrated to dryness. The product was purified by column chromatography (2:1, hexane:ethyl acetate) to yield 12 mg (17%) of 5-(3-bromo-5-morpholinomethyl-furan-2-yl)-3-(4-chloro-phenyl)-[1,2,4]-oxadiazole as a white solid. $^1$H NMR (CDCl$_3$): 8.12 (d, J=8.51 Hz, 2H), 7.49 (d, J=8.52 Hz, 2H), 6.60 (s, 1H), 3.74 (t, J=4.67 Hz, 4H), 3.67 (s, 2H), 2.56 (t, J=4.67 Hz, 4H); and to also yield 12 mg (20%) of 5-(3-bromo-5-hydroxymethyl-furan-2-yl)-3-(4-chloro-phenyl)-[1,2,4]-oxadiazole as a white solid. $^1$H NMR (CDCl$_3$): 8.11 (dd, J=8.79, 2.20 Hz, 2H), 7.49 (dd, J=8.79, 2.20 Hz, 2H), 6.67 (s, 1H), 4.77 (d, J=6.32 Hz, 2H), 2.09 (t, J=6.46 Hz, 4H).

EXAMPLE 88

5-(3-Chloro-thiophen-2-yl)-3-(4-trifluoromethyl-phenyl)-1H-[1,2,4]-triazole a) 3-Chloro-thiophene-2-carboxylic acid hydrazide: To a solution of hydrazine (0.433 mL. 13.8 mmol) in dichloromethane (13.8 mL) cooled in an ice bath was added dropwise 3-chloro-thiophene-2-carbonyl chloride (1.0 g, 5.52 mmol) in 13.8 mL of dichloromethane. The reaction solution was slowly brought to room temperature after the addition, and stirred for 1.5 h. The solution was concentrated and the solid was suspended in deionized water (13.8 mL). The precipitate was filtered and dried under vacuum to yield 0.716 g (73%) of the title compound as a white solid. $^1$H NMR (DMSO-$d_6$): 9.40 (s, 1H), 7.81 (d, J=5.4 Hz, 1H), 7.12 (d, J=5.4 Hz, 1H), 4.56 (s, 2H).

b) 5-(3-Chloro-thiophen-2-yl)-3-(4-trifluoromethyl-phenyl)-1H-[1,2,4]-triazole: To a solution of 4-trifluoromethyl-benzamidine (0.442 g, 1,13 mmol) in ethanol (3 mL) was added sodium methoxide (0.442 g, 2.26 mmol) in ethanol (2.26 mL). The milky slurry was stirred at room temperature for 45 min and filtered. To the ethanol filtrate was added 3-chloro-thiophene-2-carboxylic acid hydrazide and the resultant solution was refluxed for 12 h, cooled to room temperature and the solvent was evaporated in vacuo. The solid was filtered, dried under vacuum, and purified by column chromatography (gradient 8:1-5:1 hexane:ethyl acetate) to yield 0.141 g (37%) of the title compound as a yellowish solid. $^1$H NMR (DMSO-$d_6$): 8.25 (d, J=8.4 Hz, 2H), 7.93 (d, J=8.1 Hz, 2H), 7.80 (d, J=6.0 Hz, 1H), 7.22 (d, J=5.70 Hz, 1H).

EXAMPLE 89

5-(3-Chloro-thiophen-2-yl)-3-phenyl-1H-[1,2,4]-triazole

The title compound was prepared from benzamidine hydrochloride and 3-chloro-thiophene-2-carboxylic acid hydrazide by a procedure similar to Example 88b as a yellowish solid (0.141 g, 37%). $^1$H NMR (DMSO-$d_6$): 8.04 (d, J=9.6 Hz, 2H), 7.80 (d, J=6.0 Hz, 1H), 7.55 (d, J=7.80 Hz, 3H), 7.19 (d, J=5.70 Hz, 1H).

EXAMPLE 90

5-(3-Chloro-thiophen-2-yl)-3-(4-methyl-phenyl)-1H-[1,2,4]-triazole

The title compound was prepared from 4-methyl-benzamidine hydrochloride and 3-chloro-thiophene-2-carboxylic acid hydrazide by a procedure similar to Example 88b as a yellow solid (0.054 g, 17%). $^1$H NMR (CD$_3$OD): 7.80 (d, J=7.8 Hz, 2H), 7.52 (d, J=6.0 Hz, 1H), 7.22 (d, J=8.4 Hz, 2H), 6.97 (d, J=5.10 Hz, 1H), 2.30 (s, 3H).

EXAMPLE 91

5-(3-Chloro-thiophen-2-yl)-3-(3-methyl-phenyl)-1H-[1,2,4]-triazole

The title compound was prepared from 3-methyl-benzamidine hydrochloride and 3-chloro-thiophene-2-carboxylic acid hydrazide by a procedure similar to Example 88b as a yellow solid (0.013 g, 5.6%). $^1$H NMR (CD$_3$OD): 7.75 (s, 1H), 7.69 (d, J=5.7 Hz, 1H), 7.4 (d, J=5.7 Hz, 1H), 7.24 (m, 2H), 6.97 (d, J=6.3 Hz, 1H), 3.10 (s, 3H).

EXAMPLE 92

5-(3-Chloro-thiophen-2-yl)-3-(pyridin-2-yl)-1H-[1,2,4]-triazole

The title compound was prepared from 2-amidine-pyridine hydrochloride and 3-chloro-thiophene-2-carboxylic acid hydrazide by a procedure similar to Example 88b as a yellow solid (0.025 g, 11.4%). $^1$H NMR (CD$_3$OD): 8.58 (s, 1H), 8.07 (d, J=8.1 Hz, 1H), 7.84 (t, J=1H), 7.49 (d, J=5.4 Hz, 1H), 7.36 (t, 1H), 6.98 (d, J=7.5 Hz, 1H).

EXAMPLE 93

2-(3-Chloro-thiophen-2-yl)-5-phenyl-oxazole a) 3-Chloro-thiophene-2-carboxylic acid (2-oxo-2-phenyl-ethyl)-amide: To a solution of 2-aminoacetophenone hydrochloride (0.098 g, 0.552 mmol) in pyridine (3 mL) cooled in an ice bath was added a solution of 3-chloro-thiophene-2-carbonyl chloride (0.100 g, 0.552 mmol) in pyridine (1 mL). The ice bath was removed after addition, and the resultant solution was stirred at room temperature for 1 h and then refluxed for 30 min. The reaction mixture was cooled to room temperature and the precipitate was filtered and dried under vacuum to yield 0.104 g (69%) of tan solid. $^1$H NMR (CD$_3$OD): 7.94 (d, J=9.9 Hz, 2H), 7.62 (d, J=5.1 Hz, 1H), 7.53 (t, 1H), 7.43 (t, 2H), 7.01 (d, J=6.3 Hz, 1H), 4.82 (s, 2H).

b) 2-(3-Chloro-thiophen-2-yl)-5-phenyl-oxazole: To sulfuric acid (1 mL) was added 3-chloro-thiophene-2-carboxylic acid (2-oxo-2-phenyl-ethyl)-amide (0.075 g, 0.330 mmol) portionwise and the solution was stirred at room temperature under argon for 0.5 h, then was poured over water (100 mL) and a precipitate was formed. The precipitate was filtered and the solid was dissolved in ethyl acetate, then washed with saturated sodium bicarbonate, dried over MgSO$_4$, filtered and concentrated to yield 0.027 g (44%) of the title compound as a tan solid. $^1$H NMR (CD$_3$OD): 7.67 (d, J=8.4 Hz, 2H), 7.56 (d, J=5.4 Hz, 1H), 7.50 (s, 1H), 7.36 (t, 2H), 7.26 (d, J=7.2 Hz, 1H), 7.03 (d, J=5.4 Hz, 1H).

EXAMPLE 94

5-(4-Bromo-phenyl)-2-(3-chloro-thiophen-2-yl)-oxazole a) 3-Choloro-thiophene-2-carboxylic acid [2-(4-bromo-phenyl)-2-oxo-ethyl]-amide: The compound was prepared from 3-chloro-thiophene-2-carbonyl chloride and 2-amino-4'-bromoacetophenone hydrochloride by a procedure similar to Example 93a as an orange solid. $^1$H NMR (DMSO-d$_6$): 8.40 (s, NH), 7.96 (d, J=8.7 Hz, 2H), 7.89 (d, J=5.1 Hz, 1H), 7.78 (d, J=8.7 Hz, 2H), 7.20 (d, J=5.1 Hz, 1H), 4.80 (d, J=5.4 Hz, 2H).

b) 5-(4-Bromo-phenyl)-2-(3-chloro-thiophen-2-yl)-oxazole: The title compound was prepared from 3-choloro-thiophene-2-carboxylic acid-[2-(4-bromo-phenyl)-2-oxo-ethyl]-amide by a procedure similar to Example 93b as a tan solid (0.059 g, 62%). $^1$H NMR (DMSO-d$_6$): 7.81 (s, 1H), 7.80 (d, J=5.1 Hz, 1H), 7.60 (s, 3H), 7.16 (d, J=5.4 Hz, 1H).

EXAMPLE 95

2-(3-Chloro-thiophen-2-yl)-5-(4-methoxy-phenyl)-oxazole a) 3-Choloro-thiophene-2-carboxylic acid-[2-(4-methoxy-phenyl)-2-oxo-ethyl]-amide: The title compound was prepared from 3-chloro-thiophene-2-carbonyl chloride and 2-amino-4'-methoxy acetophenone by a procedure similar to Example 93a as an orange solid. $^1$H NMR (DMSO-d$_6$): 8.30 (s, NH), 8.02 (d, J=9.0 Hz, 1H), 7.89 (d, J=6.6 Hz, 2H), 7.20 (d, J=6.0 Hz, 2H), 7.10 (d, J=8.7 Hz, 1H), 4.80 (d, J=5.4 Hz, 2H), 3.86 (s, 3H).

b) 2-(3-Chloro-thiophen-2-yl)-5-(4-methoxy-phenyl)-oxazole: The title compound was prepared from 3-choloro-thiophene-2-carboxylic acid-[2-(4-methoxy-phenyl)-2-oxo-ethyl]-amide by a procedure similar to Example 93b as a tan solid (0.023 g, 24%). $^1$H NMR (DMSO-d$_6$): 7.75 (d, J=5.1 Hz, 1H), 7.59 (m, 3H), 7.13 (d, J=5.1 Hz, 1H), 6.95 (d, J=8.7 Hz, 2H), 3.68 (s, 3H).

EXAMPLE 96

5-(4-Chloro-phenyl)-2-(3-chloro-thiophen-2-yl)-oxazole

The title compound was prepared from 3-choloro-thiophene-2-carboxylic acid-[2-(4-chloro-phenyl)-2-oxo-ethyl]-amide by a procedure similar to Example 93b as a tan solid (0.0058 g, 43%). $^1$H NMR (CD$_3$OD): 7.71 (d, J=5.1 Hz, 1H), 7.61 (m, 3H), 7.32 (d, J=8.5 Hz, 2H), 7.13 (d, J=5.1 Hz, 1H).

EXAMPLE 97

5-(3-Chloro-thiophen-2-yl)-2-phenyl-oxazole a) N-[2-(3-Chloro-thiophen-2-yl)-2-oxo-ethyl]-benzamide: To a solution of 2-(3-chloro-thiophen-2-yl)-2-oxo-1-ethylamine hydrochloride (0.05 g, 0.235 mmol) in pyridine (0.5 mL) and cooled in an ice bath was added benzoyl chloride (0.02 mL, 0.235 mmol) dropwise. The reaction solution was stirred in an ice bath for 15 min, poured over water, and extracted by ethyl acetate. The extracts were washed with 1N HCl solution, brine, and dried over MgSO$_4$, filtered and concentrated to yield 0.047 g (72.7%) of white solid. $^1$H NMR (CD$_3$OD): 7.79 (m, 3H), 7.43 (m, 3H), 7.05 (d, J=5.4 Hz, 1H), 4.75 (d, J=9.3 Hz, 2H).

b) 5-(3-Chloro-thiophen-2-yl)-2-phenyl-oxazole: A mixture of N-[2-(3-Chloro-thiophen-2-yl)-2-oxo-ethyl]-benzamide (0.048 g, 0.171 mmol) in sulfuric acid (1 mL) was stirred at room temperature for 40 min. The mixture was poured over water and filtered. The solid was dissolved in ethyl acetate and washed with water, saturated sodium bicarbonate, brine, and water. The organic layer was dried over MgSO$_4$, filtered and evaporated. The residue was purified by column chromatography (25: 1-100% CH$_2$Cl$_2$/MeOH) to yield 0.001 g (2.2%) of the title compound as a white solid. $^1$H NMR (Acetone-d$_6$): 7.99 (m, 2H), 2.26 (d, J=6.9 Hz, 2H), 7.45 (m, 3H), 7.07 (d, J=5.7 Hz, 1H).

EXAMPLE 98

2-(4-Chloro-phenyl)-5-(3-chloro-thiophen-2-yl)-oxazole a) N-[2-(3-Chloro-thiophen-2-yl)-2-oxo-ethyl]-4-chloro-benzamide: The title compound was prepared from 2-(3-chloro-thiophen-2-yl)-2-oxo-1-ethylamine hydrochloride (0.05 g, 0.235 mmol) and 4-chloro-benzoyl chloride (0.02 mL, 0.235 mmol) by a procedure similar to Example 97a to yield 0.048 g (72.7%) of white solid. $^1$H NMR (CD$_3$OD): 7.77 (m, 3H), 7.43 (d, J=8.4 Hz, 2H), 7.36 (t, 1H), 7.05 (d, J=5.4 Hz, 1H), 4.75 (d, J=9.3 Hz, 2H).

b) 2-(4-Chloro-phenyl)-5-(3-chloro-thiophen-2-yl)-oxazole: The title compound was prepared from N-[2-(3-chloro-thiophen-2-yl)-2-oxo-ethyl]4-chloro-benzamide (0.050 g, 0.159 mmol) by a procedure similar to Example 97b to yield 0.020 g (42%) of the title compound as a tan solid. $^1$H NMR (DMSO-d$_6$): 7.90 (d, J=8.4 Hz, 2H), 7.72 (t, 2H), 7.52 (d, J=9.0 Hz, 2H), 7.13 (d, J=5.4 Hz, 1H).

EXAMPLE 99

2-(6-Chloro-pyridin-3-yl)-5-(3-chloro-thiophen-2-yl)-oxazole a) 6-Chloro-N-[2-(3-chloro-thiphen-2-yl)-2-oxo-ethyl]-nicotinamide: The title compound was prepared from 2-(3-chloro-thiophen-2-yl)-2-oxo-1-ethylamine hydrochloride and 6-chloronicotinoyl chloride by a procedure similar to Example 98a as a white solid (0.044 g, 30%). $^1$H NMR (CD$_3$OD): 8.74 (d, J=8.74 Hz, 1H), 8.13 (d, J=6.3 Hz, 1H), 7.79 (d, J=5.4 Hz, 1H), 7.48 (d, J=9.0 Hz, 1H), 7.07 (d, J=5.4 Hz, 1H), 4.75 (s, 2H).

b) 2-(6-Chloro-pyridin-3-yl)-5-(3-chloro-thiophen-2-yl)-oxazole: The title compound was prepared from 6-chloro-N-[2-(3-chloro-thiophen-2-yl)-2-oxo-ethyl]-nicotinamide by a procedure similar to Example 98b as a tan solid (0.026 g, 69.2%). $^1$H NMR (DMSO-d$_6$): 8.88 (d, J=2.4 Hz, 1H), 8.25 (d, J=10.8 Hz, 1H), 7.75 (t, 2H), 7.60 (d, J=8.1 Hz, 1H), 7.14 (d, J=5.1 Hz, 1H).

EXAMPLE 100

5-(3-Chloro-thiophen-2-yl)-2-(4-trifluoromethyl-phenyl)-oxazole a) N-(2-(3-Chloro-thiophen-2-yl)-2-oxo-ethyl]4-trifluoromethyl-benzamide: The title compound was prepared from 2-(3-chloro-thiophen-2-yl)-2-oxo-1-ethylamine hydrochloride and 4-trifluoromethyl-benzoyl chloride by a procedure similar to Example 98a as a white solid (0.044 g, 30%). $^1$H NMR (DMSO-d$_6$): 9.06 (m, 1H), 7.99 (m, 3H), 7.77 (d, J=8.4 Hz, 2H), 7.20 (d, J=9.0 Hz, 1H), 4.73 (s, 2H).

b) 5-(3-Chloro-thiophen-2-yl)-2-(4-trifluoromethyl-phenyl)-oxazole: The title compound was prepared from N-(2-(3-chloro-thiophen-2-yl)-2-oxo-ethyl]-4-trifluoromethyl-benzamide by a procedure similar to Example 98b as a white solid (0.0056 g, 11.8%). $^1$H NMR (Acetone-d$_6$): 8.18 (d, J=9.9 Hz, 2H), 7.80 (d, J=9.60 Hz, 2H), 7.69 (s, 1H), 7.65 (d, J=5.4 Hz, 1H), 7.08 (d, J=5.7 Hz, 1H).

EXAMPLE 101

2-(3-Chloro-thiophen-2-yl)-4-(4-trifluoromethyl-phenyl)-oxazole

3-Chloro-thiophene-2-carboxamide (0.145 g, 0.898 mmol) and 4-trifluoromethyl-phenacyl bromide (0.200 g, 0.749 mmol) were placed in a sealed tube and heated at 150° C. for 4 h. The reaction mixture was quenched with ethyl acetate and the residue was purified by column chromatography (gradient 100:1, 20:1 hexane:dichloromethane). The product was further purified by preparative-TLC (100:1, hexane:dichloromethane) to yield 0.0148 g (5.0%) of the title compound as a white solid. $^1$H NMR (Acetone-d$_6$): 8.58 (s, 1H), 8.01 (d, J=8.1 Hz, 2H), 7.71 (t, 3H), 7.10 (d, J=5.1 Hz, 1H), 7.08 (d, J=5.7 Hz, 1H).

EXAMPLE 102

4-(4-Chloro-phenyl)-2-(3-chloro-thiophen-2-yl)-oxazole

The title compound was prepared from 3-chloro-thiophene-2-carboxamide (0.100 g, 1.03 mmol) and 4-chloro-phenacyl bromide (0.200 g, 0.856 mmol) by a procedure similar to Example 101 as a white solid (0.006 g, 3.2%). $^1$H NMR (Acetone-d$_6$): 8.45 (s, 1H), 7.80 (d, J=6.6 Hz, 2H), 7.70 (d, J=6.0 Hz, 1H), 7.38 (d, J=8.1 Hz, 2H), 7.08 (d, J=6.0 Hz, 1H).

EXAMPLE 103

3-(4-Chloro-phenyl)-5-(3-chloro-thiophen-2-yl)-1H-pyrazole a) 3-(4-Chloro-phenyl)-1-(3-chloro-thiophen-2-yl)-propenone: To a solution of 1-(3-chloro-thiophen-2-yl)-1-ethanone (0.450 g, 2.80 mmol) and 4-chlorobenzaldehyde (0.393 g, 2.80 mmol) in ethanol (11.2 mL) was added 0.5 M aqueous sodium hydroxide (5.6 mL). The reaction mixture was stirred for 2.5 h, diluted with ethyl acetate (20 mL), washed with 1N HCl, brine, dried over MgSO$_4$, filtered and evaporated to yield a yellowish solid (0.530 g, 60%). $^1$H NMR (Acetone-d$_6$): 7.87 (d, J=5.4 Hz, 1H), 7.70 (m, 4H), 7.40 (d, J=8.4 Hz, 2H), 7.11 (d, J=5.4 Hz, 1H).

b) 3-(4-Chloro-phenyl)-5-(3-chloro-thiophen-2-yl)-1H-pyrazole: To a solution of 3-(4-chloro-phenyl)-1-(3-chloro-thiophen-2-yl)-propenone (50 mg, 0.176 mmol) in ethanol (1.5 mL) and sodium hydroxide (7.0 mg, 0.176 mmol) was added hydrazine (5 μL) dropwise and the reaction mixture was heated at 70° C. for 16 h. It was concentrated and the residue was purified by chromatography (3:1, hexane:ethyl acetate) to yield 5.0 mg (8.0%) of an off-white solid. $^1$H NMR (Acetone-d$_6$): 7.77 (d, J=8.7 Hz, 2H), 7.40 (d, J=8.4 Hz, 3H), 7.16 (s, 1H), 6.96 (d, J=5.1 Hz, 1H).

EXAMPLE 104

4-Chloro-N-[5-(3-chloro-thiophen-2-yl)-[1,2,4]-oxadiazol-3-yl]-benzamide a) 4-Chloro-N-cyano-benzamide: A solution of cyanamide (124 mg, 2.94 mmol) in 3.0 M NaOH (3.0 mL) was added to a solution of 4-chloro-benzoyl chloride (310 μL, 2.43 mmol) in ether (4.0 mL), and the mixture was stirred for 2.5 h. The mixture was acidified to pH 3 with 10% HCl to form a precipitate. The precipitate was filtered, washed with water, and dried under vacuum overnight to yield 353 mg of crude product as a white solid.

b) 4-Chloro-N-(N-hydroxy-amidine)benzamide: A solution of the above crude 4-chloro-N-cyano-benzamide (164 mg), 50 wt % aqueous hydroxylamine and ethanol was stirred for 2 h at room temperature. The solution was concentrated and the title compound was purified by column chromatography (95:5, ethyl acetate:methanol) to yield 55.1 mg of the title compound as a white solid.

c) 4-Chloro-N-[5-(3-chloro-thiophen-2-yl)-[1,2,4]-oxadiazol-3-yl]-benzamide: A solution of 4-chloro-N-(N-hydroxy-amidine)benzamide (38.2 mg, 0.179 mmol), 3-chloro-thiophene-2-carbonyl chloride (32.8 mg, 0.181 mmol) and pyridine (2.0 mL) was stirred for 10 min at room temperature under argon. The solution was refluxed for 1 h, cooled to room temperature and diluted by water (6 mL) to form a precipitate. The precipitate was filtered and dried under vacuum. The product was purified by preparative TLC (2:1, hexane:ethyl acetate) to yield 4.1 mg (7%) of the title compound as a white solid. $^1$H NMR (CDCl$_3$): 9.32 (s, 1H), 8.09 (dd, J=8.79, 2.06 Hz, 2H), 7.65 (d, J=5.49 Hz, 4H), 7.49 (dd, J=8.79, 2.06 Hz, 2H), 7.09 (d, J=5.22 Hz, 4H).

EXAMPLE 105

5-(4-Chloro-phenyl)-3-(3-chloro-thiophen-2-yl)-1-phenyl-1H-pyrazole a) 5-(4-Chloro-phenyl)-3-(3-chloro-thiphen-2-yl)-1-phenyl-4,5-dihydro-1H-pyrazole: To a solution of 3-(4-chloro-phenyl)-1-(3-chloro-thiophen-2-yl)-propenone (50 mg, 0.176 mmol) in ethanol (1.5 mL) and sodium hydroxide (7.0 mg, 0.176 mmol) was added phenylhydrazine (17 μL, 0.176 mmol) dropwise and the reaction solution was heated at 70° C. for 3 h. It was concentrated to dryness, and the residue was purified by chromatography (50:1, hexane:ethyl acetate) to yield 12.8 mg (19.4%) of yellowish oil. $^1$H NMR (CDCl$_3$): 7.18 (m, 9H), 6.88 (d, J=8.7 Hz, 2H), 6.77 (d, J=5.4 Hz, 1H), 6.69 (t, 1H), 5.14 (m, 1H), 3.93 (m, 1H), 3.22 (m, 1H).

b) 5-(4-Chloro-phenyl)-3-(3-chloro-thiophen-2-yl)-1-phenyl-1H-pyrazole: To a solution of 5-(4-chloro-phenyl)-3-(3-chloro-thiophen-2-yl)-1-phenyl-4,5-dihydro-1H-pyrazole (11.0 mg, 0.029 mmol) in dichloromethane (0.2 mL) was added dropwise a solution of lead tetracetate (6.6 mg, 0.029 mmol) in dichloromethane (0.1 mL). The reaction mixture was stirred at room temperature for 15 min, then diluted with water (1 mL). The organic layer was washed with water, dried over MgSO$_4$, and evaporated to yield an oil. The oil was dissolved in a solution of HCl/ethanol (0.1 mL, 0.225M) and heated at 60° C. for 10 min. Dichloromethane was added after cooling and the organic layer was washed with sodium bicarbonate and water, dried over MgSO$_4$ and concentrated The residue was purified by chromatography (50:1, hexane:ethyl acetate) to yield 5.9 mg (54%) of the title compound as a tan solid. $^1$H NMR (CDCl$_3$): 7.15 (m, 11H), 6.87 (d, J=5.4 Hz, 1H), 4.00 (d, J=7.2 Hz, 1H).

EXAMPLE 106

5-(4-Chloro-phenyl)-3-(3-chloro-thiophen-2-yl)-1-methyl-1H-pyrazole a) 5-(4-Chloro-phenyl)-3-(3-chloro-thiophen-2-yl)-1-methyl-4,5-dihydro-1H-pyrazole: The title compound was prepared from 3-(4-chloro-phenyl)-1-(3-chloro-thiophen-2-yl)-propenone (50 mg, 0.176 mmol) and methylhydrazine (9 μL, 0.17 mmol) by a procedure similar to Example 105a as a yellowish oil (20.9 mg, 38%). $^1$H NMR (CDCl$_3$): 7.24 (m, 4H), 7.09 (d, J=6.6 Hz, 1H), 6.75 (d, J=6.60 Hz, 1H), 4.08 (m, 1H), 3.83 (m, 1H), 2.98 (t, 1H), 2.67 (s, 3H).

b) 5-(4-Chloro-phenyl)-3-(3-chloro-thiophen-2-yl)-1-methyl-1H-pyrazole: The title compound was prepared from 5-(4-chloro-phenyl)-3-(3-chloro-thiophen-2-yl)-1-methyl-4,5-dihydro-1H-pyrazole (19.0 mg, 0.061 mmol) similar to Example 105b as a tan solid (9.5 mg, 48%). $^1$H NMR (CDCl$_3$): 7.30 (m, 4H), 7.09 (d, J=5.7 Hz, 1H), 6.83 (d, J=6.0 Hz, 2H), 3.78 (s, 3H).

EXAMPLE 107

5-(4-Chloro-phenyl)-1-(3-chloro-phenyl)-3-(3-chloro-thiophen-2-yl)-1H-pyrazole a) 5-(4-Chloro-phenyl)-1-(3-chloro-phenyl)-3-(3-chloro-thiophen-2-yl)-4,5-dihydro-1H-pyrazole: The title compound was prepared from 3-(4-chloro-phenyl)-1-(3-chloro-thiophen-2-yl)-propenone and 3-chloro-phenylhydrazine by a procedure similar to that of Example 105a as a yellowish solid (93.8 mg, 43%). $^1$H NMR (CDCl$_3$): 7.29 (m, 7H), 6.92 (m, 3H), 5.25 (m, 1H), 4.08 (m, 1H), 3.83 (m, 1H).

b) 5-(4-Chloro-phenyl)-1-(3-chloro-phenyl)-3-(3-chloro-thiophen-2-yl)-1-phenyl-1H-pyrazole: The title compound was prepared from 5-(4-chloro-phenyl)-1-(3-chloro-phenyl)-3-(3-chloro-thiophen-2-yl)-4,5-dihydro-1H-pyrazole by a procedure similar to that of Example 105b as a tan solid (5.0 mg, 5.4%). $^1$H NMR (CDCl$_3$): 7.52 (t, 1H), 7.28 (m, 8H), 7.13 (d, J=9.0 Hz, 1H), 7.02 (d, J=5.7 Hz, 1H).

EXAMPLE 108

1,5-Bis-(4-chloro-phenyl)-3-(3-chloro-thiophen-2-yl)-1H-pyrazole a) 1,5-Bis-(4-chloro-phenyl)-3-(3-chloro-thiophen-2-yl)-4,5-dihydro-1H-pyrazole: The title compound was prepared from 3-(4-chloro-phenyl)-1-(3-chloro-thiophen-2-yl)-propenone and 4-chloro-phenylhydrazine by a procedure similar to that of Example 105a as a yellowish oil (112 mg, 51.8%). $^1$H NMR (CDCl$_3$): 7.35 (d, J=8.7 Hz, 2H), 7.27 (t, 3H), 7.15 (d, J=9.3 Hz, 2H), 6.91 (m, 3H), 5.25 (m, 1H), 4.03 (m, 1H), 3.83 (m, 1H).

b) 1,5-bis-(4-Chloro-phenyl)-3-(3-chloro-thiophen-2-yl)-1-phenyl-1H-pyrazole: The title compound was prepared from 1,5-bis-(4-chloro-phenyl)-3-(3-chloro-thiophen-2-yl)-4,5-dihydro-1H-pyrazole by a procedure similar to that of Example 105b as a tan solid (5.4 mg, 5.6%). $^1$H NMR (CDCl$_3$): 7.29 (m, 10H), 7.02 (d, J=5.7 Hz, 1H).

EXAMPLE 109

5-(4-Chloro-phenyl)-3-(3-chloro-thiophen-2-yl)-1-(pyridin-2-yl)-1H-pyrazole a) 5-(4-Chloro-phenyl)-3-(3-chloro-thiophen-2-yl)-1-(pyridin-2-yl)-4,5-dihydro-1H-pyrazole: The title compound was prepared from 3-(4-chloro-phenyl)-1-(3-chloro-thiophen-2-yl)-propenone and 2-hydrazinopyridine by a procedure similar to that of Example 105a as a yellowish oil (141 mg, 73.8%). $^1$H NMR (CDCl$_3$): 8.04 (m, 1H), 7.59 (t, 1H), 7.46 (d, J=9.0 Hz, 1H), 7.27 (m, 6H), 6.92 (d, J=5.4 Hz, 1H), 6.68 (t, 1H), 4.01 (t, 1H), 3.41 (m, 1H).

b) 5-(4-Chloro-phenyl)-3-(3-chloro-thiophen-2-yl)-1-(pyridin-2-yl)-1H-pyrazole: The title compound was prepared from 5-(4-chloro-phenyl)-3-(3-chloro-thiophen-2-yl)-1-(pyridin-2-yl)-4,5-dihydro-1H-pyrazole by a procedure similar to that of Example 105b as a clear crystal (9.0 mg, 6.2%).
$^1$H NMR (CDCl$_3$): 8.35 (m, 1H), 7.83 (t, 1H), 7.71 (d, J=10.2 Hz, 1H), 7.30 (m, 6H), 7.02 (d, J=6.9 Hz, 1H).

EXAMPLE 110

5-(4-Chloro-phenyl)-3-(3-chloro-thiophen-2-yl)-1-(4-carboxy-phenyl)-1H-pyrazole a) 5-(4-Chloro-phenyl)-3-(3-chloro-thiophen-2-yl)-1-(4-carboxy-phenyl)4,5-dihydro-pyrazole: The title compound was prepared from 3-(4-chloro-phenyl)-1-(3-chloro-thiophen-2-yl)-propenone and 4-hydrazinobenzoic acid by a procedure similar to that of Example 105a as a yellowish oil (166 mg, 74%). $^1$H NMR (CDCl$_3$): 9.02 (s, 1H), 7.92-6.80 (m, 10H), 5.72 (m, 1H), 4.20 (m, 1H), 4.01 (t, 1H), 3.41 (m, 1H).

b) 5-(4-Chloro-phenyl)-3-(3-chloro-thiophen-2-yl)-1-(4-carboxy-phenyl)-1H-pyrazole: The title compound was prepared from 5-(4-chloro-phenyl)-3-(3-chloro-thiophen-2-yl)-1-(4-carboxy-phenyl)-4,5-dihydro-1H-pyrazole by a procedure similar to that of Example 105b as a tan solid (1.0 mg, 1.4%).

$^1$H NMR (CDCl$_3$): 7.78 (s, 1H), 7.76 (d, J=3.3 Hz, 2H), 7.44 (d, J=8.4 Hz, 2H), 7.30 (d, J=9.0 Hz, 2H), 7.15 (d, J=5.4 Hz, 1H), 6.98 (d, J=8.7 Hz, 2H), 5.77 (s, 1H).

EXAMPLE 111

5-(4-Chloro-phenyl)-3-(3-chloro-thiophen-2-yl)-1-(4-methanesulfonyl-phenyl)-1H-pyrazole a) 5-(4-Chloro-phenyl)-3-(3-chloro-thiophen-2-yl)-1-(4-methane-sulfonyl-phenyl)-4,5-dihydro-pyrazole: The title compound was prepared from 3-(4-chloro-phenyl)-1-(3-chloro-thiophen-2-yl)-propenone and 4-methyl-sulfonylphenylhdrazine by a procedure similar to that of Example 105a as a yellowish oil (78 mg, 32%). $^1$H NMR (CDCl$_3$): 7.69 (d, J=9.0 Hz, 1H), 7.33 (m, 3H), 7.22 (m, 4H), 6.92 (m, 2H), 5.38 (t, 1H), 4.15 (m, 1H), 3.46 (m, 1H), 1.29 (m, 3H).

b) 5-(4-Chloro-phenyl)-3-(3-chloro-thiophen-2-yl)-1-(4-methane-sulfonyl-phenyl)-1H-pyrazole: The title compound was prepared from 5-(4-chloro-phenyl)-3-(3-chloro-thiophen-2-yl)-1-(4-methanesulfonyl-phenyl)-4,5-dihydro-pyrazole by a procedure similar to that of Example 105b as a tan solid (14.2 mg, 18.0%). $^1$H NMR (CDCl$_3$): 7.97 (m, 3H), 7.58 (m, 2H), 7.44 (d, J=8.7 Hz, 2H), 7.29 (m, 2H), 7.02 (d, J=5.4 Hz, 1H), 5.77 (s, 1H), 3.09 (s, 3H).

EXAMPLE 112

5-(4-Chloro-phenyl)-3-(3-chloro-thiophen-2-yl)-1-(2-hydroxyethyl)-1H-pyrazole a) 5-(4-Chloro-pheneyl)-3-(3-chloro-thiophen-2-yl)-1-(2-hydroxy-ethyl)-4,5-dihydro-pyrazole: The title compound was prepared from 3-(4-chloro-phenyl)-1-(3-chloro-thiophen-2-yl)-propenone and 2-hydroxyethyl-hydrazine by a procedure similar to that of Example 105a as a yellowish oil (88 mg, 73%). $^1$H NMR (CDCl$_3$): 7.40 (m, 6H), 6.91 (d, J=5.1 Hz, 1H), 3.78 (m, 2H), 2.97 (m, 2H).

b) 5-(4-Chloro-phenyl)-3-(3-chloro-thiophen-2-yl)-1-(2-hydroxyethyl)-1H-pyrazole: The title compound was prepared from 5-(4-chloro-pheneyl)-3-(3-chloro-thiophen-2-yl)-1-(2-hydroxyethyl)-4,5-dihydro-pyrazole by a procedure similar to that of Example 105b as a tan solid (4.8 mg, 3.6%). $^1$H NMR (CDCl$_3$): 7.48 (m, 4H), 7.25 (d, J=5.4 Hz, 1H), 6.98 (t, 2H), 4.24 (m, 2H), 3.51 (m, 2H).

EXAMPLE 113

5-(3-Chloro-thiophen-2-yl)-3-(4-chloroanilino) [1,2,4]-oxadiazole a) 3-Chloro-thiophene-2-cyanoamide: To a solution of cyanamide (0.232 g, 5.52 mmol) in 10% sodium hydroxide solution was added 3-chloro-thiophene-2-carbonyl chloride (1.0 g, 5.52 mmol) in diethyl ether (2 mL). The solution was stirred for 40 min at room temperature and 10 min in an ice bath, then 1N HCl was added dropwise. The precipitate was collected and purified by chromatography (gradient 4:1, hexane:ethyl acetate:methanol) to yield 0.561 g (56%) of tan solid. $^1$H NMR (DMSO-d$_6$): 7.48 (d, J=5.7 Hz, 1H), 6.94 (d, J=6.3 Hz, 1H), 5.78 (s, 1H).

b) N-(4-Chloro-phenyl)-N-(3-chloro-thiophene-2-carbonyl)-guanidine: To a solution of 3-chloro-thiophene-2-cyanoamide (0.207 g, 1.11 mmol) in water (5 mL) was added p-chloroaniline, followed by 2N HCl to adjust the pH at 3. The reaction mixture was refluxed for 3 h to form a white solid. The reaction mixture was cooled to room temperature and washed with sodium hydroxide (0.5 M), water, brine, then dried over MgSO$_4$, filtered, and concentrated. The residue was purified by column chromatography (10:0.1, dichloromethane:methanol) to yield 0.083 g (24%) of tan solid. $^1$H NMR (CDCl$_3$): 7.29 (d, J=9.0 Hz, 2H), 7.25 (d, J=5.1 Hz, 1H), 7.10 (d, J=9.0 Hz, 2H), 6.86 (d, J=5.1 Hz, 1H).

c) 5-(3-Chloro-thiophen-2-yl)-3-(4-chloroanilino)[1,2,4]-oxadiazole: To N-(4-chloro-phenyl)-N-(3-chloro-thiophene-2-carbonyl)-guanidine (50.0 mg, 0.159 mmol) in methanol (1.0 mL) was added hydrochloric acid (0.146 mL). Precipitate formed immediately and the solid was removed by filtration. To the solution was added NaOCl (0.08 mL) and aqueous potassium carbonate (0.152 mL, 1.0 M). The reaction mixture was stirred at room temperature for 1 h and the precipitate was collected by filtration. The solid was purified by column chromatography (dichloromethane) to yield 0.008 g (17.1%) of the title compound a white solid. $^1$H NMR (Acetone-d$_6$): 8.02 (d, J=5.4 Hz, 1H), 7.53 (d, J=8.7 Hz, 2H), 7.23 (m, 3H).

EXAMPLE 114

5-(3-Bromo-furan-2-yl)-3-(4-fluoro-phenyl)-[1,2,4]-oxadiazole a) 3-Bromo-furan-2-carboxylic acid: To a solution of lithium diisopropylamine (26.2 mL, 1.4 M) in tetrahydrofuran (26 mL) cooled at −78° C. was added dropwise a solution of 3-bromo-furan (5.0 g, 34.0 mmol) in tetrahydrofuran (26 mL). The solution was stirred for 30 min at −78° C., then poured into a solution of carbon dioxide and ether and stirred for 10 min. The slurry was poured into water (careful that a lot of emission of gas could produce a violent reaction) and the aqueous phase was separated. The aqueous phase was acidified to pH 3 by 2N HCl and extracted 3 times with ethyl acetate. The combined organic layers were dried over MgSO$_4$, filtered and concentrated. The solid was recrystallized from hexane and ethyl acetate to yield 4.21 g (64.8%) of yellowish powder. $^1$H NMR (CDCl$_3$): 7.58 (m, 1H), 6.66 (m, 1H).

b) 5-(3-Bromo-furan-2-yl)-3-(4-fluoro-phenyl)-[1,2,4]-oxadiazole: To a mixture of 3-bromo-furan-2-carboxylic acid (0.700 g, 3.66 mmol) in anhydrous benzene (9 mL) was added thionyl chloride (0.9 mL) and the reaction mixture was heated at 60° C. for 6 h. The reaction mixture was concentrated to dryness (an oil) and then co-evaporated with hexane several times to yield a semi-solid. To the semi-solid was added 4-fluoro-benzamidoxime (0.147 g, 0.955 mmol) and pyridine (2 mL) and the solution was refluxed for 12 h. After cooling to room temperature, the solution was poured over water, and extracted by ethyl acetate. The organic layer was dried over MgSO$_4$, filtered and concentrated. The compound was purified by column chromatography (3:1, hexane:ethyl acetate) and further purified by chromatography (3:1, hexane:ethyl acetate) to yield 14.3 mg (4.8%) of yellowish powder. $^1$H NMR (Acetone-d$_6$): 8.21 (m, 2H), 8.07 (d, J=1.8 Hz, 1H), 7.39 (t, 2H), 7.03 (d, J=2.1 Hz, 1H).

EXAMPLE 115

5-(3-Chloro-furan-2-yl)-3-(5-chloro-pyridin-2-yl)-[1,2,4]-oxadiazole a) 3-Chloro-furan: A solution of freshly distilled 3-bromo-furan (19.49 g, 132.1 mmol) in anhydrous THF (40 mL) and anhydrous ether (70 mL) was cooled to −78° C. and stirred for 20 min. To the solution was then added n-butyllithium in pentene (66.3 mL, 2.0 M) dropwise by an addition funnel. The reaction mixture was stirred for 0.5 h at −78° C. and then hexachloroethane (31.39 g, 132.6 mmol) in anhydrous THF (15 mL) was added dropwise to the stirring solution. The reaction solution was stirred for an additional 1 h at −78° C. The ice bath was removed, then the reaction was stirred at room temperature for 2 h, and precipitate was formed. The mixture was poured over water, separated, quenched with 2N HCl, washed with water, dried over MgSO$_4$, filtered, and distilled under vacuum (bp: 35-40° C.) to yield 6.09 g (44.7%) of light yellow liquid. $^1$H NMR (CDCl$_3$): 7.36 (m, 1H), 7.30 (t, 1H), 6.33 (m, 1H).

b) 3-Chloro-furan-2-carboxylic acid: The title compound was prepared similar to Example 114a to yield 4.48 g (51.2%) of yellowish powder. $^1$H NMR (CDCl$_3$): 7.57 (d, J=2.1 Hz, 1H), 6.59 (d, J=1.8 Hz, 1H).

c) 5-(3-Chloro-furan-2-yl)-3-(5-chloro-pyridin-2-yl)-[1,2,4]-oxadiazole: The title compound was prepared from 3-chloro-furan-2-carboxylic acid (0.250 g, 1.71 mmol) and 5-chloro-pyridine-2-amidoxime (0.288 g, 1.68 mmol) to yield 101 mg (20.9%) of yellowish powder. $^1$H NMR (DMSO-d$_6$): 8.87 (m, 1H), 8.28 (d, J=2.1 Hz, 1H), 8.19 (d, J=2.1 Hz, 1H), 8.18 (d, J=0.9 Hz, 1H), 7.15 (d, J=2.1 Hz, 1H).

EXAMPLE 116

5-(3-Chloro-furan-2-yl)-3-(4-trifluoromethyl-phenyl)-[1,2,4]-oxadiazole

The title compound was prepared according to Example 115c as a white powder (190 mg, 35.5%). $^1$H NMR (DMSO-d$_6$): 8.29 (m, 3H), 7.99 (d, J=8.7 Hz, 2H), 7.16 (d, J=1.8 Hz, 1H).

EXAMPLE 117

5-(3-Chloro-furan-2-yl)-3-(4-chloro-phenyl)-[1,2,4]-oxadiazole

The title compound was prepared according to Example 115c as a white powder (1.89 g, 65.5%). $^1$H NMR (DMSO-d$_6$): 8.27 (d, J=1.8 Hz, 1H), 8.08 (d, J=8.7 Hz, 2H), 7.69 (d, J=8.7 Hz, 2H), 7.15 (d, J=1.8 Hz, 1H).

EXAMPLE 118

5-(3-Bromo-furan-2-yl)-3-(5-trifluoromethyl-pyridin-2-yl)-[1,2,4]-oxadiazole a) 2-Iodo-5-trifluromethyl-pyridine: To a solution of 2-chloro-5-trifluoromethyl-pyridine (15.0 g, 82.6 mmol) in acetonitrile (400 mL) was added sodium iodide (43.3 g, 289.1 mmol), and the reaction mixture was stirred at 88° C. until all the sodium iodine dissolved. To the solution was then added acetyl chloride (8.8 mL, 12.3 mmol), and a precipitate was formed. The reaction mixture was refluxed for 24 h, cooled and concentrated to an oil. The oil was dissolved in dichloromethane, washed with 10% sodium thiosulfate, 10% sodium carbonate and brine, dried over MgSO$_4$, filtered and concentrated. The residue was purified by chromatography and eluted with dichloromethane to yield 10.9 g (48.4%) of light yellow product. $^1$H NMR (CDCl$_3$): 8.68 (s, 1H), 7.88 (m, 1H), 7.49 (d, J=9.9 Hz, 1H).

b) 5-Trifluoromethyl-pyridine-2-carbonitrile: To a solution of 2-iodo-5-trifluromethyl-pyridine (10.9 g, 40.0 mmol) in pyridine (250 mL) was added copper cyanide (5.37 g, 60.0 mmol), and the reaction mixture was refluxed for 2 h. The reaction mixture was cooled, washed with potassium cyanide and water, dried over MgSO$_4$, filtered, and concentrated to a brown oil. The oil was purified by column chromatography (gradient 6:1-4:1, hexane:ethyl acetate) to yield 5.09 g (74%) of yellowish powder. $^1$H NMR (CDCl$_3$): 9.01 (s, 1H), 8.11 (m, 1H), 7.86 (d, J=7.5 Hz, 1H).

c) 5-Trifluoromethyl-pyridine-2-amidoxime: To a solution of 5-trifluoromethyl-pyridine-2-carbonitrile (5.00 g, 29.5 mmol) in ethanol (100 mL) was added hydroxylamine (2.0 mL), and the solution was refluxed for 12 h. It was then concentrated to yield 5.46 g (89%) of white solid. $^1$H NMR (CDCl$_3$): 8.83 (s, 1H), 8.05 (m, 1H), 6.99 (s, 1H).

d) 5-(3-Bromo-furan-2-yl)-2-(5-trifluoromethyl-pyridin-2-yl)-[1,2,4]-oxadiazole: The title compound was prepared similar to Example 115c as a yellowish powder. $^1$H NMR (DMSO-d$_6$): 10.2 (s, 1H), 8.17 (d, J=5.4 Hz, 1H), 7.89 (d, J=8.7 Hz, 2H), 7.41 (d, J=5.4 Hz, 1H), 6.94 (d, J=8.7 Hz, 2H).

EXAMPLE 119

5-(3-Bromo-furan-2-yl)-3-(5-chloro-pyridin-2-yl)-[1,2,4]-oxadiazole

The title compound was prepared similar to Example 115c as a yellowish powder (2.7 mg, 2.7%). $^1$H NMR (CDCl$_3$): 8.75 (m, 1H), 8.15 (d, J=9.0 Hz, 1H), 7.84 (d, J=10.8 Hz, 1H), 7.60 (d, J=5.1 Hz, 1H), 7.18 (d, J=5.1 Hz, 1H).

EXAMPLE 120

3-(4-Amino-3,5-diiodo-phenyl)-5-(3-chloro-thiophen-2-yl)-[1,2,4]-oxadiazole

To a solution of 3-(4-aminophenyl)-5-(3-chloro-thiophen-2-yl)-[1,2,4]-oxadiazole (100 mg, 0.36 mmol) in acetic acid (3 mL) was added a solution of iodine monochloride (175.74 mg, 1.08 mmol) in acetic acid (1 mL). It was stirred at room temperature for 1 h and was then concentrated in vacuo. The residue was purified by column chromatography (hexane:ethyl acetate, 8:1) to yield 56 mg (30%) of the title compound. $^1$H NMR (CDCl$_3$): 8.45 (s, 2H), 7.63 (d, J=5.1 Hz, 1H), 7.15 (d, J=5.1 Hz, 2H), 5.01 (brs, 2H).

EXAMPLE 121

Identification of 5-(3-Chloro-thiophen-2-yl)-3-(4-trifluoromethyl-phenyl)-[1,2,4]-oxadiazole and Analogs as Caspase Cascade Activators and Inducers of Apoptosis in Solid Tumor Cells Human breast cancer cell lines T-47D and ZR-75-1 were grown according to media component mixtures designated by American Type Culture Collection+10% FCS (Invitrogen Corporation), in a 5% CO$_2$-95% humidity incubator at 37° C. T-47D and ZR-75-1 cells were maintained at a cell density between 50 and 80% confluency at a cell density of 0.1 to 0.6×10$^6$ cells/mL. Cells were harvested at 600×g and resuspended at 0.65×10$^6$ cells/mL into appropriate media+10% FCS. An aliquot of 45 μl of cells was added to a well of a 96-well microtiter plate containing 2.5 μl of a 10% DMSO in RPMI-1640 media solution containing 0.16 to 100 μM of 5-(3-chloro-thiophen-2-yl)-3-(4-trifluoromethyl-phenyl)-[1,2,4]-oxadiazole or other test compound (0.016 to 10 μM final). An aliquot of 22.5 μL of cells was added to a well of a 384-well microtiter plate containing 2.5 μl of a 10% DMSO in RPMI-1640 media solution without test compound as the control sample. The samples were mixed by agitation and then incubated at 37° C. for 48 h in a 5% $CO_2$-95% humidity incubator. After incubation, the samples were removed from the incubator and 25 μL of a solution containing 14 μM of N—(Ac-DEVD)-N'-ethoxycarbonyl-R110 (SEQ ID No.:1) fluorogenic substrate (Maxim, Inc.; WO99/18856), 20% sucrose (Sigma), 20 mM DTT (Sigma), 200 mM NaCl (Sigma), 40 mM Na PIPES buffer pH 7.2 (Sigma), and 500 μg/mL lysolecithin (Calbiochem) was added. The samples were mixed by agitation and incubated at room temperature. Using a fluorescent plate reader (Model SpectraMax Gemini, Molecular Devices), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for 5-(3-chloro-thiophen-2-yl)-3-(4-trifluoromethyl-phenyl)-[1,2,4]-oxadiazole or other test compound to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

Caspase Activity and Potency

| | T-47D | |
|---|---|---|
| Example | Ratio | $EC_{50}$ (nM) |
| 1 | 16.9 | 3614 |
| 4 | 4.2 | 5354 |
| 5 | 19.7 | 2145 |
| 6 | 3.8 | 5000 |
| 7 | 4.1 | 865 |

Thus, 5-(3-chloro-thiophen-2-yl)-3-(4-trifluoromethyl-phenyl)-[1,2,4]-oxadiazole (Example 4) and analogs are identified as potent caspase cascade activators and inducers of apoptosis in solid tumor cells.

EXAMPLE 122

Identification of 5-(3-Chloro-thiophen-2-yl)-3-(4-trifluoromethyl-phenyl)-[1,2,4]-oxadiazole as Antineoplastic Compound that Inhibits Cell Proliferation ($GI_{50}$)

T-47D and SKBr-3 cells were grown and harvested as in Example 121. An aliquot of 90 μL of cells ($2.2 \times 10^4$ cells/mL) was added to a well of a 96-well microtiter plate containing 10 μl of a 10% DMSO in RPMI-1640 media solution containing 1 nM to 100 μM of 5-(3-chloro-thiophen-2-yl)-3-(4-trifluoromethyl-phenyl)-[1,2,4]-oxadiazole (0.1 nM to 10 μM final). An aliquot of 90 μL of cells was added to a well of a 96-well microtiter plate containing 10 μL of a 10% DMSO in RPMI-1640 media solution without compound as the control sample for maximal cell proliferation ($A_{Max}$). The samples were mixed by agitation and then incubated at 37° C. for 48 h in a 5% $CO_2$-95% humidity incubator. After incubation, the samples were removed from the humidity incubator and 20 μL of CellTiter 96 $AQ_{UEOUS}$ One Solution Cell Proliferation™ reagent (Promega) was added. The samples were mixed by agitation and incubated at 37° C. for 2-4 h in a 5% $CO_2$-95% humidity incubator. Using an absorbance plate reader (Model 1420 Wallac Instruments), an initial reading (T=0) was made approximately 1-2 min after addition of the solution, employing absorbance at 490 nm. This determines the possible background absorbance of the test compounds. No absorbance for 5-(3-chloro-thiophen-2-yl)-3-(4-trifluoromethyl-phenyl)-[1,2,4]-oxadiazole was found at 490 nm. After the 2-4 h incubation, the samples were read for absorbance as above ($A_{Test}$).

Baseline for $GI_{50}$ (dose for 50% inhibition of cell proliferation) of initial cell numbers were determined by adding an aliquot of 90 μL of cells or 90 μL of media, respectively, to wells of a 96-well microtiter plate containing 10 μL of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 20 μL of CellTiter 96 $AQ_{UEOUS}$ One Solution Cell Proliferation™ reagent (Promega) was added. The samples were mixed by agitation and incubated at 37° C. for 2-4 h in a 5% $CO_2$-95% humidity incubator. Absorbance was read as above, ($A_{Start}$) defining absorbance for initial cell number used as baseline in $GI_{50}$ determinations.

Calculation:

$GI_{50}$ (dose for 50% inhibition of cell proliferation) is the concentration where $[(A_{Test}-A_{Start})/(A_{Max}-A_{Start})]=0.5$.

The $GI_{50}$ (nM) are summarized in Table II:

TABLE II $GI_{50}$ in Cancer Cells

| | $GI_{50}$ (nM) | |
|---|---|---|
| Cell lines | Example 5 | Example 1 |
| T-47D | 300 | 250 |
| ZR75-1 | 400 | 200 |

Thus, 5-(3-chloro-thiophen-2-yl)-3-(4-trifluoromethyl-phenyl)-[1,2,4]-oxadiazole (Example 4) and 3-(4-chloro-phenyl)-5-(3-chloro-thiophen-2-yl)-[1,2,4]-oxadiazole (Example 1) are identified as antineoplastic compound that inhibits cell proliferation.

EXAMPLE 123

Identification of 5-(3-Chloro-thiophen-2-yl)-3-(4-trifluoromethyl-phenyl)-[1,2,4]-oxadiazole as Antineoplastic Compound that Selectively Inhibits the Proliferation of Breast Cancer Cells ($GI_{50}$)

T-47D, ZR-75-1, MX-1, SK-Br-3, Panc-1, K562, HeLa and PC-3 cells were grown according to the conditions recommended by American Type Culture Collection. SW620 and NCI-H23 were grown according to the conditions provided by National Cancer Institute. The cell proliferation assay and the calculations of $GI_{50}$ were performed as in Example 122 (Tables III and IV).

TABLE III

GI$_{50}$ in Breast Cancer Cell Lines.

| Cell Line | GI$_{50}$(nM) Example 5 | Example 1 |
|---|---|---|
| T47D | 300 | 250 |
| ZR 75-1 | 400 | 200 |
| MX-1 | 400 | 300 |
| SK-Br-3 | 20 | 20 |

TABLE IV

GI$_{50}$ in Non-breast Cancer Cell Lines.

| Cell Line | GI$_{50}$(nM) Example 5 | Example 1 |
|---|---|---|
| PC-3 | >10,000 | >10,000 |
| Panc-1 | >10,000 | >10,000 |
| SW-620 | >10,000 | >10,000 |
| NCI-H23 | >10,000 | >10,000 |
| K562 | >10,000 | >10,000 |
| DLD-1 | 40 | 35 |

Thus 5-(3-chloro-thiophen-2-yl)-3-(4-trifluoromethyl-phenyl)-[1,2,4]-oxadiazole (Example 4) and 3-(4-chloro-phenyl)-5-(3-chloro-thiophen-2-yl)-[1,2,4]-oxadiazole (Example 1) were identified as antineoplastic compounds that selectively inhibits the growth of breast cancer cell lines, with an exception of DLD-1, a colon cancer cell line.

EXAMPLE 124

5-(3-Chloro-thiophen-2-yl)-3-(4-trifluoromethyl-phenyl)-[1,2,4]-oxadiazole Inhibits the Clonogenic Survival of MX-1 Solid Tumor Cell Lines MX-1 cells were grown according to the conditions recommended by American Type Culture Collection. In a well of a 96 well plate, 30,000 cells were seeded and treated with compound at the indicated concentrations for 48 h in a 5% CO$_2$-95% humidity incubator at 37° C. Control wells were treated with the same amount of solvent (DMSO) as the compound samples. After the indicated treatment time, the supernatant was removed to a sterile culture tube and the wells washed with phosphate buffered saline, and the adherent cells trypsinized for 5 min. The trypsinzed cells were added to the culture supernatant, cells were collected (1,200 rpm, 10 min), washed with phosphate buffered saline, and resupended in fresh media. The cells were counted for trypan blue negative cells, and the cells diluted with fresh media to 1,000 cells/mL. To a well of a 24-well plate, 0.1 mL of the cell suspension was added along with 1 mL of fresh media (cell suspensions were passed through a 22 G needle several times just before plating to form single cell suspensions). Plates are incubated in a 5% CO$_2$-95% humidity incubator at 37° C. for 7-10 days. Colonies are counted when the sizes reached greater than 50 cells per colony. Cells are washed with phosphate buffered saline, fixed with 100% methanol for 15 min, and then stained with 0.5% gentian violet for 15 min. Colonies are rinsed with water and the colonies counted and the fraction surviving expressed as the percentage of the number of control colonies.

The results showed that after a 48 h treatment 5-(3-chloro-thiophen-2-yl)-3-(4-trifluoromethyl-phenyl)-[1,2,4]-oxadiazole inhibited the ability of MX-1 cells to proliferate and their colony forming ability with an IC$_{50}$ of approximately 1050 nM.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

---

---

What is claimed is:

1. A method of treating breast cancer or colon carcinoma in an animal suffering therefrom, comprising administering to an animal in need of such treatment an effective amount of a compound having the Formula II:

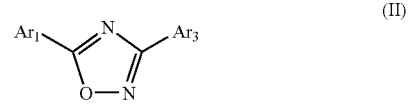

(II)

or a pharmaceutically acceptable salt or prodrug or tautomers thereof, wherein:

Ar$_1$ is optionally substituted heteroaryl; and

Ar$_3$ is optionally substituted and selected from the group consisting of pyridyl, quinolyl, isoquinolyl, isoxazolyl, pyrazolyl, imidazolyl, thienyl, furyl, pyrrolyl and pyrazolo[1,5α]pyrimidinyl.

2. The method of claim 1, wherein Ar₁ is pyridyl, quinolyl, isoquinolyl, isoxazolyl, pyrazolyl, imidazolyl, thienyl, furyl or pyrrolyl, each of which is optionally substituted.

3. The method of claim 1, wherein Ar₁ is isoxazolyl, pyrazolyl, imidazolyl, thienyl, furyl or pyrrolyl, each of which is optionally substituted; and Ar₃ is optionally substituted pyridyl.

4. The method of claim 1, wherein said compound is selected from the group consisting of:
- 5-(4-Bromo-1-ethyl-3-methyl-1H-pyrazol-5-yl)-3-(5-trifluoromethyl-pyridin-2-yl)-[1,2,4]-oxadiazole;
- 5-(2-Methyl-pyrrol-3-yl)-3-(pyridin-3-yl)-[1,2,4]-oxadiazole;
- 5-(3-Chloro-thiophen-2-yl)-3-(pyridin-4-yl)-[1,2,4]-oxadiazole;
- 5-(3-Chloro-thiophen-2-yl)-3-(pyridin-3-yl)-[1,2,4]-oxadiazole;
- 5-(3-Chloro-thiophen-2-yl)-3-(pyridin-2-yl)-[1,2,4]-oxadiazole;
- 5-(3-Chloro-thiophen-2-yl)-3-(N-oxide-pyridin-4-yl)-[1,2,4]-oxadiazole;
- 5-(3-Methyl-furan-2-yl)-3-(5-trifluoromethyl-pyridin-2-yl)-[1,2,4]-oxadiazole;
- 5-(4-Chloro-1H-pyrazol-3-yl)-3-(5-trifluoromethyl-pyridin-2-yl)-[1,2,4]-oxadiazole;
- 5-(3-Chloro-furan-2-yl)-3-(5-trifluoromethyl-pyridin-2-yl)-[1,2,4]-oxadiazole;
- 5-(4-Chloro-thiazol-5-yl)-3-(5-chloro-pyridin-2-yl)-[1,2,4]-oxadiazole;
- 5-(3-Chloro-thiophen-2-yl)-3-(5-chloro-pyridin-2-yl)-[1,2,4]-oxadiazole;
- 5-(3-Chloro-thiophen-2-yl)-3-(5-trifluoromethyl-pyridin-2-yl)-[1,2,4]-oxadiazole;
- 5-(3-Chloro-thiophen-2-yl)-3-(N-oxide-pyridin-3-yl)-[1,2,4]-oxadiazole;
- 5-(3-Chloro-thiophen-2-yl)-3-(6-chloro-pyridin-3-yl)-[1,2,4]-oxadiazole;
- 5-(3-Chloro-thiophen-2-yl)-3-(5-trifluoromethyl-pyridin-2-yl)-[1,2,4]-oxadiazole;
- 5-(3-Chloro-thiophen-2-yl)-3-(6-trifluoromethyl-pyridin-3-yl)-[1,2,4]-oxadiazole;
- 5-(3-Chloro-thiophen-2-yl)-3-(quinoline-2-yl)-[1,2,4]-oxadiazole;
- 5-(3-Chloro-thiophen-2-yl)-3-(isoquinoline-3-yl)-[1,2,4]-oxadiazole;
- 5-(3-Chloro-thiophen-2-yl)-3-(4-methyl-pyridin-2-yl)-[1,2,4]-oxadiazole;
- 5-(3-Chloro-thiophen-2-yl)-3-(4-cyano-pyridin-2-yl)-[1,2,4]-oxadiazole;
- 5-(3-Chloro-thiophen-2-yl)-3-(5-methyl-pyridin-2-yl)-[1,2,4]-oxadiazole;
- 5-(3-Chloro-thiophen-2-yl)-3-(6-methyl-pyridin-3-yl)-[1,2,4]-oxadiazole;
- 5-(3-Chloro-thiophen-2-yl)-3-(pyrazin-2-yl)-[1,2,4]-oxadiazole;
- 5-(3-Chloro-thiophen-2-yl)-3-(quinolin-3-yl)-[1,2,4]-oxadiazole;
- 5-(3-Chloro-thiophen-2-yl)-3-(8-hydroxy-quinolin-2-yl)-[1,2,4]-oxadiazole;
- 5-(3-Cyano-thiophen-2-yl)-3-(5-trifluoromethyl-pyridin-2-yl)-[1,2,4]-oxadiazole;
- 5-(3-Chloro-thiophen-2-yl)-3-(5,6-dichloro-pyridin-3-yl)-[1,2,4]-oxadiazole;
- 5-(3-Bromo-furan-2-yl)-3-(5-chloro-pyridin-2-yl)-[1,2,4]-oxadiazole;
- 5-(3-Bromo-furan-2-yl)-3-(6-trifluoromethyl-pyridin-3-yl)-[1,2,4]-oxadiazole;
- 5-(3-Bromo-furan-2-yl)-3-(5-trifluoromethyl-pyridin-2-yl)-[1,2,4]-oxadiazole;
- 5-(3-Chloro-thiophen-2-yl)-3-(7-methyl-5-trifluoromethyl-pyrazolo[1,5-α]pyrimidin-3-yl)-[1,2,4]-oxadiazole;
- 5-(3-Chloro-furan-2-yl)-3-(5-chloro-pyridin-2-yl)-[1,2,4]-oxadiazole;
- 5-(3-Bromo-furan-2-yl)-3-(5-trifluoromethyl-pyridin-2-yl)-[1,2,4]-oxadiazole;
- 5-(3-Bromo-furan-2-yl)-3-(5-chloro-pyridin-2-yl)-[1,2,4]-oxadiazole; and
- 5-(3-Chloro-thiophen-2-yl)-3-(6-methoxy-pyridin-3-yl)-[1,2,4]-oxadiazole;

or a pharmaceutically acceptable salt or prodrug thereof.

5. The method of claim 1, wherein said animal is a mammal.

6. The method of claim 1 additionally comprising administering at least one known cancer chemotherapeutic agent, or a pharmaceutically acceptable salt of said agent.

7. The method of claim 6, wherein said known cancer therapeutic agent is selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, campath, imatinib, trastuzumab or rituximab and alanosine.

8. The method of claim 1 additionally comprising treating said animal with radiation-therapy.

9. The method of claim 1 wherein said compound is administered after surgical treatment of said animal for said cancer.

10. The method of claim 1, wherein Ar₂ is pyridyl, which is optionally substituted.

11. The method of claim 1 wherein the disease is breast cancer.

12. The method of claim 1 wherein the disease is colon carcinoma.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Fluorogenic substrate

<400> SEQUENCE: 1

Asp Glu Val Asp
1